(12) United States Patent
Berkenstam et al.

(10) Patent No.: US 9,012,495 B2
(45) Date of Patent: Apr. 21, 2015

(54) CRYSTALLINE FORMS OF GENISTEIN

(75) Inventors: Anders Berkenstam, Stockholm (SE);
Stefan Rehnmark, Tullinge (SE);
Michael-Robin Witt, Sodertalji (SE);
Keith Lorimer, West Lafayette, IN
(US); Stephen Watt, Riccarton (GB)

(73) Assignee: Axcentua Pharmaceuticals AB (SE)

( * ) Notice: Subject to any disclaimer, the term of this patent is extended or adjusted under 35 U.S.C. 154(b) by 292 days.

(21) Appl. No.: 13/133,085

(22) PCT Filed: Dec. 11, 2009

(86) PCT No.: PCT/US2009/067664
§ 371 (c)(1),
(2), (4) Date: Oct. 17, 2011

(87) PCT Pub. No.: WO2010/068861
PCT Pub. Date: Jun. 17, 2010

(65) Prior Publication Data
US 2012/0035253 A1 Feb. 9, 2012

Related U.S. Application Data

(60) Provisional application No. 61/121,778, filed on Dec. 11, 2008, provisional application No. 61/121,787, filed on Dec. 11, 2008.

(51) Int. Cl.
*A61K 31/352* (2006.01)
*C07D 311/74* (2006.01)
*C07D 311/22* (2006.01)

(52) U.S. Cl.
CPC ............ *A61K 31/352* (2013.01); *C07D 311/22* (2013.01)

(58) Field of Classification Search
CPC .................................................... C07D 311/22
USPC .......................................... 514/456; 549/403
See application file for complete search history.

(56) References Cited

U.S. PATENT DOCUMENTS

| | | | | | |
|---|---|---|---|---|---|
| 4,841,077 | A | * | 6/1989 | Ito et al. ........................ | 549/402 |
| 5,569,459 | A | * | 10/1996 | Shlyankevich ............... | 424/728 |
| 5,637,703 | A | | 6/1997 | Mazurek et al. | |
| 5,637,704 | A | | 6/1997 | Guenther et al. | |
| 2003/0157225 | A1 | * | 8/2003 | Husband et al. ............. | 426/430 |
| 2004/0023981 | A1 | | 2/2004 | Ren et al. | |
| 2004/0106561 | A1 | | 6/2004 | Kelly | |
| 2006/0020021 | A1 | | 1/2006 | Salinas et al. | |
| 2008/0131907 | A1 | | 6/2008 | Wang et al. | |

FOREIGN PATENT DOCUMENTS

| | | |
|---|---|---|
| JP | 09-183774 | 7/1997 |
| JP | 2000-512988 T | 10/2000 |
| JP | 2002-047191 A | 2/2002 |
| JP | 2008-530160 T | 8/2006 |
| WO | 9706273 A1 | 2/1997 |
| WO | 9722596 A1 | 6/1997 |
| WO | 9730035 A1 | 8/1997 |
| WO | 9732856 A1 | 9/1997 |
| WO | 9813354 A1 | 4/1998 |
| WO | 9902166 A1 | 1/1999 |
| WO | 0015627 A1 | 3/2000 |
| WO | 0040529 A1 | 7/2000 |
| WO | 0041669 A2 | 7/2000 |
| WO | 0192224 A1 | 12/2001 |
| WO | 0204434 A1 | 1/2002 |
| WO | 0208213 A1 | 1/2002 |
| WO | 02/081491 A2 | 10/2002 |
| WO | 2004058781 A1 | 7/2004 |
| WO | 2007022138 A2 | 2/2007 |
| WO | 2007/061254 A1 | 5/2007 |
| WO | 2010068861 A1 | 6/2010 |

OTHER PUBLICATIONS

Swartz, M. "Contemporary Challenges in Pharmaceutical Counter Ion Analysis." Synomics Pharma.*
American Cancer Society. "Can cancer of the esophagus be prevented?" © 2013. Available from: < http://www.cancer.org/cancer/esophaguscancer/detailedguide/esophagus-cancer-prevention >.*
Mayo Clinic. "Prostate cancer prevention: Ways to reduce your risk." © 2013. Available from: < http://www.mayoclinic.com/health/prostate-cancer-prevention/MC00027 >.*
American Cancer Society. "Can kidney cancer be prevented?" © 2013. Available from: < http://www.cancer.org/cancer/kidneycancer/detailedguide/kidney-cancer-adult-prevention >.*
Mayo Clinic. "Pancreatic Cancer." © 2013. Available from: < http://www.mayoclinic.com/health/pancreatic-cancer/DS00357/DSECTION=prevention >.*
Akiyama et al., J. Biol. Chem. (1987) vol. 262, pp. 5592-5595.
Gilman et al. (Ed.), Goodman and Gilman's "The Pharmacological Basis of Therapeutics" (2001, 10th ed.) McGraw Hill Press, pp. 155-173.

(Continued)

*Primary Examiner* — Andrew D Kosar
*Assistant Examiner* — John S Kenyon
(74) *Attorney, Agent, or Firm* — J.A. Lindeman & Co., PLLC

(57) ABSTRACT

The disclosure relates to new crystalline forms of genistein. The disclosed crystalline forms include crystalline genistein sodium salt dihydrate; crystalline genistein potassium salt dihydrate; crystalline genistein calcium salt; crystalline genistein magnesium salt; crystalline genistein L-lysine salt; crystalline genistein N-methylglucamine salt; crystalline genistein N-ethylglucamine salt; crystalline genistein diethylamine salt; and crystalline genistein monohydrate. The disclosure also relates to the novel genistein salts represented by these crystalline forms. Therapeutic compositions containing at least one of these crystalline forms of genistein and/or a genistein salt and a pharmaceutically acceptable carrier are described. The disclosure also relates to methods of treating cancer comprising the step of administering to a patient in need thereof a therapeutically effective amount of a therapeutic composition containing the compounds of the disclosure, of a crystalline form of genistein, or of a genistein salt.

19 Claims, 39 Drawing Sheets

(56) References Cited

OTHER PUBLICATIONS

Grynkiewicz et al., "X-ray and 13C CP MAS Investigations of Structure of Two Genistein Derivatives," J.Mol. Struct. (2004) vol. 694, p. 121.
Hakansson and Allen, FEBS Lett. (1995) vol. 372, pp. 238-242.
Huang et al., J. Biol. Chem. (1992) vol. 267, pp. 15511-15515.
Igarashi and Komiya, J. Neurosci. Res. (1991) vol. 30, pp. 266-274.
Kozerski et al., "Solution and Solid State 13C NMR and X-ray Studies of Genistein Complexes with Amines. Potential Biological Function of the C-7, C-5, and C-4-OH Groups," Org. Biomol. Chem. (2003) vol. 1, p. s3578.
Li and Sarkar, Cancer Lett. (2002) vol. 186, p. 157.
Mazurek et al., "Genistein Complexes with Amines: Structure and Properties," J. Chem. Soc., Perkin Trans. (1998) vol. 2, p. 1223.
O'Dell et al., Nature (1991) vol. 353, pp. 558-560.
Remington's Pharmaceutical Sciences, (1990, 18th Ed.) Mack Publishing Co.
Wietrzyk et al., Anticancer Res. (2001) vol. 12, pp. 3893-3896.
Polkowski et al., "Genistein and its complexes. Part III. (1, 2) Experimental and quantum-chemical semiempirical studies." Acta Potomac Pharmaceutica—Drug Research 56(2):109-116 (1999).
Supplementary European Search Report for EP 09 83 2607 (related to PCT International Application No. PCT/US2009/067664, dated Aug. 2, 2012.
Zhang et al. Hydrogen bonding and pi-pi stacking in methylaminium 4',7-dihydroxy-isoflavone-3'-sulfonate dihydrate and hexaaquairon(II) bis(4',7-diethoxy-isoflavone-3'-sullonate) tetrahydrate. Acta Cryslallographica Section C, Crystal Structure Communications, C62, m484-m487, Sep. 12, 2006, p. m484, col. 2.
International Search Report and Written Opinion for PCT International Application No. PCT/US2009/067664, dated Dec. 11, 2009.

* cited by examiner

CRYSTALLINE FORMS OF GENISTEIN

CROSS-REFERENCE TO RELATED APPLICATIONS

This application claims priority to U.S. provisional application 61/121,778, filed Dec. 11, 2008, and to U.S. provisional application 61/121,787, filed Dec. 11, 2008, both of which are incorporated herein by reference.

BACKGROUND

Cancer is characterized by uncontrolled cell growth which occurs when the normal regulation of cell proliferation is lost. This loss often appears to be the result of dysregulation of the cellular pathways involved in cell growth and division, apoptosis, angiogenesis, tumor invasion and metastasis.

Genistein, 4′5,7-trihydroxyisoflavone-5,7-dihydro-3-(4-hydroxyphenyl)-4H-1-benzopyran-4-one, (shown below), is a natural compound present in plants such as soy. Genistein's potential role in the prevention and treatment of a number of human diseases

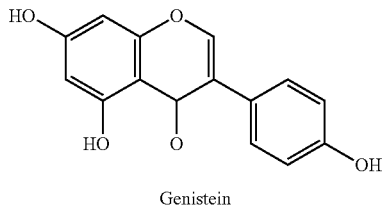 [SMILES: Oc1ccc(C2=COc3cc(O)cc(O)c3C2O)cc1]

Genistein including cancer has been extensively studied. Genistein is a BCS class II isoflavone that is commercially available from a number of sources including LC Laboratories, Woburn, Mass. The cellular targets for genistein and the signaling pathways regulated by genistein have been identified and those related to cancer include targets and pathways important for cell growth and division, apoptosis, angiogenesis, tumor invasion and metastasis. In addition to the inherent anti-tumor effects of genistein itself, studies have shown that genistein also potentiates, or accentuates, the anti-tumor effects of several clinically used chemotherapeutic agents both in vitro in human cancer cell lines and in vivo in animal models of cancer. From a therapeutic perspective, these data are interesting as chemotherapy is the cornerstone in the treatment of most solid tumors.

Genistein is practically insoluble in water but has high cell membrane permeability. Low water solubility and slow dissolution rate are often limiting factors responsible for the low bioavailability of pharmaceutical compounds, limiting their application.

Despite the long known fact that genistein has certain properties of anti-cancer drugs, no successful genistein treatment regimens have been, or are, employed in the treatment of cancers. One plausible explanation for this is probably the poor solubility and poor bioavailability as well as the rapid phase II metabolism of genistein in its known form.

Due to the development of the drug discovery strategy over the last 20 years, physicochemical properties of drug development candidates have changed significantly. The development candidates are generally more lipophilic and less water soluble, which creates huge problems for the industry. Research has shown that some drug candidates fail in the clinical phase due to poor human bioavailability and problems with the formulation. Traditional methods to address these problems, without completely redesigning the molecule, include salt selection, producing amorphous material, particle size reduction, pro-drugs, and different formulation approaches. Recently, crystalline forms of active pharmaceutical ingredient (API) have been used to alter the physicochemical properties of the API.

Although therapeutic efficacy is the primary concern for a therapeutic agent, the salt and solid state form (i.e., the crystalline or amorphous form) of a drug candidate can be critical to its pharmacological properties and to its development as a viable API. For example, each salt or each crystalline form of a drug candidate can have different solid state (physical and chemical) properties. The differences in physical properties exhibited by a novel solid form of an API (such as a cocrystal, salt, or polymorph of the original compound) affect pharmaceutical parameters such as storage stability, compressibility and density (important in formulation and product manufacturing), and solubility and dissolution rates (important factors in determining bioavailability). Because these practical physical properties are influenced by the solid state properties of the crystalline form of the API, they can significantly impact the selection of a compound as an API, the ultimate pharmaceutical dosage form, the optimization of manufacturing processes, and absorption in the body. Moreover, finding the most adequate polymorphic form for further drug development can reduce the time and the cost of that development.

Obtaining crystalline forms of an API is extremely useful in drug development. It permits better characterization of the drug candidate's chemical and physical properties. It is also possible to achieve desired properties of a particular API by forming a salt of the API and/or a crystalline salt of the API, Crystalline forms and crystalline salts often have better chemical and physical properties than the free base in its amorphous state. Such salts and crystalline forms may, as with the present invention, possess more favorable pharmaceutical and pharmacological properties or be easier to process than the amorphous polymorphic form. They may also have better storage stability.

One such physical property, which can affect processability, is the flowability of the solid, before and after milling, Flowability affects the ease with which the material is handled during processing into a pharmaceutical composition. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another potentially important solid state property of an API is its dissolution rate in aqueous fluid. The rate of dissolution of an active ingredient in a patient's stomach fluid may have therapeutic consequences since it impacts the rate at which an orally administered active ingredient may reach the patient's bloodstream.

By forming and/or crystallizing a salt of an API, a new solid state form of the API may have unique properties compared with existing solid forms of the API or its salt. For example, a crystalline salt may have different dissolution and solubility properties than the API itself and can be used to deliver APIs therapeutically. New drug formulations comprising crystalline salts of APIs may have superior properties over existing drug formulations.

A crystalline salt or other crystalline form of an API generally possesses distinct crystallographic and spectroscopic properties when compared to other forms having the same chemical composition. Crystallographic and spectroscopic properties of the particular form are typically measured by X-ray powder diffraction (XRPD) and single crystal X-ray crystallography, among other techniques. Particular crystalline forms often also exhibit distinct thermal behavior. Thermal behavior is measured in the laboratory by such techniques as capillary melting point, thermogravimetric analysis (TGA) and differential scanning calorimetry (DSC).

SUMMARY

The invention relates to crystalline forms of genistein, including crystalline genistein salts and a crystalline genistein hydrate. Therapeutic compositions containing the crystalline forms of genistein of the invention represent another embodiment of the invention, as do methods of treating or preventing cancer and other hyperproliferative diseases with those crystalline forms of the invention or therapeutic compositions containing them. Therapeutic compositions of crystalline genistein may also be used for the treatment or prevention of chronic inflammation, infection, cystic fibrosis and amyloidosis. As used herein and as known in the art, the term "ambient temperature" means a temperature within an enclosed space at which humans are accustomed, i.e., room temperature. For example, ambient temperature may range, for example, from about 20° C. to about 25° C.

As used herein and as known in the art, the term "approximately" means near to in quantity or amount.

As used herein and as known in the art, the term "slurry" means a suspension of solids in a liquid.

As used herein and as known in the art, the term "°2θ" is interchangeable with [degree-two-theta], [°2Th.], and variations thereof.

BRIEF DESCRIPTION OF THE DRAWINGS

The following figures, which are described below and which are incorporated in and constitute a part of the specification, illustrate exemplary embodiments according to the disclosure and are not to be considered limiting of the scope of the invention, for the invention may admit to other equally effective embodiments. The figures are not necessarily to scale, and certain features and certain views of the figures may be shown exaggerated in scale or in schematic in the interest of clarity and conciseness.

DETAILED DESCRIPTION

The current invention relates to improvements of the physiochemical properties of genistein, whereby this compound may be suitable for drug development. Disclosed herein are several new crystalline forms of genistein, including, for example, crystalline genistein salts of sodium, potassium, magnesium, N-methylglucamine (meglumine), calcium, L-lysine, N-ethylgiucamine (eglumine), and diethylamine, as well as a crystalline monohydrate of genistein. These crystalline forms of genistein are described below. Although crystalline forms of genistein are described herein, the invention also relates to novel chemical compositions containing the disclosed crystalline forms of genistein. The therapeutic uses of those crystalline forms are described as well as therapeutic compositions containing them. The methods used to characterize the crystalline forms are also described below.

One embodiment of the invention relates to a crystalline genistein sodium salt dihydrate. The crystalline genistein sodium salt dihydrate may possess suitable characteristics for pharmaceutical development. The only possible negative may be its needle-like morphology which is not necessarily ideal for flowability or compression during manufacture. The needle-like morphology was observed using Polarized Light Microscopy (PLM). Milling of this crystalline needle-like material, or similar techniques known in the art, may be used to achieve more uniform particle morphology, which may be used to prepare the material for manufacturing its pharmaceutical composition. One of ordinary skill can determine particle sizes appropriate for a desired pharmaceutical composition, Particle sizes of about 5 μm, for example; may be used. It should be noted however, that sustained milling may dehydrate the material due to the high temperatures involved during such processes. On the other hand, the 80° C. storage tests have indicated that the material can exist as a hydrate at elevated temperatures over a 7 day period with only a slight change. This mitigates the risk of dehydration on milling.

Figure 9:
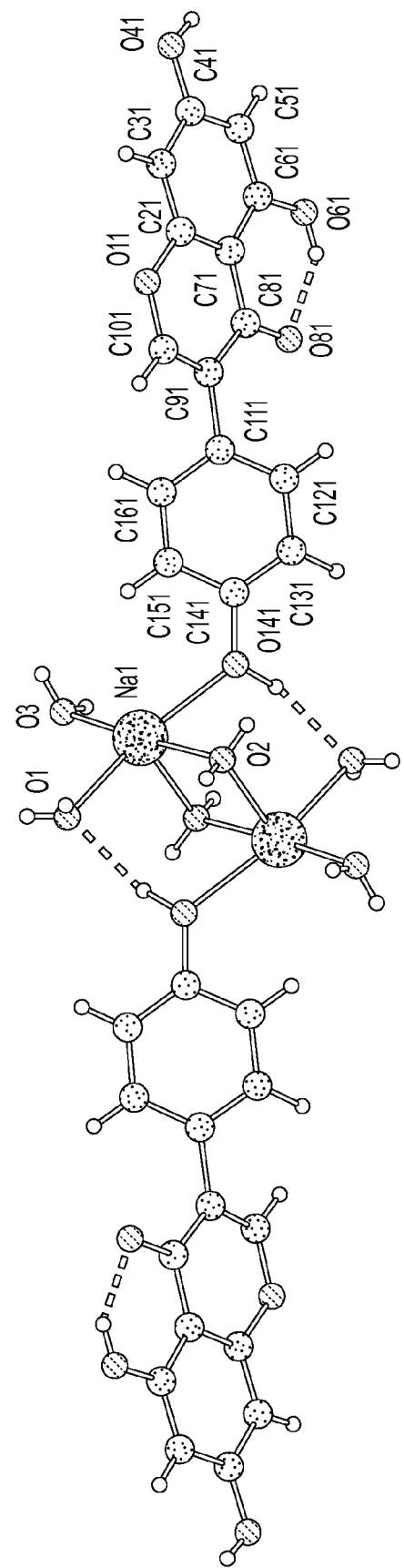
FIG. 9 is a molecular model of crystalline genistein sodium salt dihydrate, illustrating the centrosymmetric disodium cation in the dimeric structure of crystalline genistein sodium salt dihydrate, wherein the intramolecular hydrogen bonds are shown as dashed lines.

As shown in FIG. 9, the crystalline genistein sodium salt dihydrate of the invention has a dimeric structure centrosymmetric disodium cation in association with two genistein molecules and four water molecules. The crystalline genistein sodium salt dihydrate may be prepared from, for example, IPA (isopropanol or propan-2-ol), a common solvent, at ambient temperature without the need for any special treatment such as temperature cycling, sonication or rapid evaporation. As shown in Example 1 below, the crystalline genistein sodium salt dihydrate of the invention possesses excellent stability. It is more soluble in water, aqueous solvent systems and organic solvents than genistein. In addition, the crystalline genistein sodium salt dihydrate shows superior early and late intrinsic kinetic solubility profiles as compared to genistein. The crystalline genistein sodium dihydrate of the invention has also been shown to have greater bioavailability than genistein.

Another embodiment of the invention is crystalline genistein potassium salt dihydrate. The crystalline genistein potassium salt dihydrate may also be prepared from, for example, IPA (isopropanol or propan-2-ol), a common solvent, at ambient temperature without the need for any special treatment such as temperature cycling, sonication or rapid evaporation. Crystalline genistein potassium salt dihydrate readily forms from solid genistein potassium salt. Genistein potassium salt appears to be an unstable anhydrous amorphous salt at the point of recovery, which then rapidly absorbs water from the surroundings to crystallize into the dihydrated material. As discussed in Example 2 below, the crystalline genistein potassium dihydrate salt has good stability. The genistein potassium salt dihydrate is crystalline and has a needle-like morphology (but thicker needles than the corresponding crystalline genistein sodium salt dihydrate).

In addition to the crystalline sodium and potassium genistein salts of the invention, other separate embodiments of the invention relate to crystalline salts of genistein with magnesium, N-methylglucamine (meglumine), calcium, L-lysine, N-ethylglucamine (eglumine and diethylamine. A further embodiment of the invention relates to a crystalline monohydrate form of genistein. Each of these crystalline forms of genistein, their preparation and characterization, are described in the examples below, Therapeutic Uses of the Crystalline Forms of Genistein The invention relates to therapeutic uses of at least one crystalline form of genistein, for example, at least one crystalline genistein salt. The term "treatment" or "treating" means any treatment of a disease or disorder in a mammal, including, inhibiting the disease or disorder, that is, arresting or suppressing the development of clinical symptoms; and/or relieving the disease or disorder, that is, causing the regression of clinical symptoms.

The crystalline forms of genistein according to the invention may be useful as a medicament, which may be used to treat hyperproliferative diseases such as, for example, various cancers, including, for example, colorectal, gastric, esophageal, breast, lung, prostate, bladder, brain, renal, ovarian, liver, skin, thyroid, and pancreatic cancer, as well as leukemias or lymphomas. The leukemias and lymphomas mentioned herein may be tumors of myeloid lineage such as, for example, acute myeloid leukemia or of lymphoid lineage.

Additionally, the crystalline forms of genistein disclosed herein may also be used in a method of treatment of a warm-blooded animal such as, for example, man, by therapy. For example, a crystalline genistein salt according to the invention may be useful in a method of treatment of hyperproliferative diseases such as, for example, various cancers, including, for example, colorectal, gastric, esophageal, breast, lung, prostate, bladder, brain, renal, ovarian, liver, skin, thyroid, and pancreatic cancer, as well as leukemias or lymphomas. The leukemias and lymphomas mentioned herein may be tumors of myeloid lineage such as, for example, acute myeloid leukemia or of lymphoid lineage.

Moreover, crystalline forms of genistein according to the invention may be used in the method of treating a human suffering from a hyperproliferative diseases such as, for example, various cancers, including, for example, colorectal, gastric, esophageal, breast, lung, prostate, bladder, brain, renal, ovarian, liver, skin, thyroid, and pancreatic cancer, as well as leukemias or lymphomas. In another embodiment, the crystalline forms of genistein according to the disclosure may be used to prevent hyperproliferative diseases such as, for example, various cancers, including, for example, colorectal, gastric, esophageal, breast, lung, prostate, bladder, brain, renal, ovarian, liver, skin, thyroid, and pancreatic cancer, as well as leukemias or lymphomas. The leukemias and lymphomas mentioned herein may be tumors of myeloid lineage, such as, for example, acute myeloid leukemia or of lymphoid lineage, comprising the steps of administering to a person in need thereof a therapeutically effective amount of at least one crystalline form of genistein. The use of at least one crystalline form of genistein in any of the methods of treating a human described above also form aspects of this invention.

The treatment defined herein may be applied as a sole therapy or may involve, in addition to the at least one compound of the invention, conventional surgery or radiotherapy or chemotherapy. Such chemotherapy may include one or more of the following categories of anti-tumour agents: (i) antiproliferative/antineoplastic drugs and combinations thereof, as used in medical oncology, such as alkylating and alkylating like agents (for example, cis-platin, carboplatin, cyclophosphamide, nitrogen mustard, melphalan, chlorambucil, busulphan and nitrosoureas), antimetabolites (for example, gemcitabine HCl, 5-fluorouracil, tegafur, raltitrexed, methotrexate, cytosine arabinoside and hydroxyurea), antitumour antibiotics (for example, anthracyclines like adriamycin, bleomycin, doxorubicin, daunomycin, epirubicin, idarubicin, mitomycin-C, dactinomycin and mithramycin), antimitotic agents (for example, vinca alkaloids like vincristine, vinblastine, vindesine and vinorelbine and taxoids like taxol and taxotere), and topoisomerase inhibitors (for example, epipodophyllotoxins like etoposide and teniposide, amsacrine, topotecan and camptothecin); (ii) cytostatic agents, such as antioestrogens (for example, tamoxifen, toremifene, raloxifene, droloxifene and iodoxyfene), oestrogen receptor antagonists (for example fulvestrant), antiandrogens (for example, bicalutamide, flutamide, nilutamide and cyproterone acetate), LHRH antagonists or LHRH agonists (for example, goserelin, leuprorelin and buserelin), progestogens (for example, megestrol acetate), aromatase inhibitors (for example, anastrozole, letrozole, vorazole and exemestane), and inhibitors of 5-alpha-reductase (for example, finasteride); (iii) agents which inhibit cancer cell invasion (for example, metalloproteinase inhibitors like marimastat and inhibitors of urokinase plasminogen activator receptor function); (iv) inhibitors of growth factor function for example, such inhibitors include growth factor antibodies, growth factor receptor antibodies (for example, the anti-ErbB2 antibody trastuzumab (Herceptin), and the anti-ErbB1 antibody (cetuximab)), farnesyl transferase inhibitors, tyrosine kinase inhibitors, and serine-threonine kinase inhibitors, for example, inhibitors of the epidermal growth factor family (for example, EGFR family tyrosine kinase inhibitors such as N-(3-chloro-4-fluorophenyl)-7-methoxy-6-(3-morpholinopropoxy)quinazolin-4-amine (gefitinib, AZDI 839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)qumazolin-4-amine (CI 1030; inhibitors of the platelet-derived growth factor family, and inhibitors of the hepatocyte growth factor family; (v) antiangiogenic agents such as those which inhibit the effects of vascular endothelial growth factor (for example, the anti-vascular endothelial cell growth factor antibody bevacizumab (Avastin) and compounds such as those disclosed in International Patent Applications WO 97/22596, WO 97/30035, WO 97/32856 and WO 98/13354) and compounds that work by other mechanisms (for example, linomide, inhibitors of integrin function and angiostatin); (vi) vascular damaging agents such as Combretastatin A4 and compounds disclosed in International Patent Applications WO 99/02166, WO 00/40529, WO 00/41669, WO 01/92224, WO 02/04434 and WO 02/08213; (vii) antisense therapies, for example, those which are directed to the targets listed above, such as ISIS 2503, an anti-ras antisense; (viii) gene therapy approaches, including, for example, approaches to replace aberrant genes such as aberrant p53 or aberrant BRCAI BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in vivo approaches to increase the immunogenicity of patient tumour cells, such as transfection with cytokines such as interleukin 2, interleukin 4 or granulocyte-macrophage colony stimulating factor, approaches using transfected immune cells such as cytokine-transfected dendritic cells, approaches using cytokine-transfected tumor cell lines, and approaches using anti-idiotypic antibodies.

In the treatment discussed above, at least one crystalline form of genistein according to the invention may also be used in combination with one or more cell cycle inhibitors, for example, with cell cycle inhibitors which inhibit cyclin-dependent kinases (CDK), or in combination with imatinib mesylate (Glivec). Such joint treatment may be achieved by way of the simultaneous, sequential or separate dosing of the individual components of the treatment. Such combination products may employ at least one compound of this invention within the dosage range described herein and the other at least one pharmaceutically-active agent within its approved dosage range. Combination products may be formulated into a single dosage form.

The invention also provides a combination that may be suitable for use in the treatment of cell proliferative disorders (such as cancer) comprising at least one crystalline form of genistein, such as at least one crystalline genistein salt, as defined hereinbefore, and at least one additional anti-tumor agent as defined hereinbefore. Such combination may serve as a pharmaceutical product for the conjoint treatment of cell proliferative disorders (such as cancer).

In addition to their use in therapeutic medicine, at least one crystalline form of genistein according to the invention may also be useful as pharmacological tools in the development and standardization of in vitro and in vivo test systems for the evaluation of the effects of inhibitors of cell cycle activity in laboratory animals such as cats, dogs, rabbits, monkeys, rats and mice, as part of the search for new therapeutic agents.

Another aspect of invention relates to therapeutic uses of at least one crystalline form of genistein according to the invention in the preparation of a medicament for the treatment of a disease where the inhibition of inflammation is beneficial, such as, for example, chronic inflammation, inflammatory bowel disease, Crohn's disease, Sjögren's disease, rheumatoid arthritis, arthritis, atopic dermatitis, vasculitis, psoriasis, benign prostate hyperplasia, wound healing, end stage renal disease, chronic kidney disease, chronic obstructive pulmonary disease, or asthma.

Additionally, at least one crystalline form of genistein according to the invention may also be used in the preparation of a medicament for the treatment of a disease where the inhibition of infection is beneficial, such as, for example, local infection, systemic infection, sepsis, systemic fungal infection, or local fungal infection.

Yet another aspect of the invention relates to the use of at least one crystalline form of genistein for the treatment of a disease where restoring normal chloride and salt (water) movements in body organs and people's glands is beneficial, such as, for example, stimulating the cystic fibrosis transmembrane conductance regulator.

Yet another aspect of the invention relates to the use of at least one crystalline form of genistein for the treatment of a disease where inhibition of a soluble protein from forming insoluble extracellular fibril deposits causing organ dysfunction is beneficial, such as, for example, inhibition of transthyretin (TTR) amyloidoses caused by alterations in the amino acid sequence of the TTR gene product. In another embodiment of the disclosure, at least one crystalline form of genistein described herein may be used for the treatment of Familial Amyloid Polyneuropathy.

Pharmaceutical Compositions Containing Crystalline Forms of Genistein

The invention also relates to pharmaceutical compositions comprising a therapeutically effective amount of at least one crystalline form of genistein according to the invention and a pharmaceutically acceptable carrier (also known as a pharmaceutically acceptable excipient). As discussed above, the crystalline forms of genistein according to the invention may be therapeutically useful for the treatment or prevention of, for example, the disease states discussed above, including, for example, those associated with abnormal angiogenesis.

Pharmaceutical compositions for the treatment of those disease states may contain a therapeutically effective amount of at least one crystalline form of genistein according to the invention to down-regulate the transcription of genes involved in controlling angiogenesis for treatment of a patient with the particular disease. A pharmaceutical composition of the invention may be in any pharmaceutical form which contains at least one crystalline form of genistein according to the invention. The pharmaceutical composition may be, for example, a tablet, capsule, liquid suspension, injectable, topical, or transdermal. The pharmaceutical compositions generally contain, for example, about 1% to about 99% by weight of at least one crystalline form of genistein of the invention and, for example, 99% to 1% by weight of at least one suitable pharmaceutical excipient. In one embodiment, the composition may be between about 5% and about 75% by weight of at least one crystalline form of genistein of the invention with the rest being at least one suitable pharmaceutical excipient or at least one other adjuvant, as discussed below.

A "therapeutically effective amount of at least one crystalline form of genistein according to the invention" is generally in the range of about 0.05-about 500 mg/kg. The actual amount required for prophylaxis or treatment of any particular patient may depend upon a variety of factors including, for example, the disease state being treated and its severity; the specific pharmaceutical composition employed; the age, body weight, general health, sex and diet of the patient; the mode of administration; the time of administration; the route of administration; and the rate of excretion of the crystalline form of genistein; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference. The crystalline forms of genistein according to the invention and pharmaceutical compositions containing them may be used in combination with anticancer or other agents that are generally administered to a patient being treated for cancer. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. For a pharmaceutical composition of the invention, that is one having at least one crystalline form of genistein of the invention, a carrier should be chosen that maintains the crystalline form. In other words, the carrier should not substantially alter the crystalline form of genistein. Nor should the carrier be otherwise incompatible with the crystalline form of genistein salt used, such as by producing any undesirable biological effect or otherwise interacting in a deleterious manner with any other component(s) of the pharmaceutical composition.

The pharmaceutical compositions of the invention may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, at least one crystalline form of genistein may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents, and can also be of such composition that they release the active compound or compounds in a certain part of the intestinal tract in a delayed manner, Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that may be prepared by mixing at least one crystalline form of genistein according to the present disclosure with, for example, suitable non-irritating excipients or carriers such as cocoa butter, polyethyleneglycol or a suppository wax, which may be solid at ordinary temperatures but may be liquid at body temperature and, therefore, melt while in a suitable body cavity and release the active component therein.

Because the crystalline form of genistein is maintained during preparation, solid dosage forms are preferred for the pharmaceutical composition of the invention. Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier). The crystalline forms of genistein according to the invention may also be used as precursors in the formulation of liquid pharmaceutical compositions. Administration of the crystalline forms of genistein in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, intrasystemically, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

The invention also relates to preparation of a medicament using at least one crystalline form of genistein for the treatment of a variety of diseases. These include, but are not limited to: diseases where the inhibition of one or more protein tyrosine kinase(s) is beneficial, such as, for example, kinases which are affected by genistein are possible targets; hyperproliferative diseases such as various cancers, such as, for example, colorectal, breast, lung, prostate, bladder, renal or pancreatic cancer, or leukaemia or lymphoma or proliferative inflammatory atrophy; diseases where the inhibition of inflammation is beneficial, such as, for example, chronic inflammation, inflammatory bowel disease, Crohn's disease, Sjögren's disease, rheumatoid arthritis, arthritis, atopic dermatitis, vasculitis, psoriasis, benign prostate hyperplasia, wound healing, end stage renal disease, chronic kidney disease, chronic obstructive pulmonary disease, asthma; diseases where the inhibition of infection is beneficial, such as, for example local infection, systemic infection, sepsis, systemic fungal infection, local fungal infection; diseases where restoring normal chloride and salt (water) movements in body organs and glands in people is beneficial, such as, for example, stimulating the cystic fibrosis transmembrane conductance regulators as well as diseases and symptoms relating to postmenopausal condition such as hot flushes and osteoporosis as well as diseases where inhibition of a soluble protein from forming insoluble extracellular fibril deposits causing organ dysfunction is beneficial, such as amyloidosis, for example those where the fibril deposits are composed of Transthyretin (TTR), such as Familal Amyloid Polyneuropathy.

EXAMPLES

The following analytical techniques were used in the examples below:

X-Ray Powder Diffraction (XRPD):

X-ray powder diffraction studies were performed on a Bruker D8-Discover diffractometer. Approximately 5 mg of sample was gently compressed on the XRPD zero back ground single 96 well plate sample holder. The sample was then loaded into a Bruker D8-Discover diffractometer in transmission mode and analyzed using the experimental conditions shown in Table 1.

TABLE 1

| XRPD Measurement Conditions | |
|---|---|
| Raw Data Origin | BRUKER-binary V3 (.RAW) |
| Scan Axis | Gonio |
| Start Position [°2Th.] | 4.0000 |
| End Position [°2Th.] | 49.9800 |
| Step Size [°2Th.] | 0.0200 |
| Scan Step Time [s] | 39.1393 |
| Scan Type | Continuous |
| Offset [°2Th.] | 0.0000 |
| Divergence Slit Type | Fixed |
| Divergence Slit Size [°] | 2.0000 |
| Specimen Length [mm] | 10.00 |
| Receiving Slit Size [mm] | 0.1000 |
| Measurement Temperature [° C.] | 25.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 40 mA, 40 kV |
| Diffractometer Number | 0 |
| Goniometer Radius [mm] | 250.00 |
| Dist. Focus-Diverg. Slit [mm] | 91.00 |
| Incident Beam Monochromator | No |
| Spinning | No |

Differential Scanning Calorimetry (DSC):

Approximately 2 mg of sample was weighed into an aluminum DSC pan and sealed with an aluminum lid (non-hermetically). The sample pan was then loaded into a Pyris 1 Perkin-Elmer DSC (equipped with a liquid-nitrogen cooling unit) cooled and held at 25° C. Once a stable heat-flow response was obtained, the sample was then heated to 300° C. at a scan rate of 10° C./min and the resulting heat flow response monitored. A 20 cm$^3$/min helium purge was used to prevent thermally induced oxidation of the sample during heating and also to reduce the thermal lag through the sample to increase the instrument sensitivity. Prior to analysis, the instrument was temperature and heat-flow calibrated using an indium reference standard.

Gravimetric Vapor Sorption (GVS):

Approximately 15 mg of sample was placed into a wire-mesh vapor sorption balance pan and loaded into an SMS intrinsic vapor sorption balance supplied (Surface Measurement Systems Instruments). The sample was then dried by maintaining a 0% humidity environment until no further weight change was recorded. Subsequently, the sample was then subjected to a ramping profile from 0-90% RH at 10% RH increments, maintaining the sample at each step until equilibration had been attained (99.5% step completion). Upon reaching equilibration, the % RH within the apparatus was ramped to the next step and the equilibration procedure repeated. After completion of the sorption cycle, the sample was then dried using the same procedure. The weight change during the sorption/desorption cycles were then monitored, allowing for the hygroscopic nature of the sample to be determined.

Thermogravimetric Gravimetric (TGA):

Approximately 5 mg of sample was accurately weighed into a platinum TGA pan and loaded into a Perkin-Elmer TGA 7 gravimetric analyser held at room temperature. The sample was then heated at a rate of 10° C./min from 25° C. to 300° C. during which time the change in weight monitored. The purge gas used was nitrogen at a flow rate of 20 cm$^3$/min. Prior to analysis, the instrument was weight calibrated using a 100 mg reference weight and temperature calibrated using an alumel reference standard.

Polarized Light Microscopy (PLM):

The presence of crystallinity (birefringence) was determined using a Leica Leitz DMRB polarized optical microscope equipped with a high resolution Leica camera and image capture software (Firecam V.1.0). All images were recorded using 10× objectives unless otherwise stated.

$^1$H Nuclear Magnetic Resonance (NMR):

$^1$H NMR was performed on a Bruker AC200 200 MHz Spectrometer. NMR of each sample was performed in deutero-methanol. Each sample was prepared in ca. 5 mg concentration.

Example 1

Crystalline Genistein Sodium Salt Dihydrate 1.1 Preparation of Genistein Sodium Salt Dihydrate:

ca., 300 mg of genistein was placed in 6 cm$^3$ (20 vols) of IPA. On addition of 1M sodium hydroxide (NaOH) a reaction was quickly evident (color change from pale yellow to vibrant yellow). The mixture was allowed to shake at ambient temperature for ca. 3 hrs and then allowed to stand over ca. 2 days (weekend). The solid was isolated by filtration and allowed to dry at ambient temperature for ca. 24 hrs. The genistein sodium salt prepared according to this method is crystalline genistein sodium salt dihydrate which has been characterized by the following methods.

1.2 XRPD of Crystalline Genistein Sodium Salt Dihydrate

Figure 1:
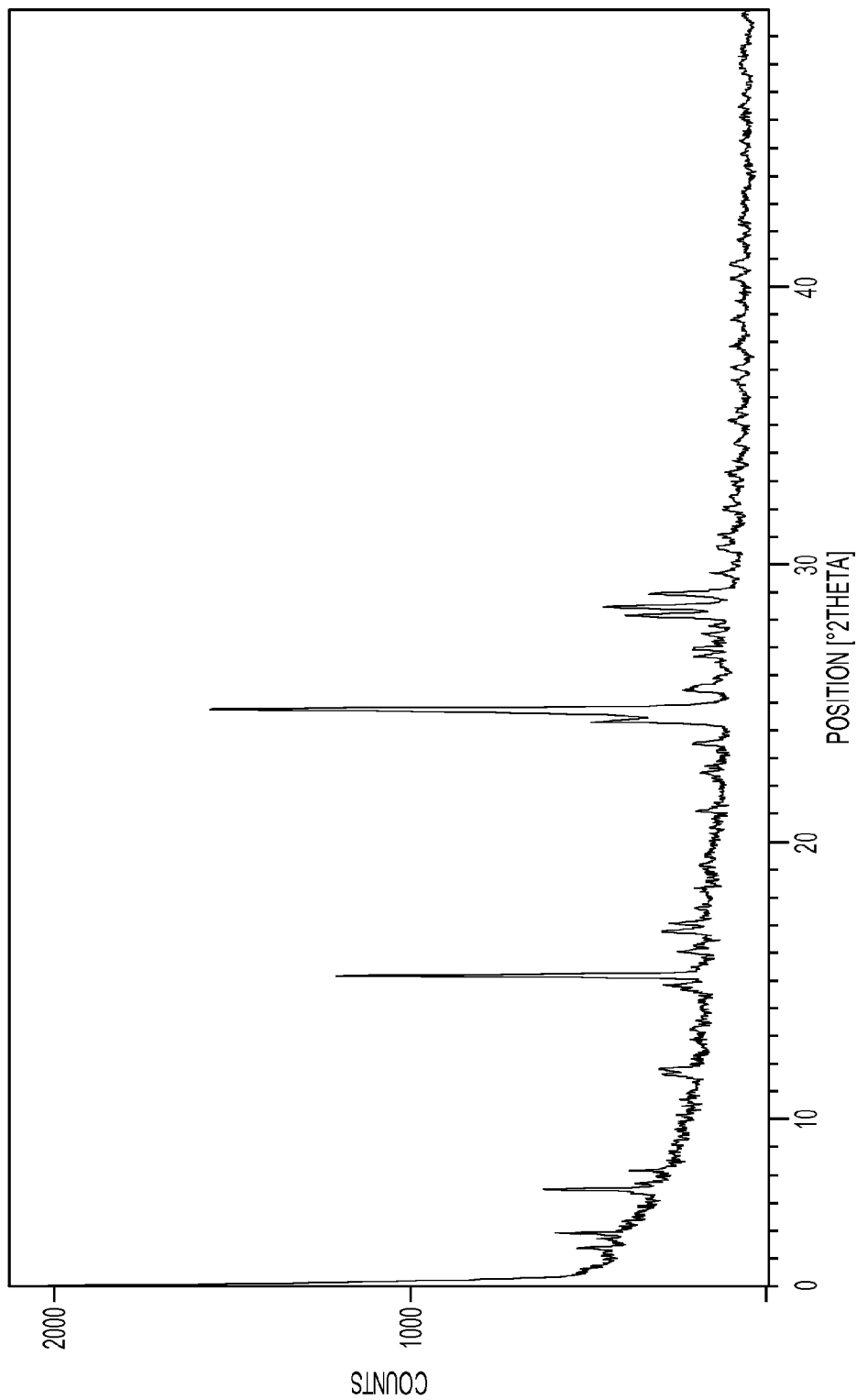
FIG. 1 depicts an XRPD pattern of crystalline genistein sodium salt dihydrate.

The XRPD pattern as shown in FIG. 1 was obtained using the procedure described above. As shown in FIG. 1, the XRPD analysis reveals a solid form impurity which is probably an IPA solvate of the sodium salt. Drying the material at 80° C. overnight removes the impurity. The peaks in the XRPD pattern at an experimental °2θ+0.2°2θ are listed in Table 2. The entire list of peaks, or a subset thereof, may be sufficient to characterize crystalline genistein sodium salt dihydrate. One subset of peaks that, individually or in combination, may be used to characterize crystalline genistein sodium salt dihydrate from FIG. 1 includes 5.9, 11.6, 11.8, 15.2, 24.8, 28.2, 28.9, and 28.9°2θ+0.2°2θ.

TABLE 2

| Pos. [°2θ ± 0.2 °2θ] | d-spacing [Å] | Rel. Int. [%] |
|---|---|---|
| 5.4 | 16.5 | 6.25 |
| 5.9 | 15.0 | 14.05 |
| 7.5 | 11.8 | 21.61 |
| 8.2 | 10.8 | 4.19 |
| 11.6 | 7.6 | 6.4 |
| 11.8 | 7.5 | 7.42 |
| 14.8 | 6.0 | 4.3 |
| 15.2 | 5.8 | 71.86 |
| 16.0 | 5.5 | 5.13 |
| 16.8 | 5.3 | 8.89 |
| 17.1 | 5.2 | 7.31 |
| 23.5 | 3.8 | 5.6 |
| 24.3 | 3.7 | 22.41 |
| 24.8 | 3.6 | 100 |
| 25.5 | 3.5 | 7.31 |
| 26.7 | 3.3 | 4.87 |
| 27.0 | 3.3 | 5 |
| 28.2 | 3.2 | 17.86 |
| 28.5 | 3.1 | 22.31 |
| 28.9 | 3.1 | 14.37 |
| 29.7 | 3.0 | 4.35 |

1.3 DSC of Dried Crystalline Genistein Sodium Salt Dihydrate

Figure 2:
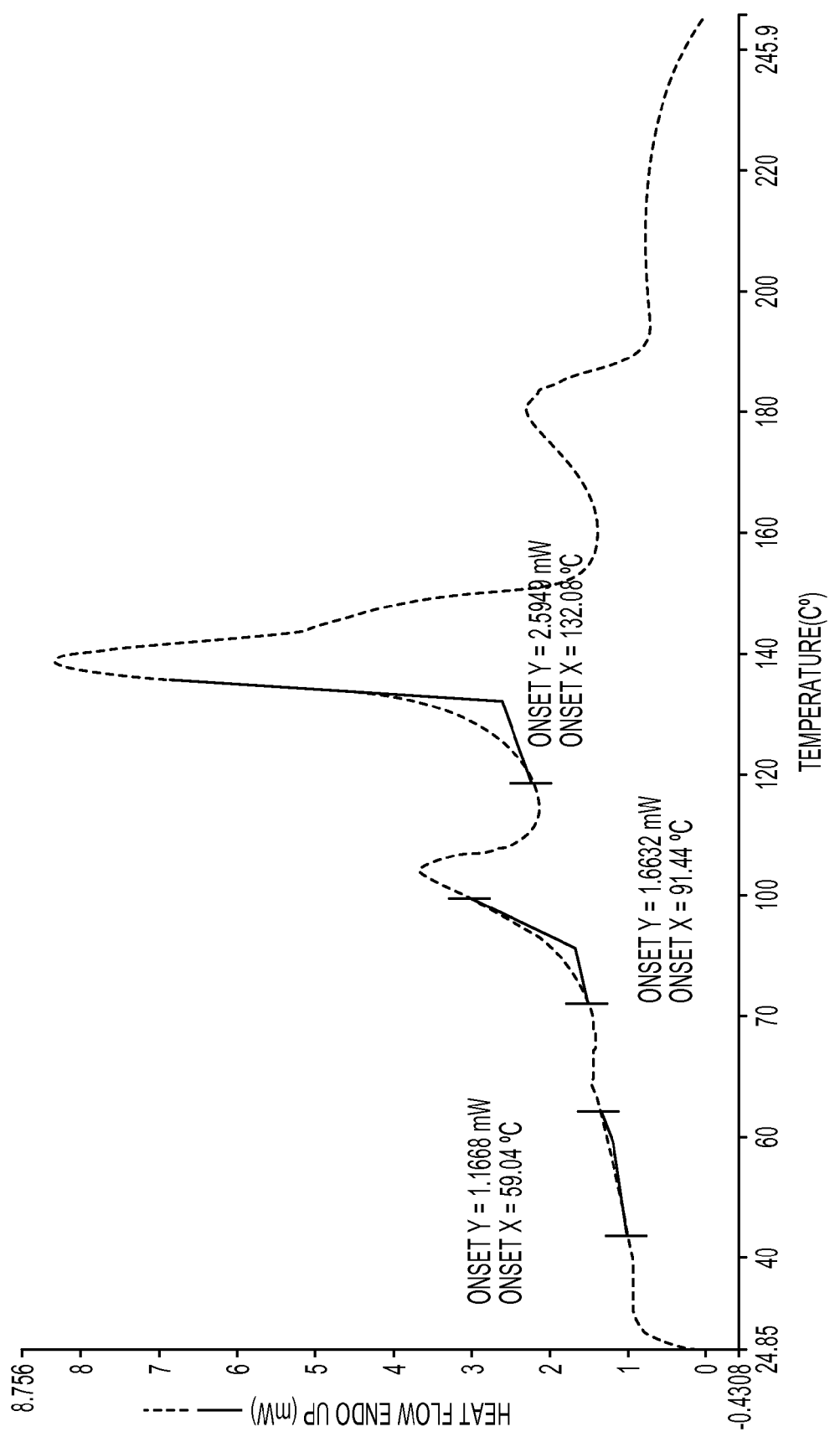
FIG. 2 depicts a DSC trace of dried crystalline genistein sodium salt dihydrate.

A sample was prepared by drying the crystalline genistein sodium dihydrate salt, prepared according to the procedure described in 1.1 above, at 80° C. overnight. FIG. 2 shows the DSC of the sample of dried crystalline genistein sodium salt dihydrate. The DSC indicates dehydration ca. 91° C. followed by melting at ca. 132° C. The other peaks are probably associated with degradation (as also indicated by the TGA traces shown in FIGS. 4 and 5, discussed below).

1.4 GVS of Crystalline Genistein Sodium Salt Dihydrate

Figure 3:
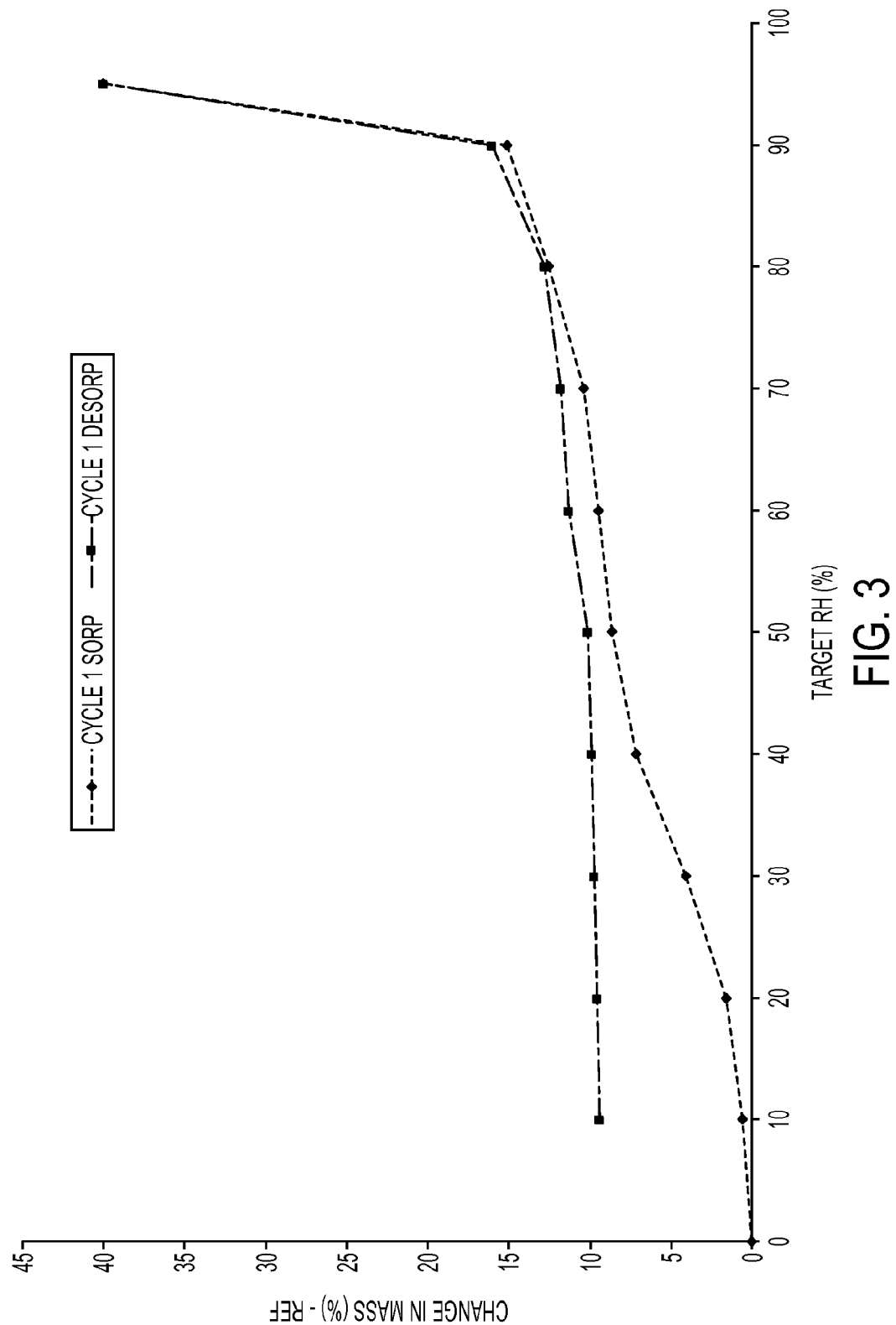
FIG. 3 depicts a gravimetric vapor sorption (GVS) trace of crystalline genistein sodium salt dihydrate.

As shown in FIG. 3, the GVS study of crystalline genistein sodium dihydrate indicated hydrate formation (GVS cycle dehydrates material prior to analysis and a maximum of 45 wt % of water adsorbed. However, between 20 and 70 RH % (typical working range of material) only ca. 2% moisture change was observed.

1.5 TGA of Crystalline Genistein Sodium Salt Dihydrate

Figure 4:
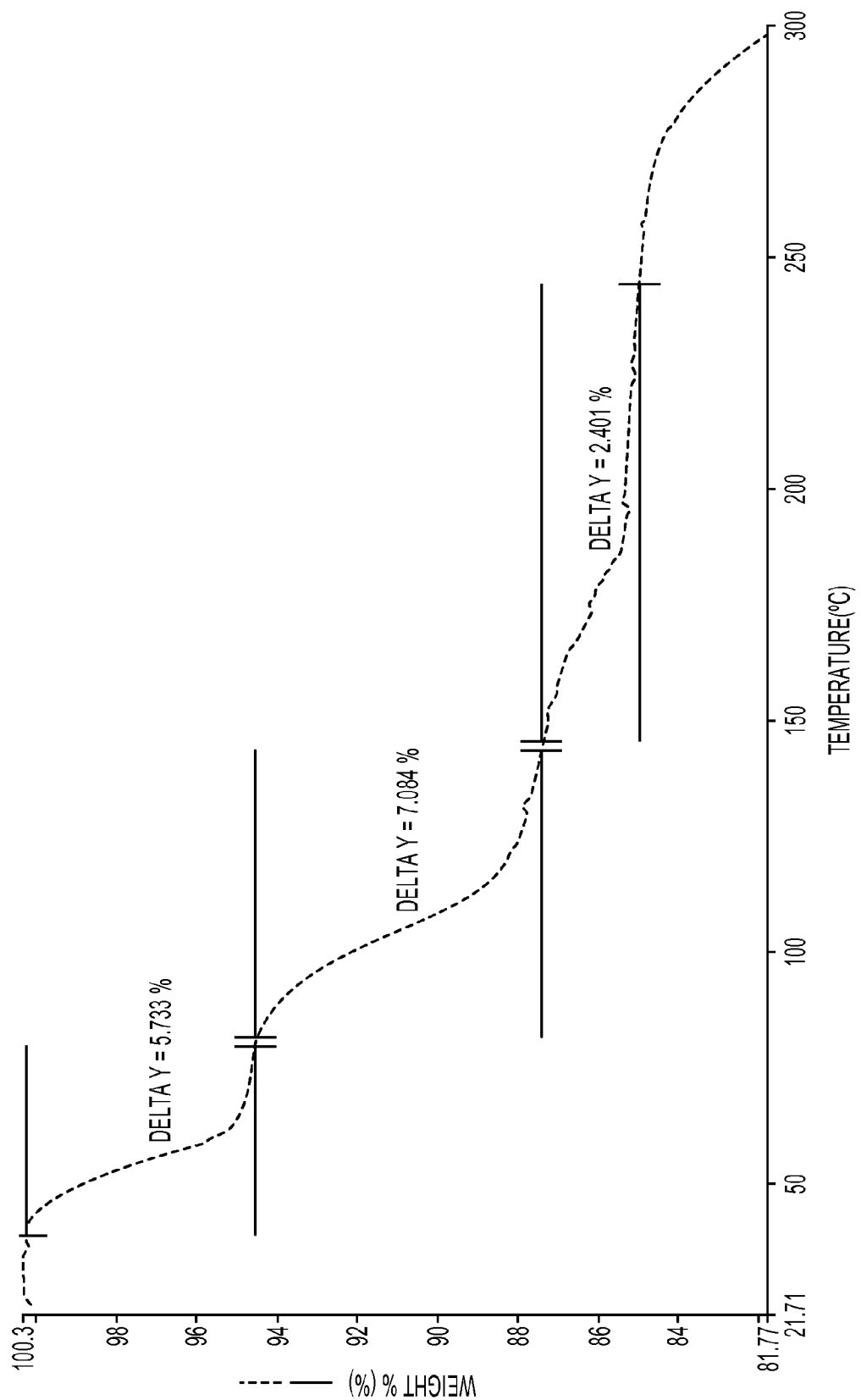
FIG. 4 depicts a TGA trace from a sample of prepared crystalline genistein sodium salt dihydrate that was dried at ambient temperature for about 24 hours.
Figure 5:
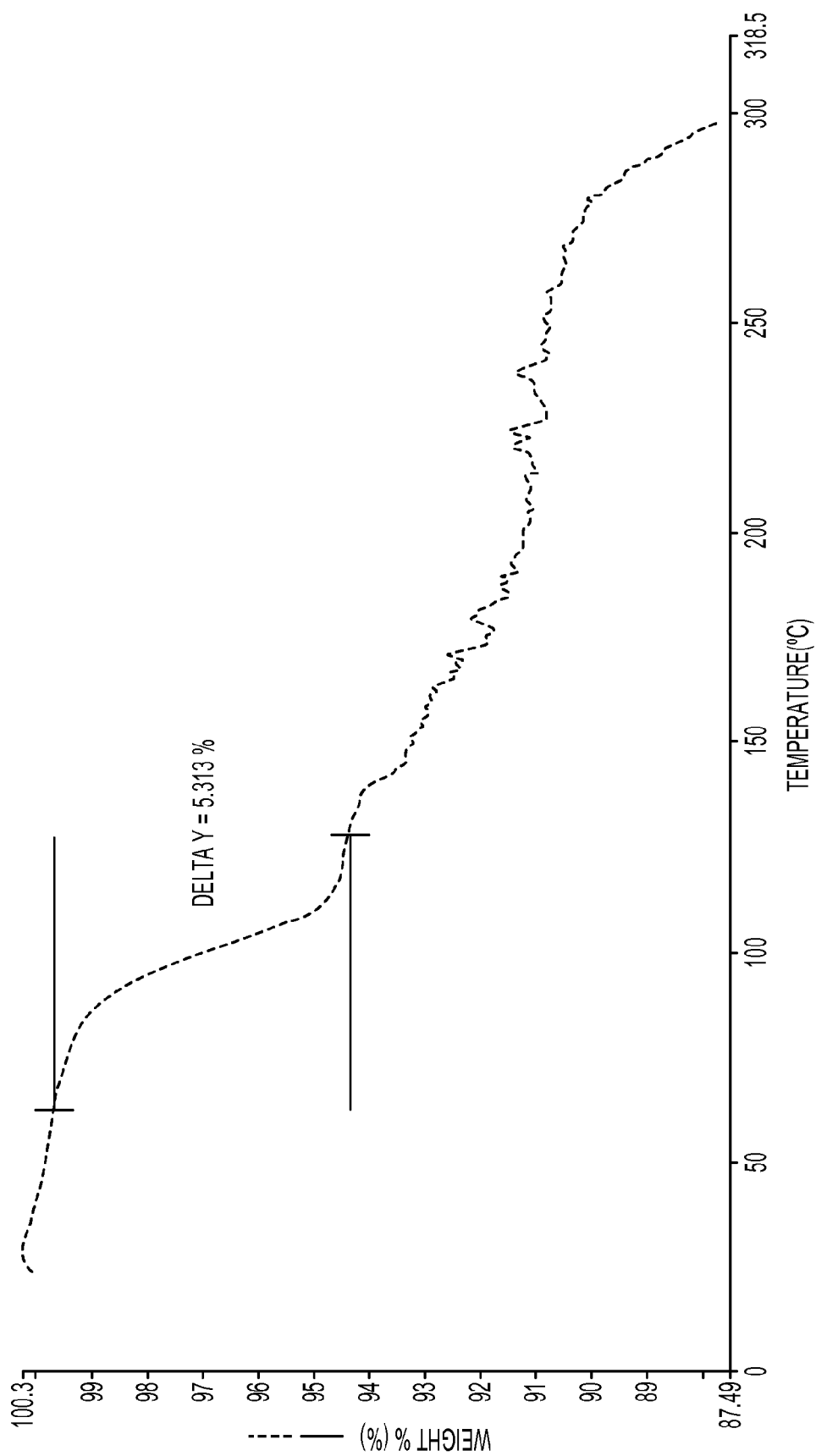
FIG. 5 depicts a TGA trace from a sample of prepared crystalline genistein sodium salt dihydrate that was dried at 80° C. overnight.

FIG. 4 shows the TGA trace from a sample of crystalline genistein sodium salt dihydrate that was dried at ambient temperature for about 24 hours, 1.1 above. FIG. 5 is a TGA from a sample of prepared crystalline genistein sodium dihydrate salt that was dried at 80° C. overnight. The TGA indicates that the sodium salt is hydrated and water loss commences at ca. 75° C., suitable for further development. The weight loss is consistent with one mole of water to one mole of sodium.

1.6 PLM of Crystalline Genistein Sodium Salt Dihydrate

The PLM of crystalline genistein sodium salt dihydrate showed a needle-like morphology.

1.7 Solubility Measurements of Crystalline Genistein Sodium Salt Dihydrate

Aqueous Solubility: Aqueous solubility was measured using the following protocol. Slurries of genistein and of crystalline genistein sodium dihydrate salt were made up in aqueous media in which pH was set at 4.5, 6.7, and 7.5, each slurry was shaken at ambient temperature for ca. 24 hours and then filtered using a 0.2 μm filter into a clean vial. The saturated solutions were then diluted and analyzed for API (genistein) content using N—Ac-DL-Methionine on a Chirobiotic T HPLC column and UV detector set at λmax=270 nm. The mobile phase was acetonitrile/water run in isocratic mode over a 30 minute period. The results are presented in Table 3, (BDL=below detection limits). No API peaks were evident from the HPLC traces run with genistein (should appear at ca. 6-7 min) indicating that genistein is extremely insoluble in aqueous media and that the levels are below the sensitivity of the HPLC technique employed (sensitivity of the technique mg to level). Genistein is reported to exhibit an aqueous solubility in the range of 10-40 nM.

TABLE 3

| Solvent | Genistein, mg/ml | Crystalline Genistein Sodium Salt Dihydrate, mg/ml |
|---|---|---|
| Water/slurry pH 4.5 | BDL | 0.136 |
| Water/slurry pH 6.7 | BDL | 0.707 |
| Water/slurry pH 7.5 | BDL | 0.650 |

Solubility in Different Solvents:

Solubility in different organic solvents was measured using the following protocol, Approximately 25 mg portions of genistein and crystalline genistein sodium dihydrate salt were placed in 48 different vials, separately, 5 volume aliquots of each solvent were added exclusively to a vial. Between each addition, the mixture was checked for dissolution and if no dissolution was apparent, the procedure was continued until dissolution was observed or when 50 volumes had been added. The results are shown in Table 4.

TABLE 4

| Solvent | Genistein Solubility, mg/ml | Crystalline Genistein Sodium Salt Dihydrate Solubility, mg/ml |
| --- | --- | --- |
| Methanol (MeOH) | <10.6 | <8.8 |
| Ethanol (EtOH) | <10.8 | 98 |
| 2-Propanol (i PA) | <10.5 | <10.2 |
| Acetone/IPA (50:50) | 20.1 | 20.2 |
| 1-Butanol (BuOH) | <10.5 | 19.3 |
| Methyl acetate (MeOAc) | <10.3 | <10.2 |
| Acetone | ca. 17 | <10.2 |
| 1,4-dioxane | <10.3 | <10.6 |
| Acetonitrile (MeCN) | <10.1 | <10.4 |
| Tetrahydrofuran (THF) | 26.3 | <10.4 |
| Dichloromethane (DCM) | <10.3 | <10.8 |
| tert-Butylmethyl ether (TBME) | <10.5 | <9.2 |
| Methylethyl ketone (MEK) | <10.8 | <9.2 |
| Heptane | <10.5 | <9.9 |
| Octanol | <10.5 | <11 |
| N-N-dimethylformamide (DMF) | ca. 100 | >217.6 |
| Dimethyl sulfoxide (DMSO) | ca. 100 | >235.2 |
| Toluene | <10.1 | <9.9 |
| N-Methyl-2-pyrrolidinone (NMP) | ca. 68 | 90.4 |
| Methyl isobutyl ketone (MIBK) | <10.1 | <9.0 |
| Acetone/Water (50:50) | <10.1 | 69.6 |
| Toluene/Dioxane (50:50) | <10.1 | <9.7 |
| Cyclohexane | <10.7 | <10.9 |
| Diisopropylether (DIPE) | <10.6 | <9.7 |

1.8 Stability Study of Crystalline Genistein Sodium Salt Dihydrate

Figure 6:
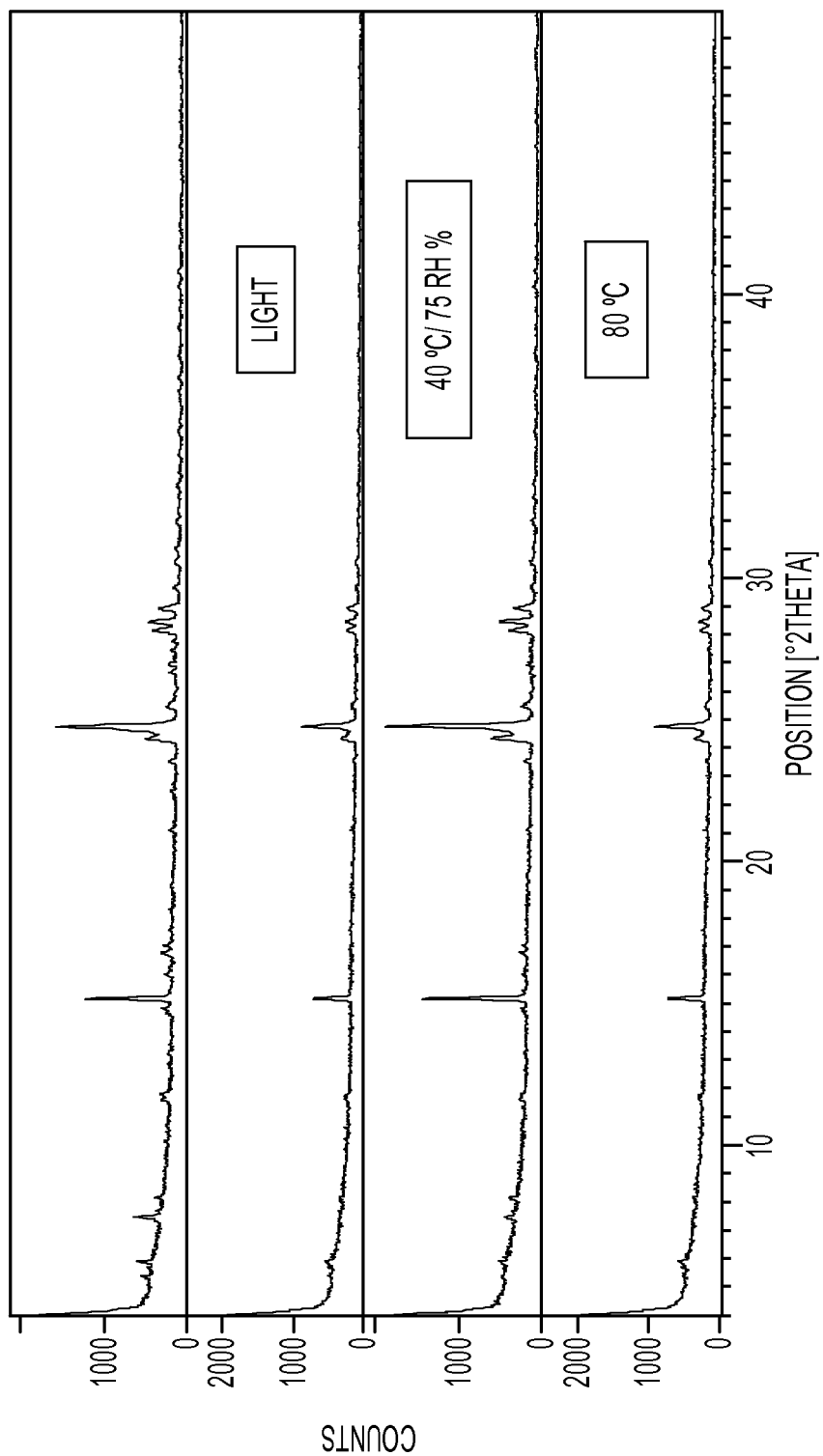
FIG. 6 depicts four XRPD patterns of crystalline genistein sodium salt dihydrate taken after stability studies at 80° C. for 7 days and at 40° C./75 relative humidity (RH) % for 7 days.

Sample stability was tested at 80° C. for 7 days and at 40° C./75 RH % for 7 days. Observations such as color change were noted after 7 days and XRPD of samples were taken after 7 days to investigate any solid form change. FIG. 6 shows the XRPD patterns of the original sample and samples of crystalline genistein sodium salt dihydrate at 80° C. for 7 days and at 40° C./75 RH % for 7 days. The 40° C./75 RH % study indicated no change over a 7 day period. Storing the material at 80° C. over a 7 day period indicated a slight loss in crystallinity suggesting slow dehydration. The 7 day light stability tests revealed no change in color or solid form.

1.9 $^1$H NMR Spectrum of Crystalline Genistein Sodium Salt Dihydrate

Figure 7:
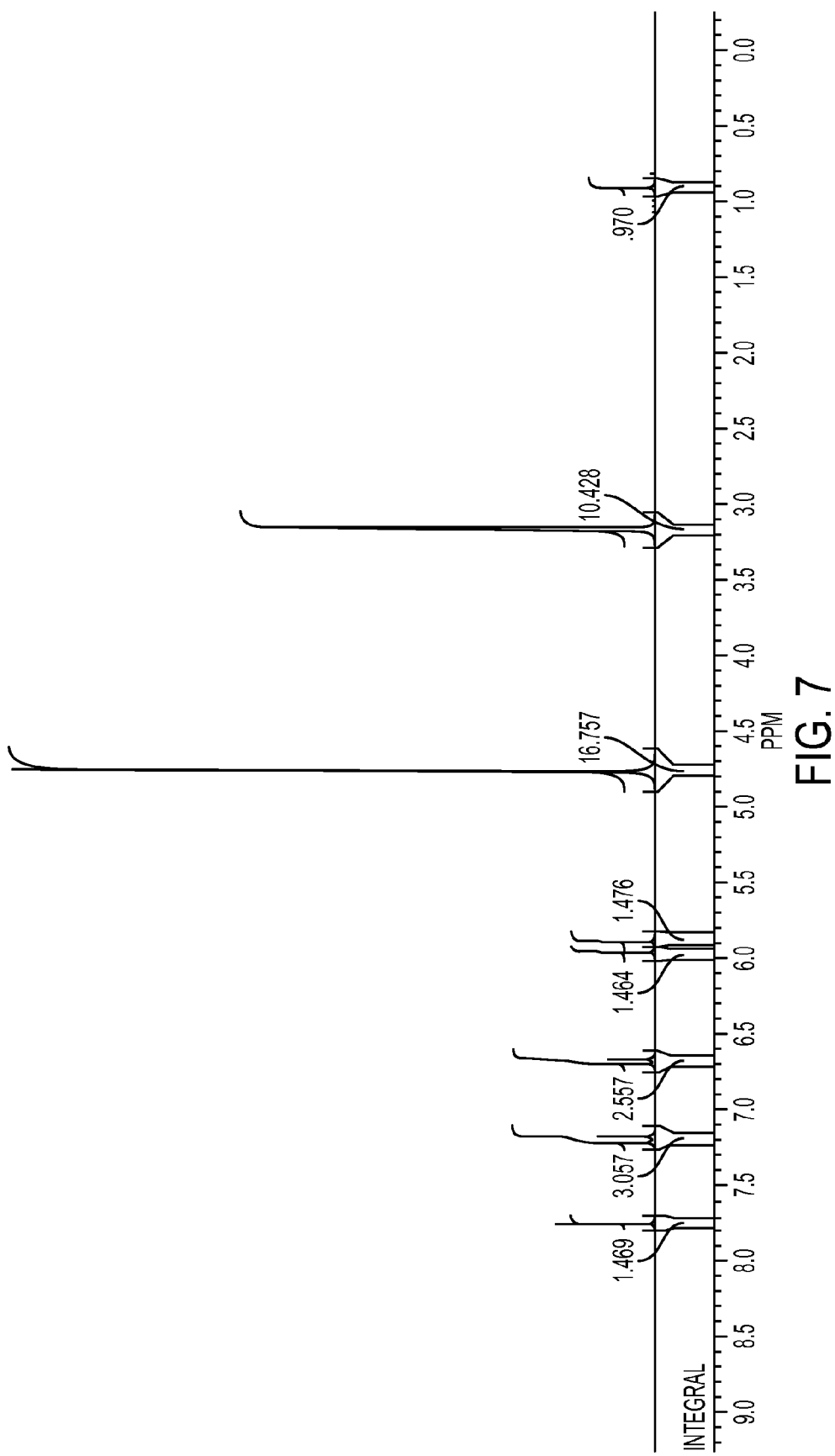
FIG. 7 is a $^1$H nuclear magnetic resonance (NMR) spectra of crystalline genistein sodium salt dihydrate.

FIG. 7 illustrates the $^1$H NMR spectrum of the crystalline genistein sodium salt dihydrate. Table 5 lists the peaks in the $^1$H NMR spectrum. Displacement of the chemical shifts for the aromatic protons at ca. 5.9 in genistein to 6.1 ppm in the $^1$H NMR of FIG. 8 confirms salt formation.

TABLE 5

| Chemical Shift | Mulitlpicity | Range (ppm) |
| --- | --- | --- |
| 7.952 | s | 7.932-7.919 |
| 7.372 | m | 7.429-7.306 |
| 6.861 | m | 6.927-6.791 |
| 6.101 | dd | 6.187-6.028 |
| 4.936 | s | 5.256-4.723 |
| 3.34 | q | 3.577-3.096 |
| 1.085 | s | 1.213-0.934 | s = singlet, m = multiplet, dd = doublet of doublet, q = quadruplet 1.10 Disproportionation Study of Crystalline Genistein Sodium Salt Dihydrate A 50 mg sample of crystalline genistein sodium salt dihydrate was slurried in 250 μl distilled water for ca, 48 hours and then checked by XRPD for disproportionation. The pH of the supernatant was also measured using a Corning 240 pH meter. No signs of disproportionation were observed. The pH of the supernatant after slurrying was 7.1.

1.11 Hydration Study of Crystalline Genistein Sodium Salt Dihydrate

Figure 8:
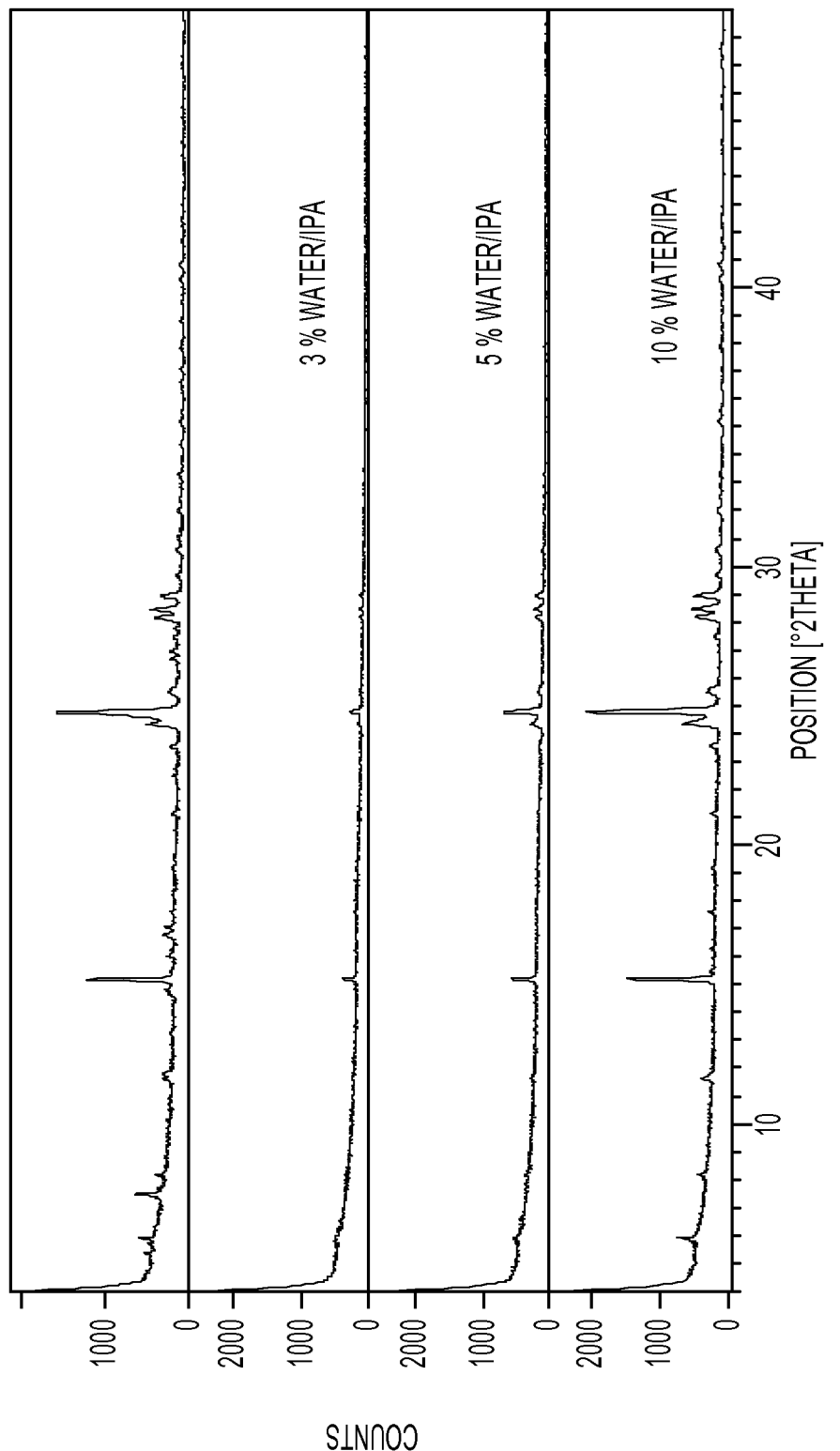
FIG. 8 depicts XRPD patterns after a hydration study of crystalline genistein sodium salt dihydrate.

Approximately 100 mg of crystalline genistein sodium salt dihydrate were placed in ca. 500 μL IPA/water mixtures (3%, 5% and 10%) at the water level. Each mixture was agitated for ca. 48 hours at ambient temperature and then filtered to recover the solid for XRPD and TGA studies. As shown in FIG. 8, hydration was indicated from a change from the original material in the XRPD pattern corresponding with weight loss from TGA (material depending). The hydration study revealed no further hydrates; but removed the IPA solvate impurity.

1.12 Single Crystal X-Ray Diffraction of Crystalline Genistein Sodium Salt Dihydrate Single Crystal Preparation:

Crystals were grown from solutions of crystalline genistein sodium salt dihydrate (ca. 48 mg) dissolved in 50:50 IPA/Water (3 cm$^3$). The solution was then allowed to slowly evaporate through pierced parafilm, Needle-like crystals were apparent after ca. 2 weeks of evaporation.

Single Crystal X-Ray Diffraction:

A lath-like needle of the sample was selected for data collection. Diffraction data were collected with Mo—Kα radiation using a Bruker Smart Apex CCD diffractometer equipped with an Oxford Cryosystems low-temperature device operating at 150 K.

On indexing the data set, the crystal structure was determined to be pseudosymmetric. Strong data could be indexed on a primitive., metrically monoclinic, cell of dimensions a=3.76, b=30.23, c=12.12 Å, β=106.2°, V=1324 Å$^3$. A complete indexing of all data could only be obtained with a larger triclinic cell of dimensions a=7.52, b=11.65, c=30.46 Å, α=89.8°, β=82.9°, γ=88.1°, V=2647 Å$^3$. This cell is itself transformable to a pseudo monoclinic C-centred cell of dimensions a=7.52, b=60.46, c=11.65 Å, β=91.9°, V 5295 Å$^3$.

The diffraction data were integrated and reduced (SAINT), and corrected for systematic errors using the multiscan procedure SADABS. The structure was solved in P-1 by direct methods (SHELXS) using the data-set integrated on the triclinic cell described above. The structure was refined against |F|$^2$ using all data (SHELXL). Incorporation of a twin law was necessary for completion of the structure. The twin law used was a two-fold rotation about the [−1 0 2] direction, which corresponds to the b-axis direction of the monoclinic cells described above.

In addition to being twinned, the structure is pseudosymmetric. This means that the atomic coordinates within the organic fragments are related to each other, and it results in correlations and mathematical instabilities into the least squares refinement. In order to overcome these similarities, restraints were applied to all chemically related bond distances and angles. Pairs of molecules (1 and 2, and 3 and 4) are related by a translation of a/2, and so equivalent anisotropic displacement parameters were constrained to be equal. Some damping was needed to achieve convergence. Correlation also causes equivalent bond lengths to become artificially different, and care should be taken not to ascribe any significance to apparent differences in chemically equivalent bond distances, for example. A more elaborate refinement model would be needed to resolve these effects.

Hydrogen atoms attached to carbon were placed in calculated positions. Some hydrogen atoms attached to oxygen could be located in difference maps. In particular, the H-atoms were attached to the O-atoms ligating the sodium ions (O141 and O144). Positions for ligand-water H-atoms were located in a Fourier map calculated about the loci of possible H-positions; those making geometrically sensible H-bonds and avoiding short contacts were included in the model, H-atoms attached to O8 were located in a difference map, and the whole molecule then initially refined as a rotating rigid group, thereafter the H-atoms were treated with a riding model. The remaining H-atoms (H7A and H142) were placed along short O . . . O vectors. There was no evidence in Fourier maps for H-atoms on O42 and O43, and attempts to place them led to the development of unreasonably short H . . . H contacts with other H-atoms.

The final 'conventional' R-factor [based on F and 7355 data with F>4σ(F)] was 0.0616. Other crystal and refinement parameters are listed in Table 6.

the problems encountered during structure analysis. That being said, the H-atom positions proposed do form a plausible H-bonding set with all H-atoms involved in geometrically normal hydrogen bonds.

As shown in FIG. 9, the cationic sodium complexes consist of dimeric units formed across inversion centres. The sodium ions are five-coordinate, the coordination sphere consisting of two terminal and two bridging water ligands and one of the LH ligands. A hydrogen bond is formed between the ligating alcohol moiety and one of the terminal water molecules (H141 . . . O1 and H141 . . . O4). The L⁻ anions are deprotonated at the phenolic O42 and O43 sites. The C—O⁻ distances

TABLE 6

Single Crystal Data and Structure Refinement for the Crystalline Genistein Sodium Salt Dihydrate.

| A. CRYSTAL DATA | |
| --- | --- |
| Empirical formula | $C_{60}H_{54}Na_2O_{28}$, $C_{30}H_{32}Na_2O_{16}$, $2(C_{15}H_9O_5)$, $2(H_2O)$ |
| Formula weight | 1269.01 |
| Wavelength | 0.71073 Å |
| Temperature | 150(2) K |
| Crystal system | Triclinic |
| Space group | P-1 |
| Unit cell dimensions | a = 7.524(2) Å alpha = 89.762(7) deg. |
| | b = 11.646(3) Å beta = 82.902(10) deg. |
| | c = 30.464(6) Å gamma = 88.073(10) deg. |
| Volume | 2647.4(12) Å³ |
| No. of reflections for cell | 7324 (2.5 < theta < 25 deg.) |
| Z | 2 |
| Density (calculated) | 1.592 Mg/m³ |
| Absorption coefficient | 0.141 mm⁻¹ |
| F(000) | 1320 |
| B. DATA COLLECTION | |
| Crystal description | colorless needle-like lath |
| Crystal size | 0.70 × 0.16 × 0.10 mm |
| Instrument | Bruker Smart Apex CCD |
| Theta range for data collection | 0.67 to 24.55 deg. |
| Index ranges | −8 <= h <= 8, −13 <= k <= 13, −35 <= l <= 35 |
| Reflections collected | 33227 |
| Independent reflections | 8758 [R(int) = 0.0574] |
| Scan type | omega |
| Absorption correction | Multiscan, (Tmin = 0.804, Tmax = 0.984) |
| C. SOLUTION AND REFINEMENT | |
| Solution | direct (SHELXS-97 (Sheldrick, 2008)) |
| Refinement type | Full-matrix least-squares on F² |
| Program used for refinement | SHELXL-97 |
| Hydrogen atom placement | geom/difmap |
| Hydrogen atom treatment | riding/rotating group |
| Data/restraints/parameters | 8758/1636/580 |
| Goodness-of-fit on F² | 1.088 |
| Conventional R [F > 4sigma(F)] | R1 = 0.0616 [7355 data] |
| Weighted R (F² and all data) | wR2 = 0.1489 |
| Final maximum delta/sigma | 0.073 |
| Weighting scheme | calc w = 1/[\s² (Fo²) + (0.0598P)² + 2.2931P] where P = (Fo² + 2Fc²)/3 |
| Largest diff. peak and hole | 0.316 and −0.310 e.Å⁻³ |

Discussion:

The single crystal structure of crystalline genistein sodium salt dihydrate shows that the compound has an overall formula of $[Na_2(H_2O)_4(\mu-H_2O)_2(LH)_2]L_2 \cdot 2H_2O$ where LH=the fully protonated genistein ligand $C_{15}H_{10}O_5$ and μ-H₂O are bridging water molecules between the Na ions (i.e., the Na ions are each bonded to two terminal waters and two bridging waters (designated μ-H₂O), plus one LH ligand—see FIG. 9). This conclusion depends on the model of H-atom placement described above. Hydrogen atom placement using X-ray data is usually regarded as tentative, the more so here because of are quite short/average 1.34 Å). An internal hydrogen bond is formed between H6* and O8* the ligating LH and the L⁻ anions.

FIG. 9 illustrates the centrosymmetric disodium cation in the dimeric structure of crystalline genistein sodium salt dihydrate, wherein the intramolecular hydrogen bonds are shown as dashed lines.

Figure 10:
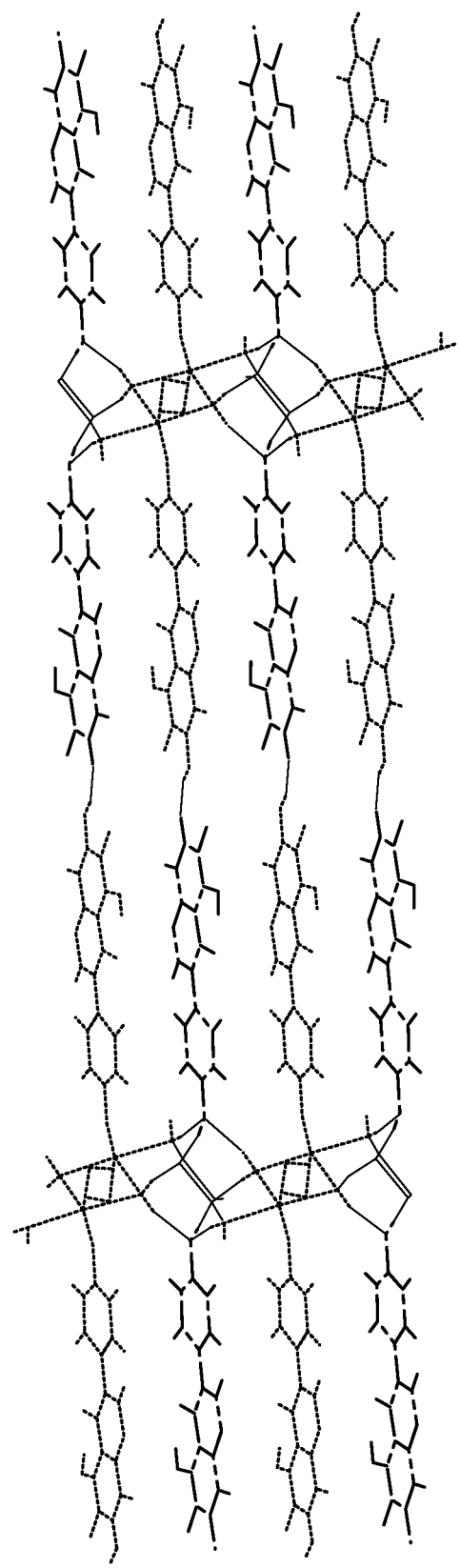
FIG. 10 is a molecular model illustrating a layer formation of crystalline genistein sodium salt dihydrate.

The packing in the crystal is dominated by hydrogen bonding. The cations are linked to the anions via water molecules to form layers which also feature stacking interactions between cations and anions. FIG. 10 shows one such layer involving cations based on O11 and anions based on O12. Water molecules are shown, in turquoise. The view is along [010].

Figure 11:
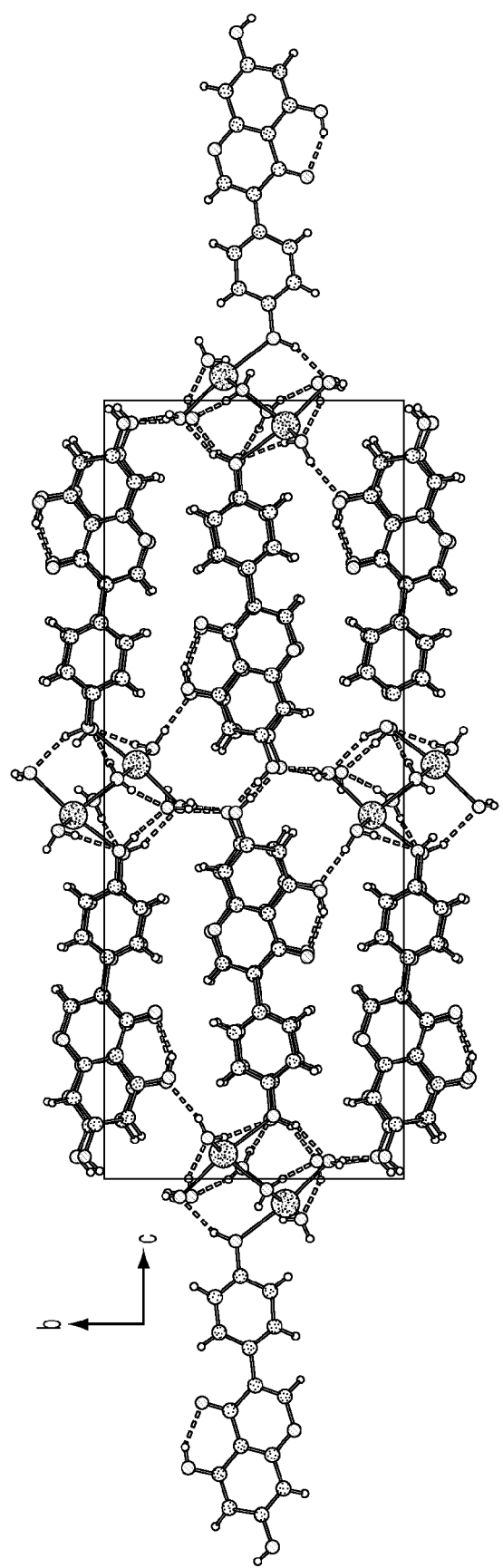
FIG. 11 is a molecular model illustrating a packing of crystalline genistein sodium salt dihydrate.

Similar layers composed of molecules based on O13 and O14 are also formed, and the two types of layers alternate along the b-axis, being linked by H-bonds. FIG. 11 illustrates the overall picture as a three dimensional network. FIG. 11 illustrates the packing of crystalline genistein sodium salt dihydrate viewed along the [100] direction.

Analysis using the PLATON/MISSYM procedure indicates that the organic fragments on their own can be described using the small (1324 Å$^3$ cell and space group P2$_1$/c, and it is only the sodium ions and water molecules which break this symmetry, explaining the pattern of strong and weak data in the diffraction pattern, and the pseudosymmetry problems experienced in refinement.

Figure 12:
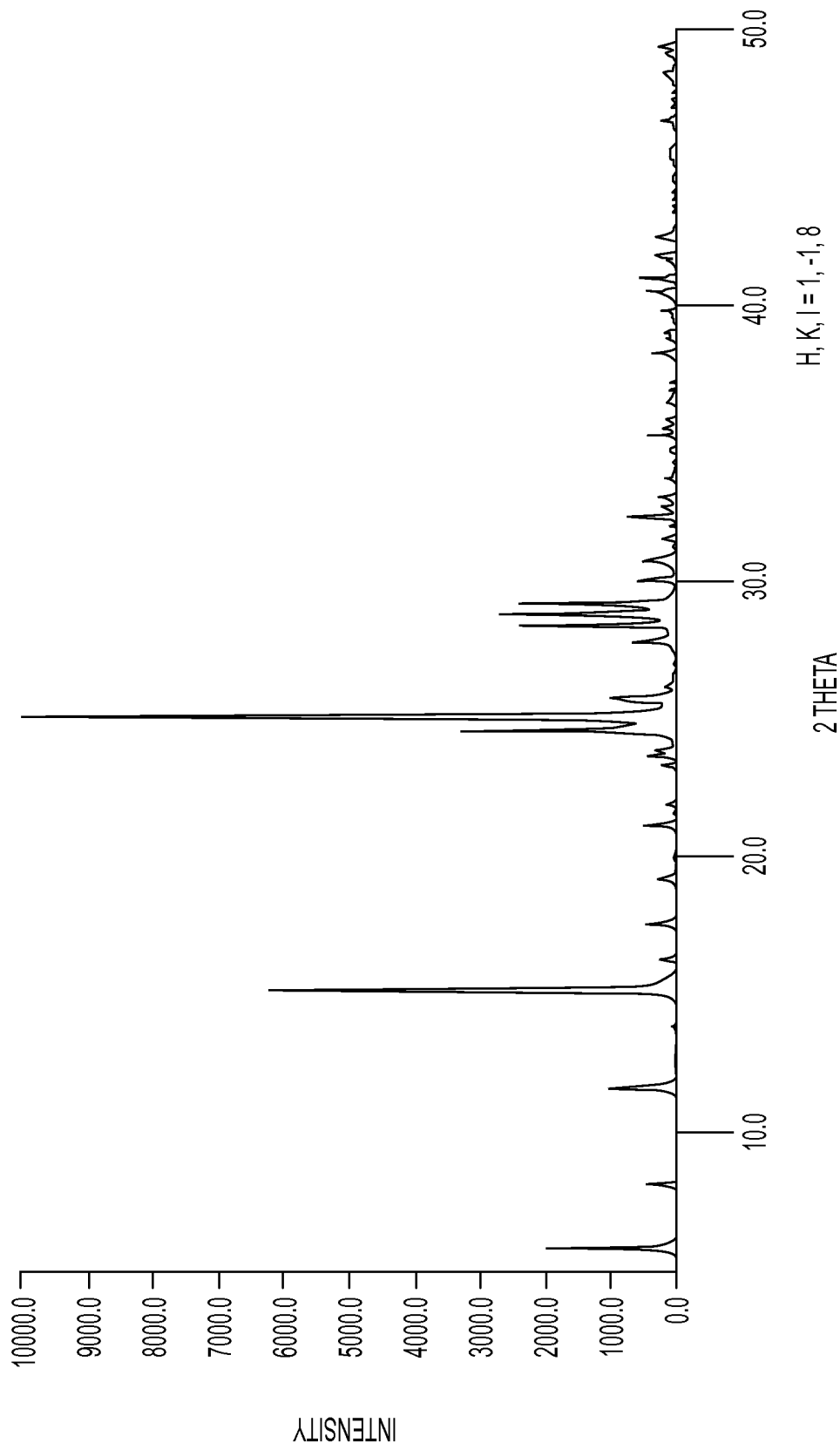
FIG. 12 depicts a calculated XRPD pattern based on single crystal data for crystalline genistein sodium salt dihydrate.

The calculated XRPD pattern based on the single crystal data and structure for the crystalline genistein sodium salt dihydrate is shown in FIG. 12. Table 7 lists the peaks in the calculated XRPD pattern. The entire list of peaks, or a subset thereof, may be sufficient to characterize crystalline genistein sodium salt dihydrate. One subset of peaks that, individually or in combination, may be used to characterize crystalline genistein sodium salt dihydrate from FIG. 12 includes 5.8, 11.6, 15.2, 17.6, 25.1, 28.4, 28.8, and 29.2°2θ±0.2°2θ.

TABLE 7

| Pos. [°2θ] | d-spacing [Å] | Rel. Int. [%] |
| --- | --- | --- |
| 5.8 | 15.1 | 23.520 |
| 8.1 | 10.9 | 5.770 |
| 11.6 | 7.6 | 12.620 |
| 15.2 | 5.8 | 69.700 |
| 17.6 | 5.0 | 5.570 |
| 23.7 | 3.8 | 4.540 |
| 24.6 | 3.6 | 35.590 |
| 25.0 | 3.6 | 32.830 |
| 25.1 | 3.6 | 97.090 |
| 25.1 | 3.6 | 98.070 |
| 25.1 | 3.5 | 100.000 |
| 25.2 | 3.5 | 73.730 |
| 25.3 | 3.5 | 14.020 |
| 25.3 | 3.5 | 9.220 |
| 25.7 | 3.5 | 7.900 |
| 25.8 | 3.5 | 10.480 |

TABLE 7-continued

| Pos. [°2θ] | d-spacing [Å] | Rel. Int. [%] |
| --- | --- | --- |
| 28.4 | 3.1 | 23.020 |
| 28.5 | 3.1 | 15.880 |
| 28.8 | 3.1 | 10.520 |
| 28.8 | 3.1 | 27.560 |
| 29.2 | 3.1 | 23.560 |
| 29.2 | 3.1 | 22.670 |
| 32.3 | 2.8 | 7.540 |

1.13 Bioavailability of Genistein Alone and From Crystalline Genistein Sodium Salt Dihydrate, Following Intraduodenal and Intravenous Administration in Male Sprague-Dawley Rats.

Preparation of Dosing Solutions for In-Vivo Study:

Genistein and Crystalline Genistein sodium salt dihydrate were stored at room temperature under desiccant and protected from light. The dosing solutions were prepared fresh from powders on the day of dosing. The dosing solution for intravenous administration (IV) was prepared at 1 mg/mL (free acid) in 50:50 DMSO:saline. The dosing solutions for intraduodenal administration (ID) were prepared at 2 mg/mL (genistein free acid) in a 0.2% sodium carboxymethyl cellulose (Na CMC) solution in water.

Animal Dosing:

The pharmacokinetics of genistein was evaluated in fasted male Sprague-Dawley rats. Each animal was fitted with a jugular vein cannula (JVC) for blood sampling. Animals intended for intravenous dosing were fitted with an additional JVC for dose administration, Animals intended for intraduodenal dosing were fitted with an intraduodenal cannula (IDC) for dose administration. Surgically modified animals were housed one per cage. All animals were supplied with a commercial rodent diet (LabDiet, Certified Rodent Diet #5002) ad libitum prior to study initiation. Food was then withheld from the animals for a minimum of twelve hours before the study and during the study, until eight hours post dose when food was returned. Water was supplied ad libitum.

Intraduodenal dosing solutions were administered as a single bolus dose at time zero on the day of dosing. Intravenous doses were administered as a slow IV injection over approximately 1 minute. Blood sampling times began at the end of the infusion. Blood samples were collected. The study design is shown in Table 8.

TABLE 8

Out-line of Comparative Pharmacokinetic Study of Genistein and Crystalline Genistein Sodium Salt Dihydrate, in Rats.

| Treatment Group | Test Compound | Dosing Route | Dose (mg/kg) | Dosing Solution Conc (mg/ml) | Dosing Volume (ml/kg) | Vehicle | Blood Sampling Time points |
| --- | --- | --- | --- | --- | --- | --- | --- |
| 1 | Genistein | ID | 20 | 10 | 2 | 0.2% NaCMC In water | Pre dose, 15, 30 min, 1, 2, 3, 4, 6, 8 and 24 h |
| 2 | Crystalline Genistein Sodium Salt Dihydrate | ID | 20 | 10 | 2 | 0.2% NaCMC In water | Pre dose, 15, 30 min, 1, 2, 3, 4, 6, 8 and 24 h |
| 3 | Genistein | IV | 1 | 1 | 1 | 50% DMSO in saline | Pre dose, 2, 5, 15, 30 min, 1, 2, 3, 4, 8 and 24 h |
| 4 | Crystalline Genistein Sodium Salt Dihydrate | IV | 1 | 1 | 1 | 50% DMSO in saline | Pre dose, 2, 5, 15, 30 min, 1, 2, 3, 4, 8 and 24 h |

Each blood sample was collected from the rats via a jugular vein cannula and placed into chilled polypropylene tubes containing sodium heparin as an anticoagulant. Samples were centrifuged at a temperature of 4"C and at a speed of 13,000 rpm for 5 minutes, Samples were maintained chilled throughout processing. Each plasma sample was split into two aliquots. The first aliquot contained 50 µl of plasma. All remaining plasma volume was used for the second aliquot. Samples were then placed on dry ice, and stored in a freezer set to maintain −60° C. to −80° C. The total concentration of genistein in plasma samples were analyzed by LC-MS/MS after an overnight incubation with glucuronidase/arylsulfatase enzyme mixture. Pharmacokinetic parameters were calculated using the WinNonlin software.

Analysis of Plasma Samples:

An LC-MS/MS analytical method for the determination of genistein in rat plasma was developed. Prior to sample analysis, a standard curve was analyzed to determine the specificity, range, and linearity of the method. Total genistein in plasma samples was determined by pre-treating all samples with β-glucuronidase/arylsulfatase enzymes and incubating prior to analysis. Incubation with the enzyme mix deconjugated any glucuronide or sulfate metabolites of genistein back to the parent form.

Acceptance Criteria for LC-MS/MS Analysis:

One standard curve was dispersed throughout each analytical run. At least ⅝ of the standards must be accurate to within ±20%, except at the LLOQ where ±25% is acceptable, in order for the run to pass.

Pharmacokinetic Analysis:

Individual plasma concentrations versus time data for genistein were subjected to non-compartmental analysis using the pharmacokinetic program WinNonlin v. 4.1. Plasma concentrations below the limit of quantitation (10 ng/mL) were assigned a value of zero for PK analysis only.

Figure 13:
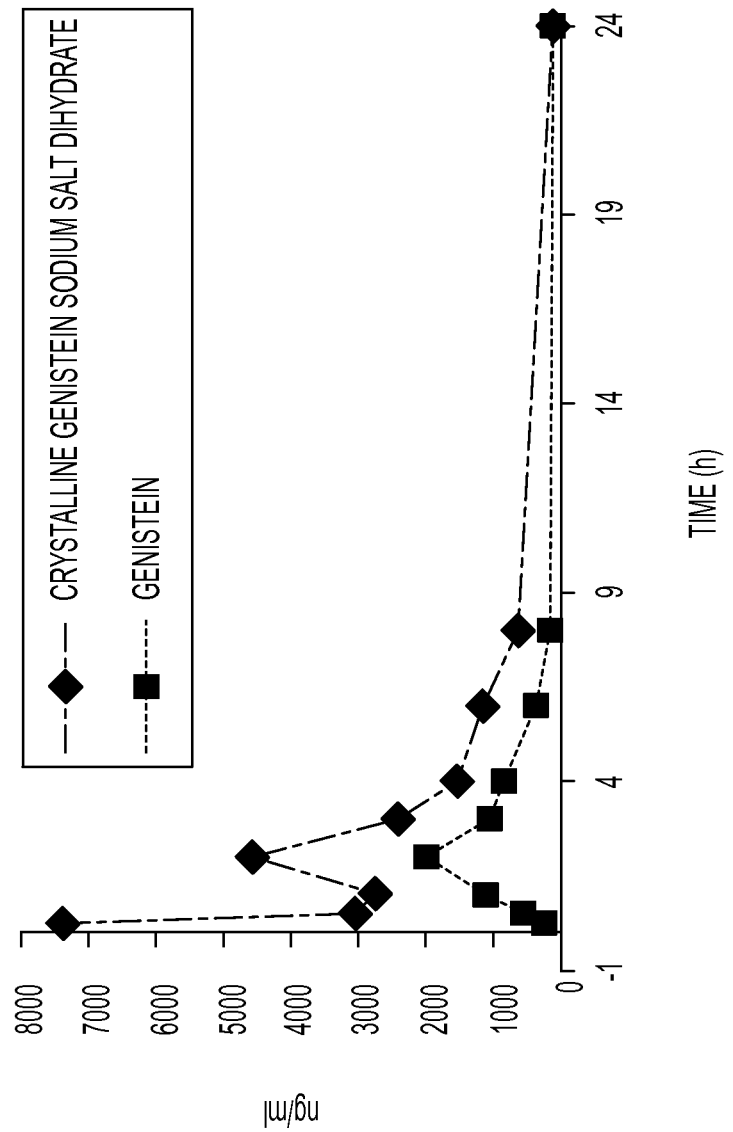
FIG. 13 depicts the plasma concentration of total genistein after intraduodenal administration of genistein and crystalline genistein sodium salt dihydrate (mean, n=3).

Results:

As shown in FIG. 13, the mean plasma concentration and PK profiles of genistein compared with crystalline genistein sodium salt dihydrate was markedly different, following ID dosing. The mean peak plasma concentration ($C_{max}$) of genistein from crystalline genistein sodium dihydrate salt was 4.2 fold higher compared to the peak plasma concentration of genistein, 8330±2176 ng/mL and 1983±1130 ng/mL, respectively. Already within 15 minutes after ID dosing of crystalline genistein sodium salt dihydrate maximum plasma concentration ($C_{max}$) of genistein was observed, while the $C_{max}$ of genistein was observed at 2 hours post dose (FIG. 13 and Table 10). The genistein bioavailability from crystalline genistein sodium salt dihydrate was 55±16% compared to 16±4.4% for genistein (Table 9).

TABLE 9

Pharmacokinetic Parameters after Intraduodenal Administration of 20 mg/kg of Respective Form (mean ± SD, n = 3).

| PK parameter | Genistein | Crystalline Genistein Sodium Salt Dihydrate |
|---|---|---|
| $C_{max}$ (ng/ml) | 1983 ± 1130 | 8330 ± 2176 |
| $t_{max}$ (H) | 2.0 ± 0 | 0.83 ± 1.0 |
| $AUC_{last}$ (h · kg · ng/ml/mg) | 414 ± 111 | 1161 ± 358 |
| Bioavailability (%) | 16 ± 4.4 | 55 ± 16 |

As shown in Table 10, the pharmacokinetic profile of genistein and crystalline genistein sodium salt dihydrate following IV dosing were not significantly different between the two forms.

TABLE 10

Pharmacokinetic Parameters after Intravenous Administration of 1 mg/kg of Respective Form (mean ± SD, n = 3).

| PK parameter | Genistein | Crystalline Genistein Sodium Salt Dihydrate |
|---|---|---|
| $C_0$ (ng/ml)[1] | 6617 ± 1059 | 6640 ± 1223 |
| $T_{1/2}$ (h) | 1.4 ± 0.3 | 1.6 ± 0.9 |
| CL (L/h/kg) | 0.40 ± 0.09 | 0.47 ± 0.08 |
| Vss (L/kg) | 0.40 ± 0.06 | 0.36 ± 0.09 |
| $AUC_{last}$ (h · kg · ng/ml/mg) | 2533 ± 638 | 2129 ± 331 |
| $AUC_{\infty}$ (h · kg · ng/ml/mg) | 2584 ± 639 | 2189 ± 356 |

[1] extrapolated to t = 0.

1.14 Physicochemical Characterization and the Kinetic and Equilibrium Solubility Comparison Between Genistein and Crystalline Genistein Sodium Salt Dihydrate.

Crystalline genistein sodium salt dihydrate shows superior early and late intrinsic kinetic solubility profiles as compared to genistein in EtOH/dH₂O solutions. The low late intrinsic kinetic solubility of crystalline genistein sodium salt dihydrate in 100% EtOH has less practical implications for the preclinical development given the non-physiological nature of the solvent.

Experimental

Genistein and crystalline genistein sodium salt dihydrate were run in a SuperSol 1000 (PREVENTOR Gmbh) solubility assay and the concentration of the compounds measured over time in a closed system by measuring the absorbance in a flow-through measuring chamber at a wavelength of 250 nm. Since both compounds form suspensions in pure deionized $H_2O$, physicochemical properties were assessed from solutions of 100% EtOH as well as mixtures of $dH_2O$ and EtOH, specifically, EtOH 50/50 (vol/vol) and EtOH 75/25 (vol/vol) according to European Pharmacopeia guidelines January 2008, Section 2.9.3., Table 2.9.3.5.

The following parameters were measured:

$t_{[MSS]}$ defined as: Time from start of analysis to Maximum Solubilization Speed (min)

$C_{[MSS]}$ defined as: Early kinetic solubility as expressed as concentration at Maximum Solubilization Speed (mg×l$^{-1}$)

$C_{[Eq]}$ defined as: Late kinetic solubility as expressed as concentration at Equilibrium Kinetic Solubility (mg×l$^{-1}$)

$\Delta t_{[Eq]}$ defined as: Time from start of analysis to Equilibrium Kinetic Solubility (min)

$\Delta C[C_{Eq}-C_{MSS}]$ defined as: Difference in concentration between Early and Late Kinetic Solubility as defined above (mg×l$^{-1}$)

$\Delta t[C_{Eq}-C_{MSS}]$ defined as: Difference in time between Early and Late Kinetic Solubility endpoints (min)

MSS defined as: Maximum Solubility Speed defined by $C_{[MSS]}/t_{[MSS]}$ (mg×l$^{-1}$×min$^{-1}$)

ISI defined as: Intrinsic Solubility Index defined by $\Delta C [C_{Eq}-C_{MSS}]/\Delta t [C_{Eq}-C_{MSS}]$ The higher the ISI value, the faster the solubilization and the stronger the relative contribution of the late, intrinsic kinetic equilibrium solubility $C_{[eq]}$.

KSR defined as: Kinetic Solubility ratio given by $C_{[MSS]}/C_{[Eq]}$.

The KSR is the numerical ratio indicator of the relative contribution of the early kinetic Solubility to the Overall Late Kinetic Equilibrium Solubility. The higher the KSR Value, the stronger the relative contribution of the early kinetic solubility $C_{[MSS]}$.

Results: The thermodynamic kinetic and equilibrium solubility data of genistein and crystalline genistein sodium salt dihydrate were assessed under the conditions reported in Tables 11, 12, and 13.

As shown in Table 11, genistein showed (a) good MSS, (b) acceptable KSR and (c) good late solubility profiles, while crystalline genistein sodium salt dihydrate showed (a) excellent MSS (b) excellent KSR and (c) good-to-acceptable ISI. For EtOH/dH$_2$O 50/50 (vol/vol) crystalline genistein sodium salt dihydrate displayed the best early intrinsic kinetic solubility profile.

TABLE 11

EtOH/dH$_2$O 50/50 (vol/vol)

| | MSS | t$_{[MSS]}$ | C$_{[MSS]}$ | C$_{[Eq]}$ | t$_{[Eq]}$ | ΔC [C$_{Eq}$ − C$_{MSS}$] | Δt [C$_{Eq}$ − C$_{MSS}$] | ISI | KSR |
|---|---|---|---|---|---|---|---|---|---|
| Genistein | 12.18 | 0:61 | 7.43 | 12.87 | 4:12 | 5.44 | 3:51 | 1.55 | 0.58 |
| Crystalline Genistein Sodium Salt Dihydrate | 20.66 | 0:71 | 14.67 | 17.40 | 5:28 | 2.73 | 4:57 | 0.60 | 0.84 |

For EtOH/dH$_2$O 75/25 (vol/vol), as shown in Table 13, genistein showed (a) good MSS, (b) good KSR and (c) good late solubility profiles. Crystalline genistein sodium salt dihydrate showed (a) excellent MSS (b) excellent KSR and (c) excellent ISI, which is the best early and late intrinsic kinetic solubility profile.

TABLE 12

EtOH/dH$_2$O 75/25 (vol/vol)

| | MSS | t$_{[MSS]}$ | C$_{[MSS]}$ | C$_{[Eq]}$ | t$_{[Eq]}$ | ΔC [C$_{Eq}$ − C$_{MSS}$] | Δt [C$_{Eq}$ − C$_{MS}$] | ISI | KSR |
|---|---|---|---|---|---|---|---|---|---|
| Genistein | 19.67 | 0:44 | 8.52 | 14.03 | 4:15 | 5.51 | 3:71 | 1.49 | 0.61 |
| Crystalline Genistein Sodium Salt Dihydrate | 37.33 | 0:30 | 11.20 | 15.86 | 4:01 | 4.66 | 3:71 | 1.26 | 0.71 |

As reported in Table 13, at EtOH 100%, genistein showed (a) good MSS, (b) acceptable KSR and (c) good late solubility profiles, while crystalline genistein sodium salt dihydrate, in comparison, showed (a) excellent MSS (b) excellent KSR and (c) poor ISI. Crystalline genistein sodium salt dihydrate showed the best early intrinsic kinetic solubility profile, but small contribution to the overall profile.

TABLE 13

EtOH 100%

| | MSS | t$_{[MSS]}$ | C$_{[MSS]}$ | C$_{[Eq]}$ | t$_{[Eq]}$ | ΔC [C, − C$_{MSS}$] | Δt [C$_{Eq}$ − C$_{MS}$] | ISI | KSR |
|---|---|---|---|---|---|---|---|---|---|
| Genistein | 23.81 | 0:24 | 5.81 | 13.79 | 4:03 | 7.98 | 3:79 | 2.11 | 0.42 |
| Crystalline Genistein Sodium Salt Dihydrate | 36.90 | 0:29 | 10.85 | 11.20 | 5:14 | 0.35 | 4:85 | 0.07 | 0.97 |

1.15 Large Scale Synthesis of Crystalline Genistein Sodium Salt Dihydrate

Synthesis:

Crystalline genistein sodium salt dihydrate was prepared on a kilogram scale using the following procedure:

1. 5.2 kg of 2-propanol (IPA) and 320 g of neutral genistein were charged into a 15 L glass reactor.
2. The temperature of the mixture was adjusted to 22±3° C. and 632 g of 2M aq. NaOH was added dropwise during about 40 minutes at 22±4° C.
3. The mixture was agitated at 22±4° C. for about 19 hours and cooled to about 15° C. and agitated for 4 hours.
4. The mixture was agitated at temperature cycles (15±3° C.→35±3° C. during 1 h→35±3° C. for 4 h→15±3° C. during 1 h→15±3° C. for 4 h) for about 90 hours and finally at 15±3° C. for about 4.5 h.
5. The precipitated product was filtered and washed with 1.2 kg of pre-cooled 2-propanol.
6. The filtered product was dried in vacuum tray dryer without vacuum at first at the set temperature of 30° C. for about 19 h, then at the set temperature of 40° C. for about 20 h, then at the set temperature of 50° C. for about 24 h, then at the set temperature of 60° C. for about 16 h and finally at set temperature of 70° C. for about 10 h until the water content measured by KF-titration met set specification.
7. Finally, the product (0.24 kg) was ground and packed into PE-bags.

Optional Recrystallization Procedure

Crystalline genistein sodium salt dihydrate was recrystallized using the following procedure:
1. 24 g of the crystalline genistein sodium salt dihydrate prepared as above was added to 240 ml of ethanol.
2. This mixture was stirred at 250 rpm and heat at 45° C., for ca. 30 mins.
3. The resulting solution was allowed to cool to room temperature.
4. Heptane was then added in aliquots (detailed as follows) adding 1 aliquot per 1 min. Intermittent stirring at 40 rpm was used between each addition.
   Added 4.151 ml of heptane and stirred intermittently at 40 rpm.
   Added 3.272 ml of heptane and stirred intermittently at 40 rpm.
   Added 5.209 ml of heptane and stirred intermittently at 40 rpm.
   Added 3.505 ml of heptane and stirred intermittently at 40 rpm.
   Added 3.885 ml of heptane and stirred intermittently at 40 rpm.
   Added 5.465 ml of heptane and stirred intermittently at 40 rpm.
   Added 6.314 ml of heptane and stirred intermittently at 40 rpm.
   Added 6.656 ml of heptane and stirred intermittently at 40 rpm.
   Added 8.258 ml of heptane and stirred intermittently at 40 rpm.
   Added 6.969 ml of heptane and stirred intermittently at 40 rpm.
   Added 11.115 ml of heptane and stirred intermittently at 40 rpm.
   Added 10.750 ml of heptane and stirred intermittently at 40 rpm.
   Added 14.219 ml of heptane and stirred intermittently at 40 rpm.
   Added 9.261 ml of heptane and stirred intermittently at 40 rpm.
   Added 14.913 ml of heptane and stirred intermittently at 40 rpm.
   Added 13.471 ml of heptane and stirred intermittently at 40 rpm.
   Added 15.753 ml of heptane and stirred intermittently at 40 rpm.
   Added 19.172 ml of heptane and stirred intermittently at 40 rpm.
   Added 23.441 ml of heptane and stirred intermittently at 40 rpm.
   Added 25.503 ml of heptane and stirred intermittently at 40 rpm.
   Added 26.856 ml of heptane and stirred intermittently at 40 rpm.
   Added 28.126 ml of heptane and stirred intermittently at 40 rpm.
   Added 28.070 ml of heptane and stirred intermittently at 40 rpm.
   Added 36.738 ml of heptane and stirred intermittently at 40 rpm.
   Added 35.989 ml of heptane and stirred intermittently at 40 rpm.
   Added 49.677 ml of heptane and stirred intermittently at 40 rpm.
   Added 50.145 ml of heptane and stirred intermittently at 40 rpm.
   Added 32.579 ml of heptane and stirred intermittently at 40 rpm.
   Added 61.538 ml of heptane and stirred intermittently at 40 rpm.
   Added 57.143 ml of heptane and stirred intermittently at 40 rpm.
   Added 51.948 ml of heptane and stirred intermittently at 40 rpm.
   Added 90.909 ml of heptane and stirred intermittently at 40 rpm.
5. The sample was then left to crystallise overnight at room temperature (ca. 18 hrs).
6. The crystalline product was collected by vacuum filtration,
7. The crystalline product was then dried for ca. 21 hours while monitoring the water content by Karl Fischer titration to avoid the risk of dehydration.

Figure 14:
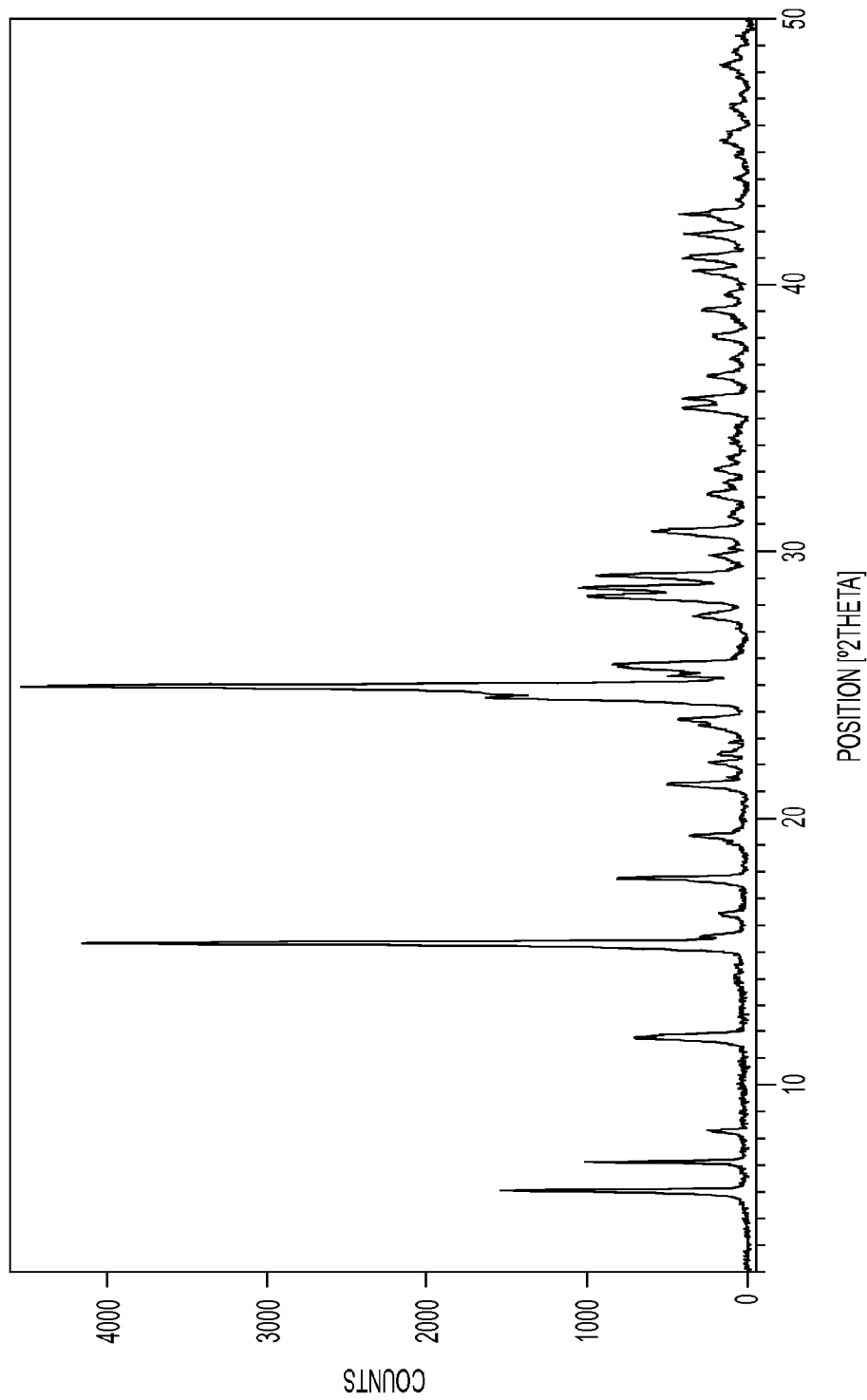
FIG. 14 depicts an XRPD pattern for crystalline genistein sodium salt dihydrate from the large scale synthesis.

FIG. 14 shows the XRPD pattern of the recrystallized crystalline genistein sodium salt dihydrate. The peaks in the XRPD pattern at an experimental °2θ±0.2°2θ are listed in Table 14. The entire list of peaks, or a subset thereof, may be sufficient to characterize crystalline genistein sodium salt dihydrate. One subset of peaks that, individually or in combination, may be used to characterize crystalline genistein sodium salt dihydrate from FIG. 14 includes 6.0, 7.1, 11.8, 11.9, 15.3, 17.8, 21.3, 25.0, 28.3, 28.6, and 29.1°2θ±0.2°2θ. Preferred subset of peaks include 6.0, 7.1, 15.3, 25.0 and at least two of the three peaks 28.3, 28.6, and 29.1°2θ±0.2°2θ and 6.0, 7.1, 15.3, 25.0 and 28.3°2θ±0.2°2θ.

TABLE 14

| Pos. [°2θ ± 0.2 °2θ] | d-spacing [Å] | Rel. Int. [%] |
| --- | --- | --- |
| 6.0 | 14.6 | 33.53 |
| 7.1 | 12.4 | 21.77 |
| 8.3 | 10.7 | 5.53 |
| 11.8 | 7.5 | 15.05 |
| 11.9 | 7.4 | 12.04 |
| 15.3 | 5.8 | 90.11 |
| 15.6 | 5.7 | 5.91 |
| 17.8 | 5.0 | 17.38 |
| 19.3 | 4.6 | 7.99 |
| 21.3 | 4.2 | 10.78 |
| 22.1 | 4.0 | 4.67 |
| 23.4 | 3.8 | 5.61 |
| 23.7 | 3.8 | 9.49 |
| 24.5 | 3.6 | 35.37 |
| 25.0 | 3.6 | 100 |
| 25.4 | 3.5 | 9.09 |
| 25.6 | 3.5 | 16.02 |
| 25.8 | 3.5 | 18.24 |
| 27.6 | 3.2 | 6.76 |
| 28.3 | 3.2 | 21.60 |
| 28.6 | 3.1 | 22.15 |
| 29.1 | 3.1 | 20.45 |
| 29.9 | 3.0 | 5.12 |
| 30.7 | 2.9 | 12.80 |
| 30.8 | 2.9 | 9.80 |
| 32.1 | 2.8 | 5.32 |
| 35.4 | 2.5 | 8.63 |
| 35.7 | 2.5 | 8.78 |
| 36.6 | 2.5 | 5.38 |
| 39.1 | 2.3 | 5.66 |
| 40.5 | 2.2 | 6.66 |
| 41.0 | 2.2 | 8.72 |
| 41.1 | 2.2 | 7.29 |

TABLE 14-continued

| Pos. [°2θ ± 0.2 °2θ] | d-spacing [Å] | Rel. Int. [%] |
|---|---|---|
| 41.9 | 2.2 | 8.62 |
| 42.6 | 2.1 | 8.97 |

Example 2

Crystalline Genistein Potassium Salt Dihydrate 2.1 Preparation of Genistein Potassium Salt:

ca., 300 mg of genistein was placed in 6 cm$^3$ (20 vols) of IPA, On addition of 1M potassium hydroxide (KOH) a reaction of the slurry was evident (i.e., slurry to clear solution). The mixture was allowed to shake at ambient temperature for ca. 3 hrs during which time precipitation was evident. The mixture was then allowed to stand at ambient temperature for ca. 2 days (weekend). The solid was isolated by filtration and allowed to dry at ambient temperature for ca. 24 hrs.

Crystalline genistein potassium salt dihydrate forms from the amorphous potassium salt upon standing when open to air under ambient room conditions. It may also be prepared from the amorphous potassium salt when the genistein potassium salt is slurried in IPA/water mixture as described in the hydration studies to form crystalline genistein potassium salt dihydrate by water uptake.

Genistein potassium salt, thus, appears to be an unstable anhydrous amorphous salt at the point of recovery, which then rapidly absorbs water from the surroundings to crystallize into a dihydrated material. This finding is supported by the light stability test; the hydration study; the 40° C./75 RH % study; the 80° C. storage study and the TGA test—all described below. The 80° C. storage study is particularly notable as the material appears to be absorbing water at this elevated temperature; thus, suggesting that the hydrate is stable at 80° C. The GVS data also indicates that the genistein potassium salt dihydrate is the most stable version and therefore developable. Although the synthetic procedure described above does not yield the dihydrate material directly, it may well be produced by further processing or changing the solvent system to include a higher water content, (i.e., 3% water/IPA), Like the crystalline genistein sodium salt dihydrate, the risk of dehydration in milling is somewhat mitigated by the 80° C. storage tests.

2.2 XRPD of the Amorphous Genistein Potassium Salt

Figure 15:
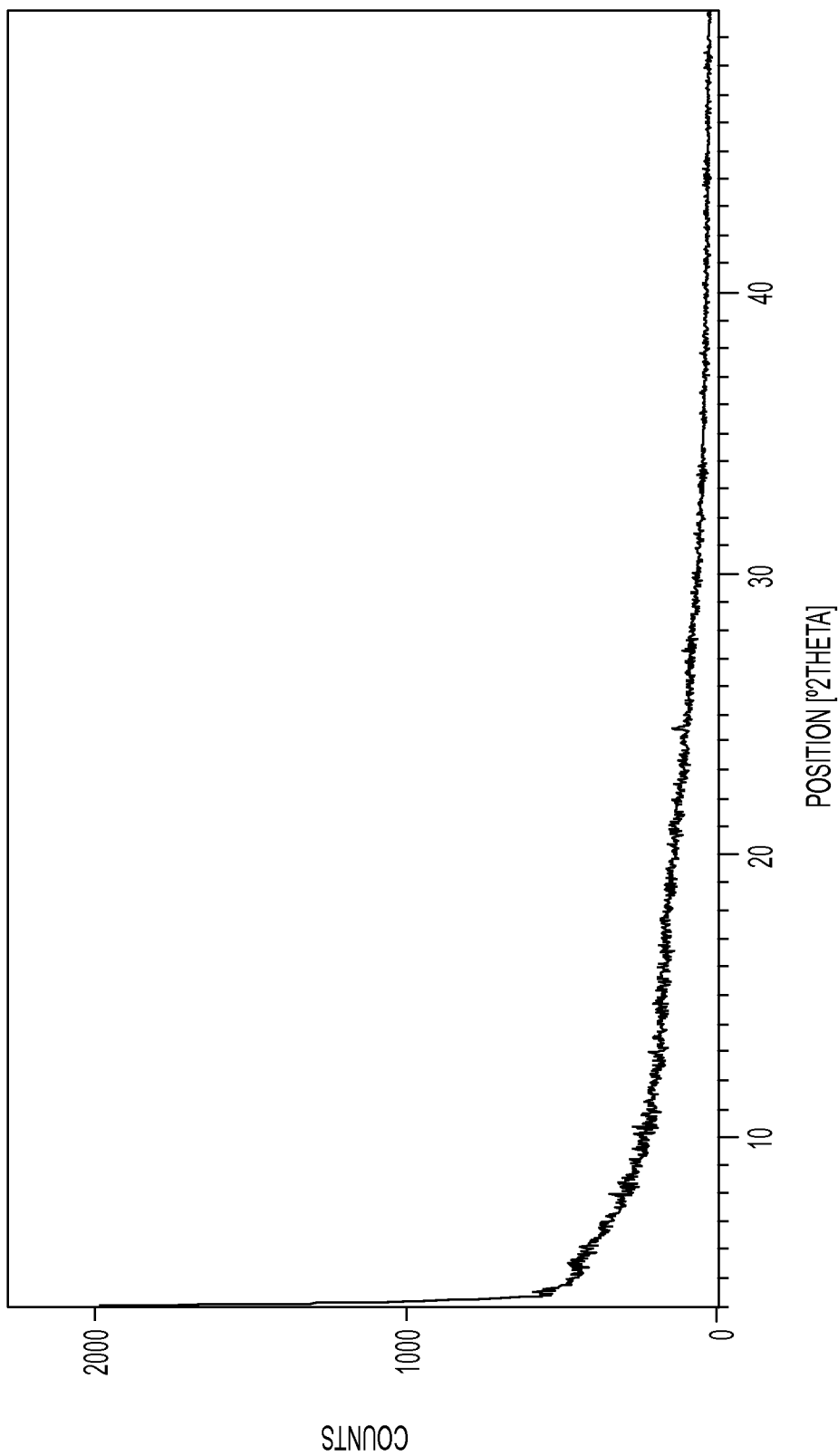
FIG. 15 depicts an XRPD pattern for amorphous genistein potassium salt.

As shown in FIG. 15, the XRPD analysis reveals the solid genistein potassium salt produced as described in 2.1 is amorphous (i.e., no peaks).

2.3 XRPD of the Crystalline Genistein Potassium Salt Dihydrate

Figure 16:
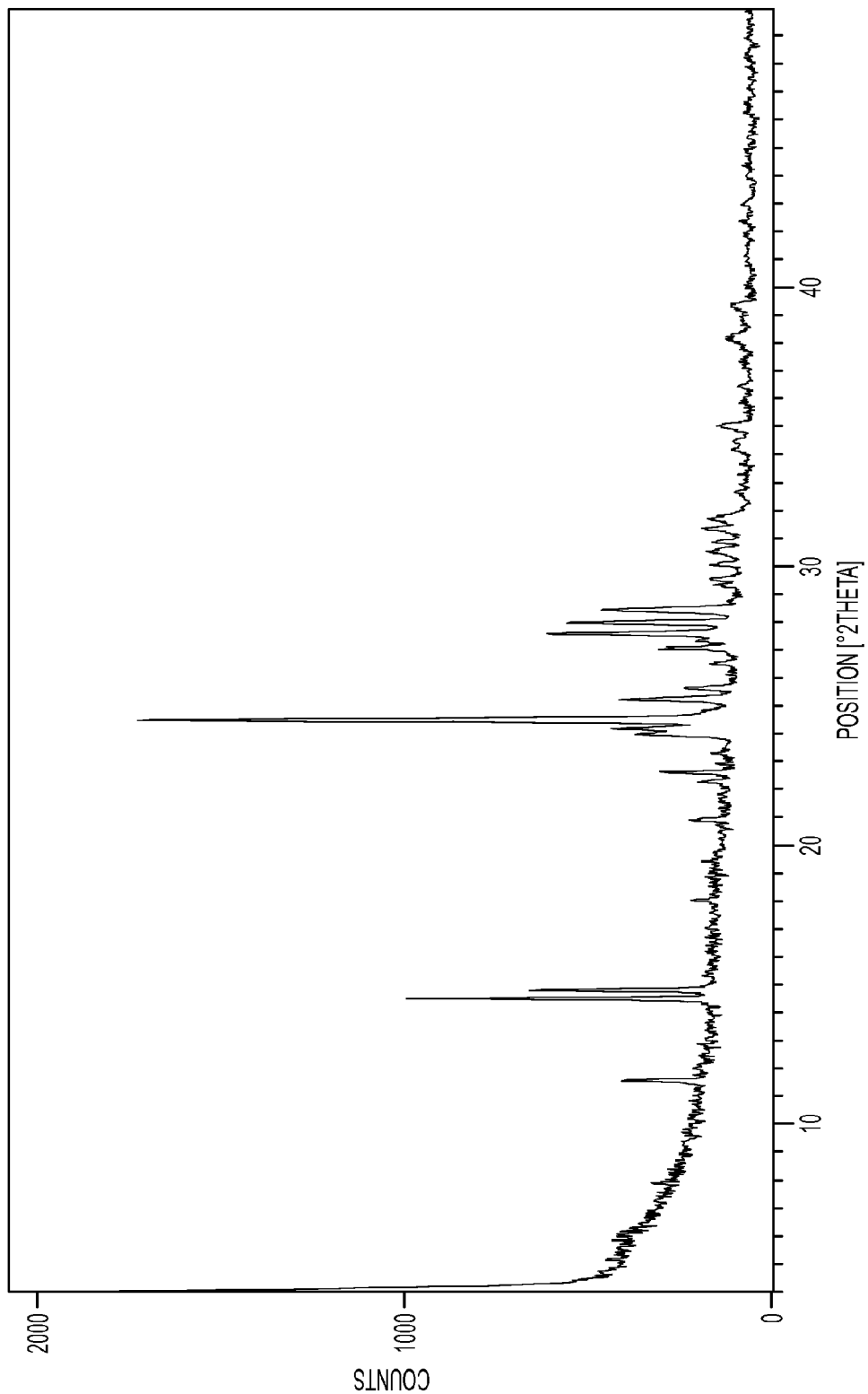
FIG. 16 depicts an XRPD pattern for crystalline genistein potassium salt dihydrate.

FIG. 16 shows the XRPD pattern of the crystalline genistein potassium salt dihydrate. The peaks in the XRPD pattern at an experimental °2θ±0.2°2θ are listed in Table 15. The entire list of peaks, or a subset thereof, may be sufficient to characterize crystalline genistein potassium salt dihydrate. One subset of peaks that, individually or in combination, may be used to characterize crystalline genistein potassium salt dihydrate from FIG. 16 includes 11.6, 14.5, 14.8, 24.5, 25.2, 27.6, 28.0, and 28.4°2θ±0.2°2θ. A preferred subset of peaks includes 11.6, 14.5, 24.5, 25.2 and at least two of the three peaks 27.6, 28.0, and 28.4°2θ±0.2°2θ.

TABLE 15

| Pos. [°2θ ± 0.2 °2θ] | d-spacing [Å] | Rel. Int. [%] |
|---|---|---|
| 11.6 | 7.6 | 12.95 |
| 14.5 | 6.1 | 51.58 |
| 14.8 | 6.0 | 30.96 |
| 18.0 | 4.9 | 4.42 |
| 22.3 | 4.0 | 4.25 |
| 22.6 | 3.9 | 11.47 |
| 24.0 | 3.7 | 15.84 |
| 24.2 | 3.7 | 20.16 |
| 24.5 | 3.6 | 100 |
| 25.2 | 3.5 | 19.35 |
| 25.6 | 3.5 | 8.28 |
| 27.0 | 3.3 | 11.63 |
| 27.1 | 3.3 | 12.14 |
| 27.6 | 3.2 | 31.86 |
| 28.0 | 3.2 | 29 |
| 28.4 | 3.1 | 23.21 |
| 29.3 | 3.0 | 4.53 |
| 29.5 | 3.0 | 4.67 |
| 30.0 | 3.0 | 5.34 |
| 30.5 | 2.9 | 5.25 |
| 30.9 | 2.9 | 4.46 |
| 31.3 | 2.9 | 6.03 |
| 31.7 | 2.8 | 5.5 |
| 35.0 | 2.6 | 4.76 |

2.4 PLM of Crystalline Genistein Potassium Salt Dihydrate

PLM analysis of genistein potassium salt dihydrate showed that the potassium salt is crystalline and has a needle-like morphology. The needles are thicker than those of the crystalline genistein sodium salt dihydrate.

2.5 TGA of Crystalline Genistein Potassium Salt Dihydrate

Figure 17:
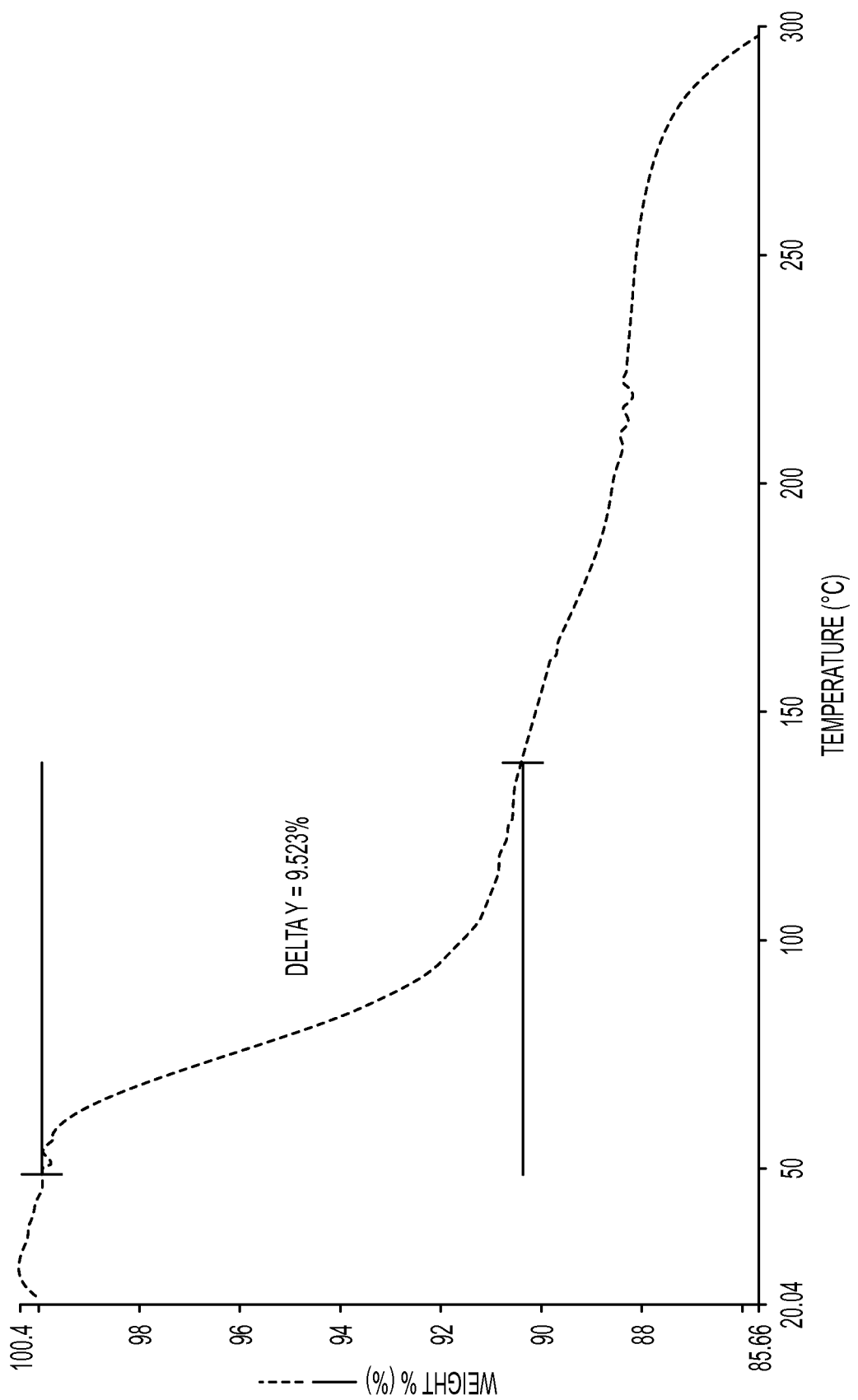
FIG. 17 depicts a TGA trace of crystalline genistein potassium salt dihydrate.

As shown in FIG. 17, TGA indicates that the potassium salt is hydrated and water loss commences at ca. 75° C., suitable for further development. The weight loss is consistent with 2 moles of water to 1 mole of potassium.

2.6 DSC of Crystalline Genistein Potassium Salt Dihydrate

Figure 18:
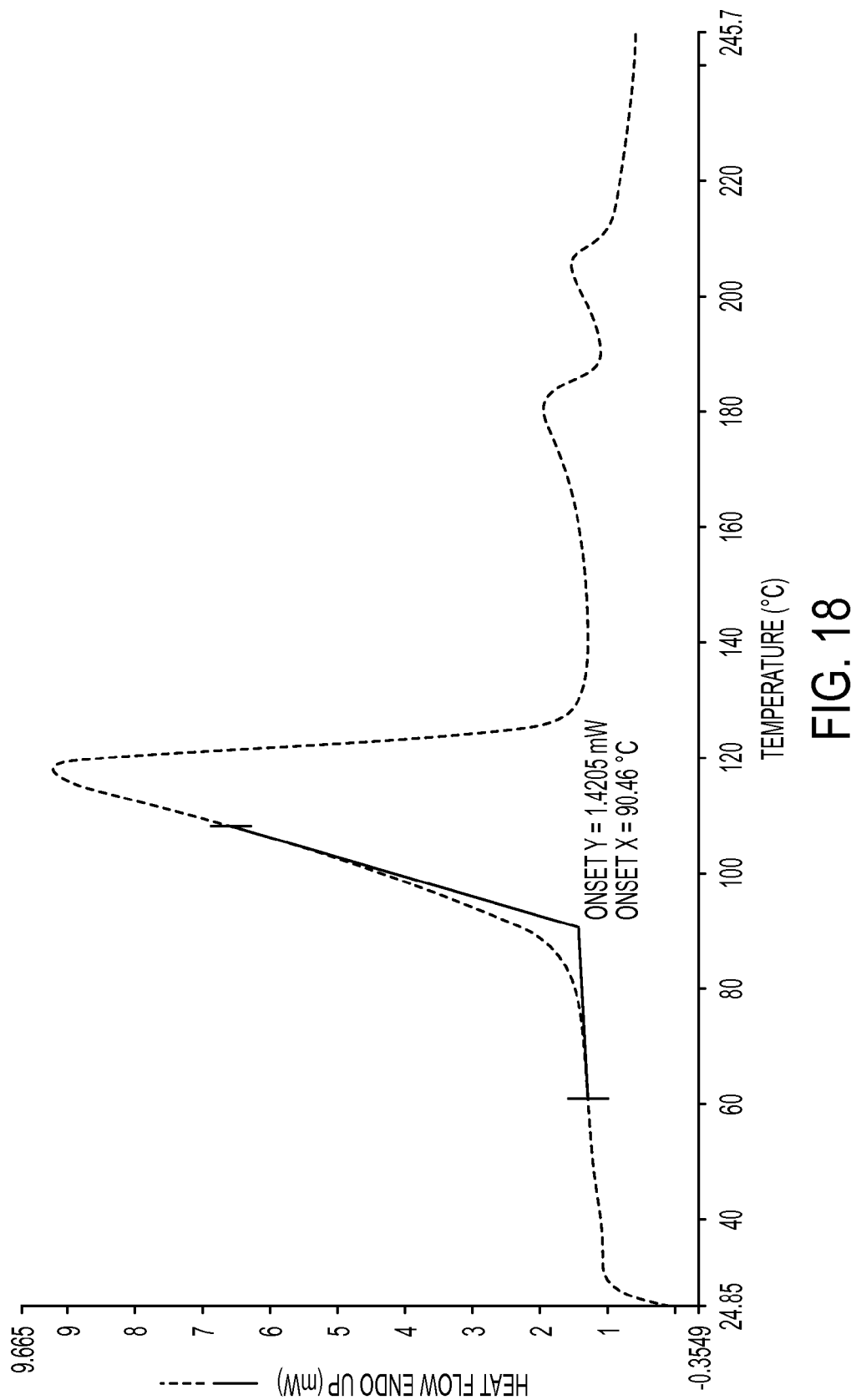
FIG. 18 depicts a DSC trace of crystalline genistein potassium salt dihydrate.

As shown in FIG. 18, DSC indicates dehydration $^c$a. 91° C. with no melting. The other peaks are probably associated with degradation (as also indicated by the TGA, FIG. 16).

2.7 GVS of Crystalline Genistein Potassium Salt Dihydrate

Figure 19:
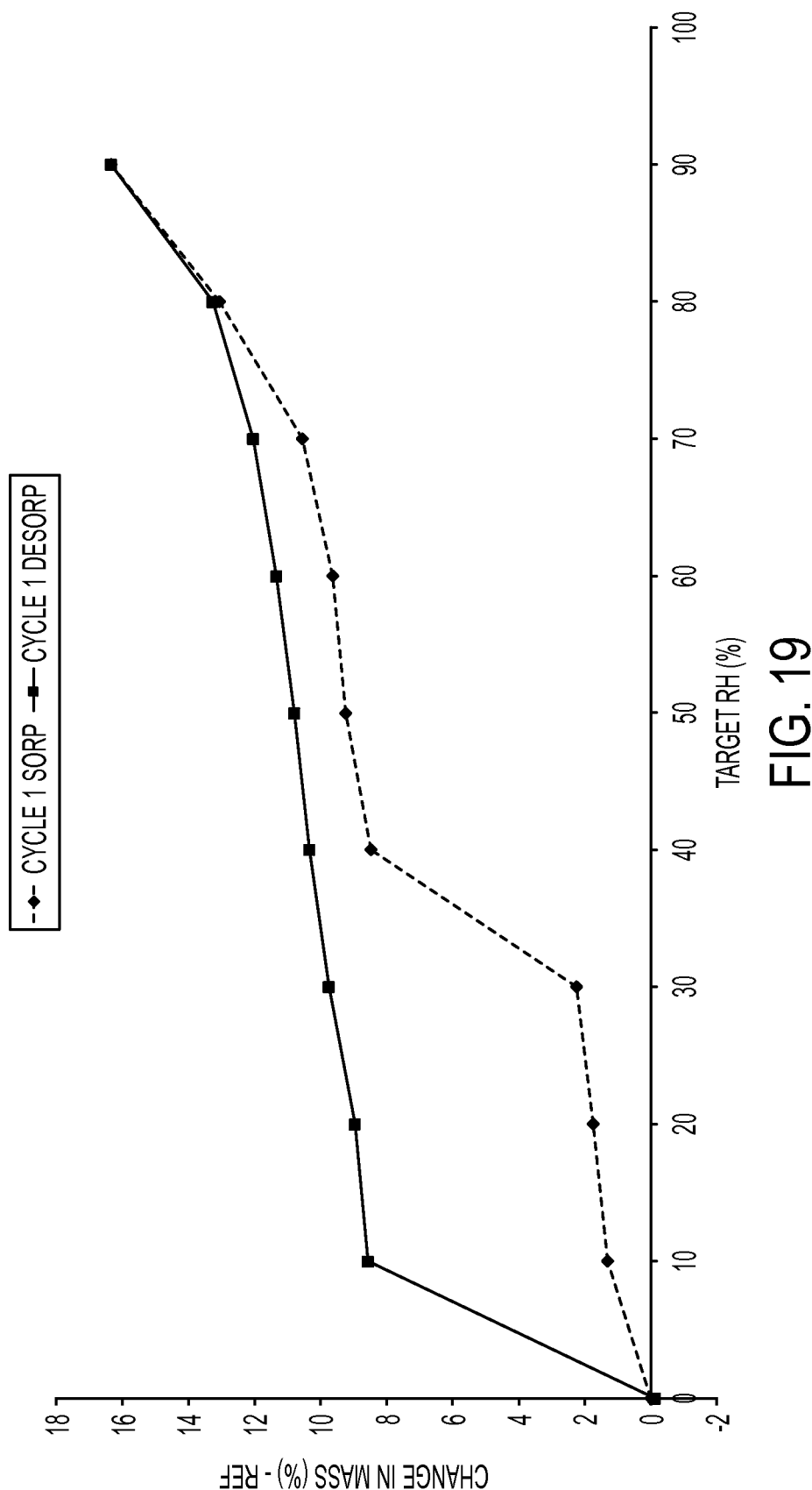
FIG. 19 depicts a GVS trace of crystalline genistein potassium salt dihydrate.

As shown in FIG. 19, GVS studies indicate hydrate formation (GVS cycle dehydrates material prior to analysis and a maximum of 16 wt % of water adsorbed. However, between 20 and 70 RH % (typical working range of material) only ca. 3% moisture change is observed. This is a valuable property for pharmaceutical development.

2.8 Solubility Study of Crystalline Genistein Potassium Salt Dihydrate

The aqueous solubility of crystalline genistein potassium salt dihydrate was measured using the protocol described in Example 1.7. Table 16 compares the aqueous solubilities of crystalline genistein potassium salt dihydrate with that of genistein.

TABLE 16

| Solvent | Genistein, mg/ml | Crystalline Genistein Potassium Salt Dihydrate, mg/ml |
|---|---|---|
| Water/slurry pH 4.5 | BDL | 0.04 |
| Water/slurry pH 6.7 | BDL | 0.057 |
| Water/slurry pH 7.5 | BDL | 0.069 |

2.9 $^1$H NMR of Crystalline Genistein Potassium Salt Dihydrate

Figure 20:
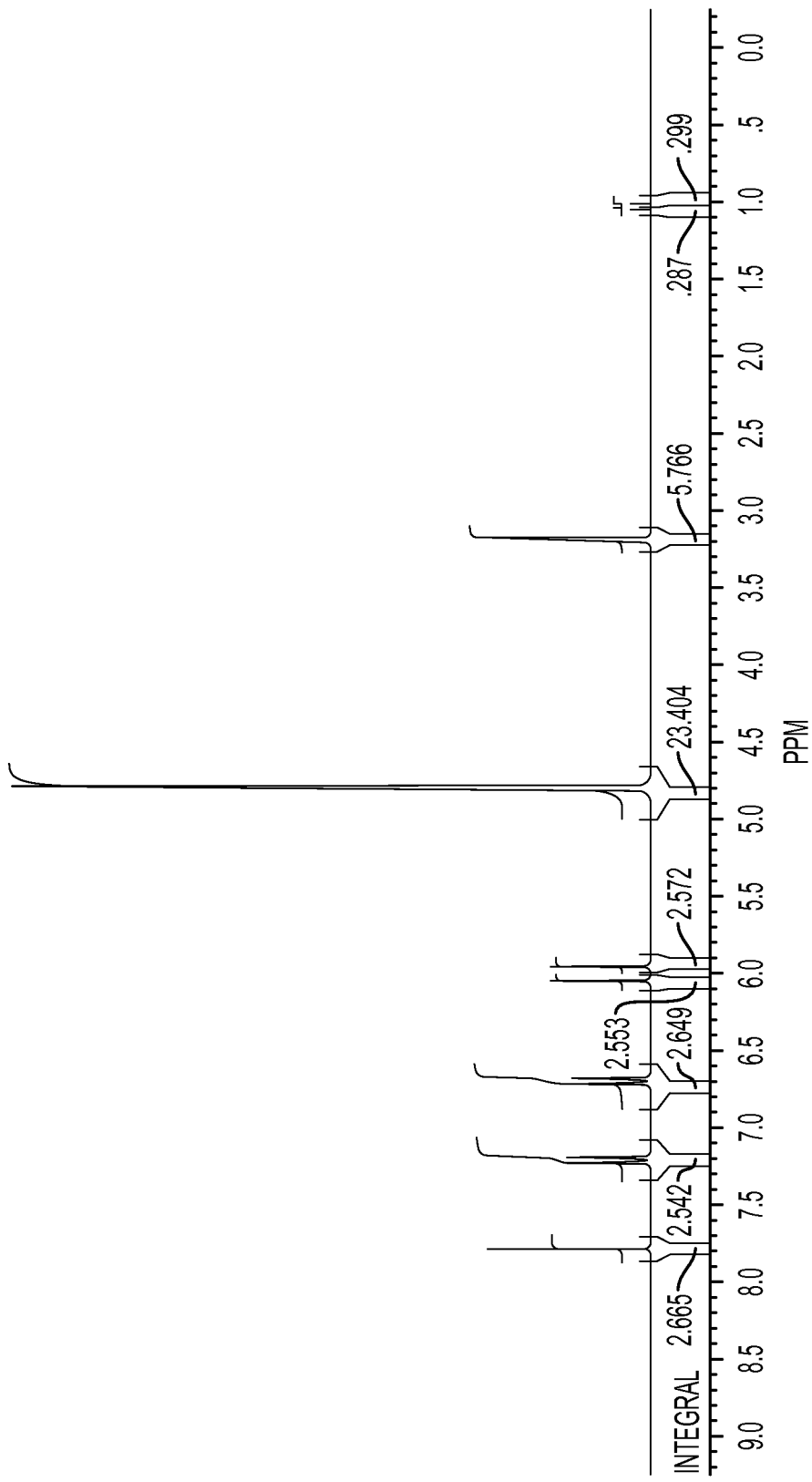
FIG. 20 depicts the $^1$H NMR of crystalline genistein potassium salt dihydrate.

FIG. 20 illustrates the $^1$H NMR spectrum of the crystalline genistein potassium salt dihydrate. Table 17 lists the peaks in the $^1$H NMR spectrum. Displacement of the chemical shifts for the aromatic protons at ca. 5.9 in genistein to 6.1 ppm in the $^1$H NMR of FIG. 20 confirms salt formation.

TABLE 17

| Chemical Shift | Mulitlpicity | Range |
| --- | --- | --- |
| 7.959 | S | 8.009-7.941 |
| 7.375 | m | 7.437-7.322 |
| 6.861 | m | 6.932-6.800 |
| 6.154 | dd | 6.246-6.068 |
| 4.949 | s | 5.148-4.714 |
| 3.34 | q | 3.444-3.137 |
| 1.182 | d | 1.228-1.149 |

Figure 21:
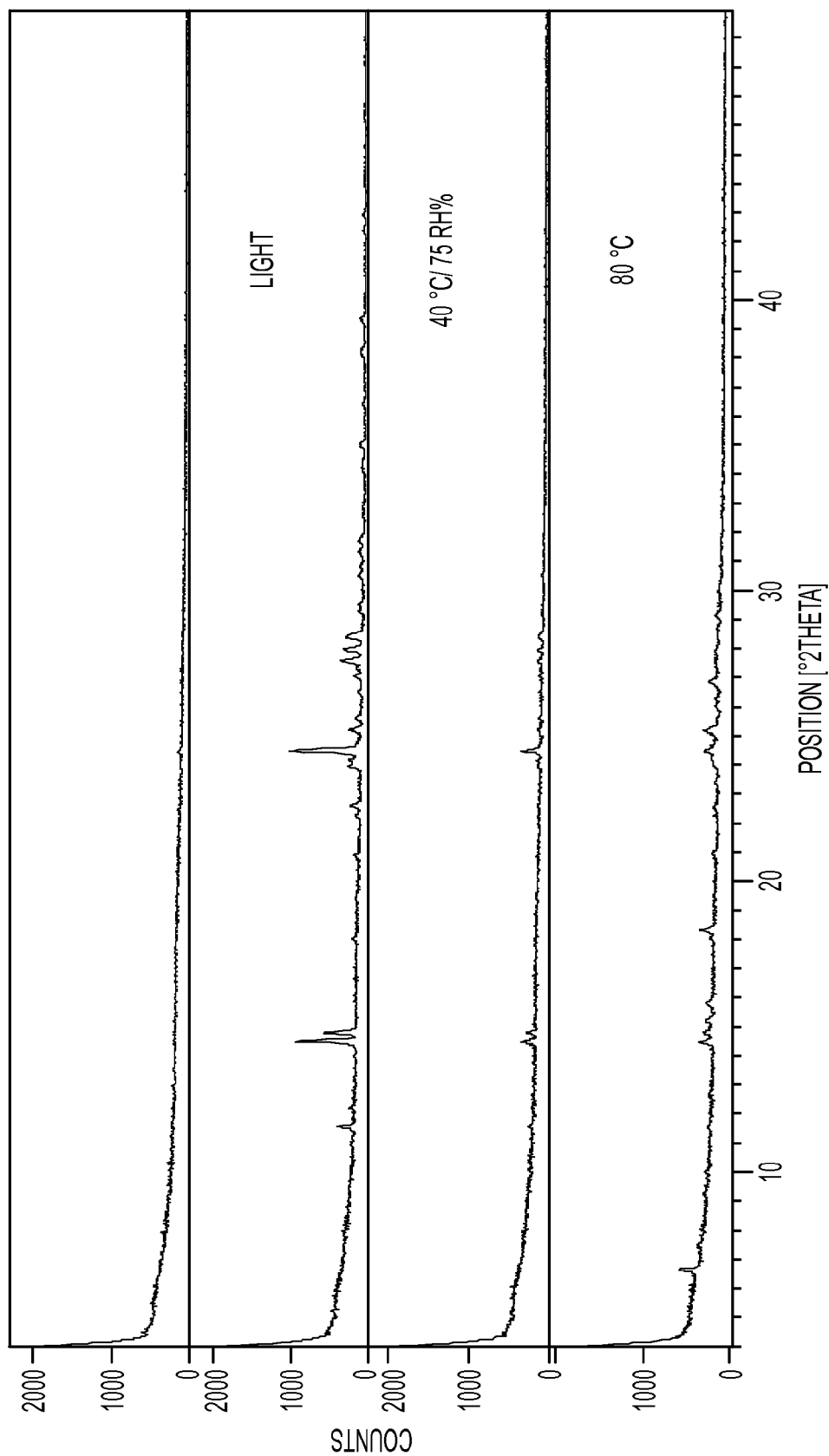
FIG. 21 depicts XRPD patterns from the stability study of crystalline genistein potassium salt dihydrate.

S = singlet, m = multiplet, d = doublet, dd = double doublet, q = quadruplet 2.10 Stability Study of Crystalline Genistein Potassium Salt Dihydrate Sample stability was tested at 80° C. for 7 days and at 40° C./75 RH % for 7 days. Observations such as color change were noted after 7 days and XRPD of samples were taken after 7 days to investigate any solid form change. FIG. 21 shows the XRPD patterns of samples of crystalline genistein potassium salt dihydrate at 80° C. for 7 days and at 40° C./75 RH % for 7 days. The 40° C./75 RH % study indicates that genistein potassium salt crystallizes to form genistein potassium salt dihydrate, Storing crystalline genistein potassium salt dihydrate at 80° C. over a 7 day period has indicated crystallization to genistein potassium salt dihydrate.

2.11 Hydration Study of Crystalline Genistein Potassium Salt Dihydrate

Figure 22:
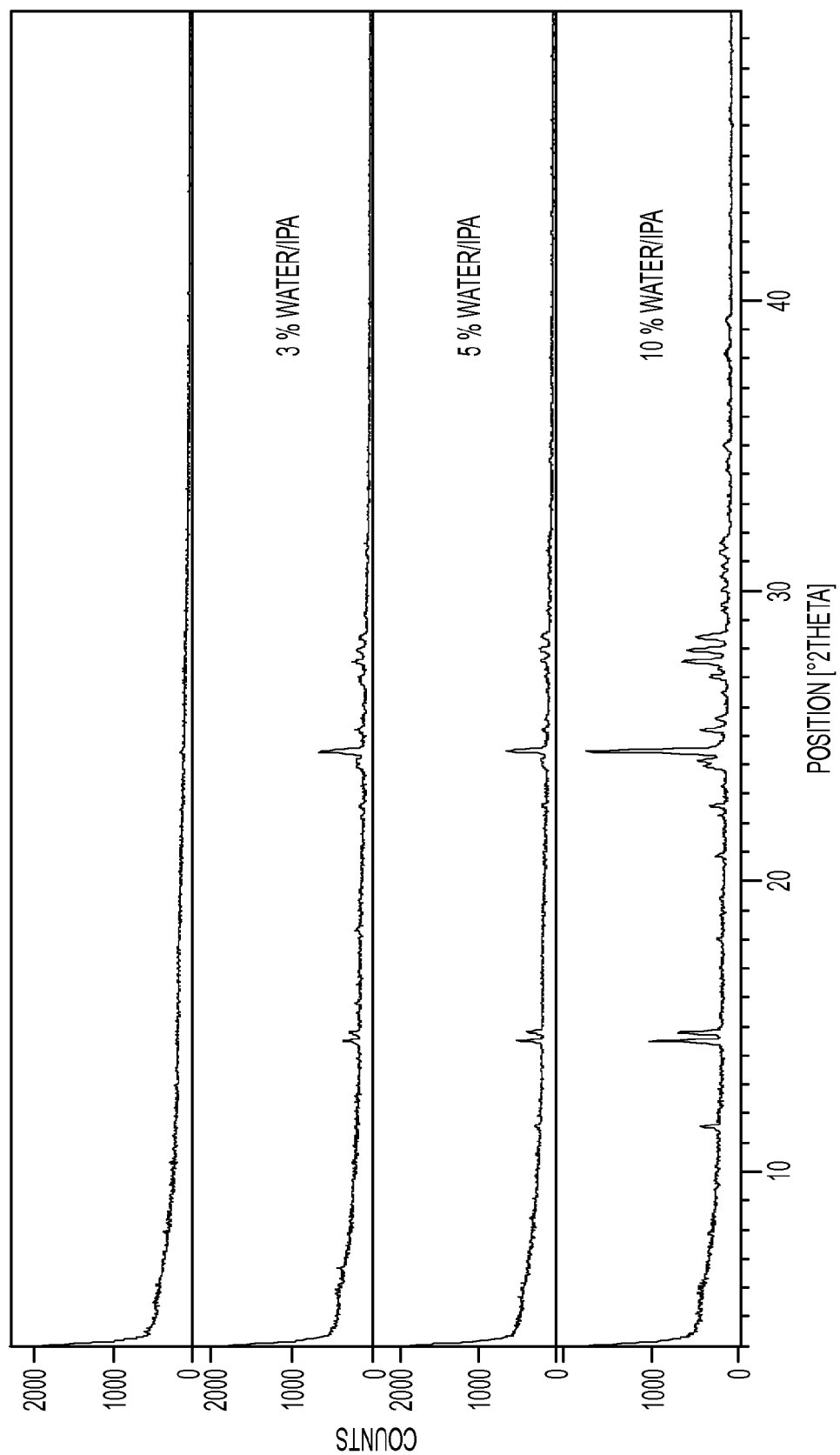
FIG. 22 depicts XRPD patterns for a hydration study of crystalline genistein potassium dihydrate.

Approximately 100 mg of crystalline genistein sodium salt dihydrate was placed in ca. 500 µL IPA/water mixtures (3%, 5% and 10%) at the water level. Each mixture was agitated for ca. 48 hours at ambient temperature and then filtered to recover the solid for XRPD and TGA studies. As shown in FIG. 22, the hydration study revealed a hydrate consistent with crystalline genistein potassium salt dihydrate.

2.12 Disproportionation Study of Crystalline Genistein Potassium Salt Dihydrate

A sample of crystalline genistein potassium salt dihydrate was slurried in distilled water for ca. 48 hours and then checked by XRPD for disproportionation. The pH of the supernatant was also measured using a Corning 240 pH meter. No signs of disproportionation were observed. The pH of the supernatant liquid was 7.3 indicating no disproportionation.

Example 3

Crystalline Genistein Calcium Salt 3.1 Preparation of Crystalline Genistein Calcium Salt Approximately 25 mg of genistein was placed in the same vessel as ca. 7 mg of solid calcium hydroxide, To the solid mixture, 500 µL of IPA/Water (50:50) was added and the mixture shaken at ambient temperature for ca. 24 hours. Subsequent to stirring, the slurry was then temperature cycled (40° C. to ambient temperature, in 4 hour periods) with shaking for ca. 72 hours. The solid was then isolated by filtration and allowed to dry at ambient temperature for ca. 24 hours.

3.2 Characterization of Crystalline Genistein Calcium Salt

Figure 23:
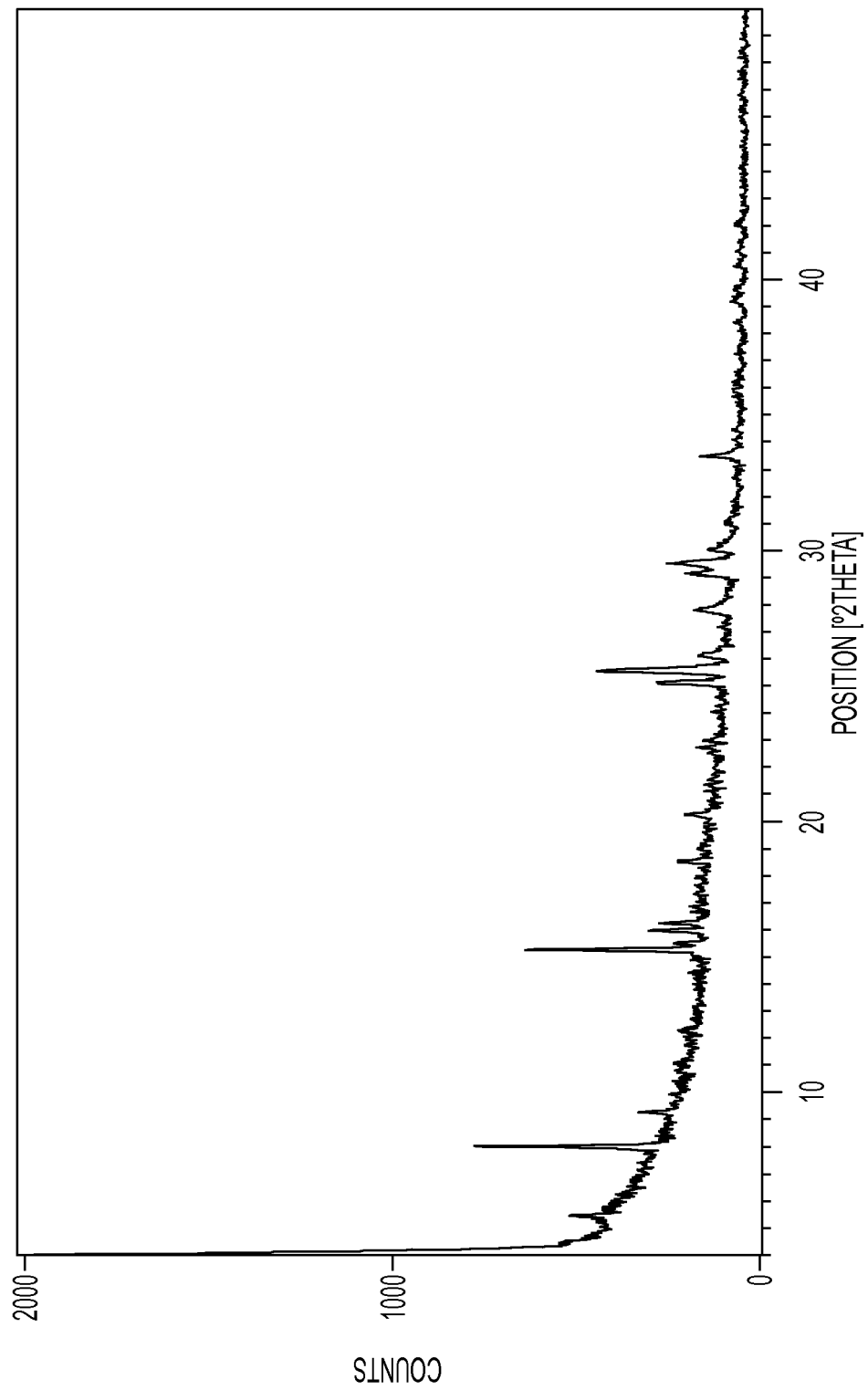
FIG. 23 depicts an XRPD pattern for crystalline genistein calcium salt.
Figure 24:
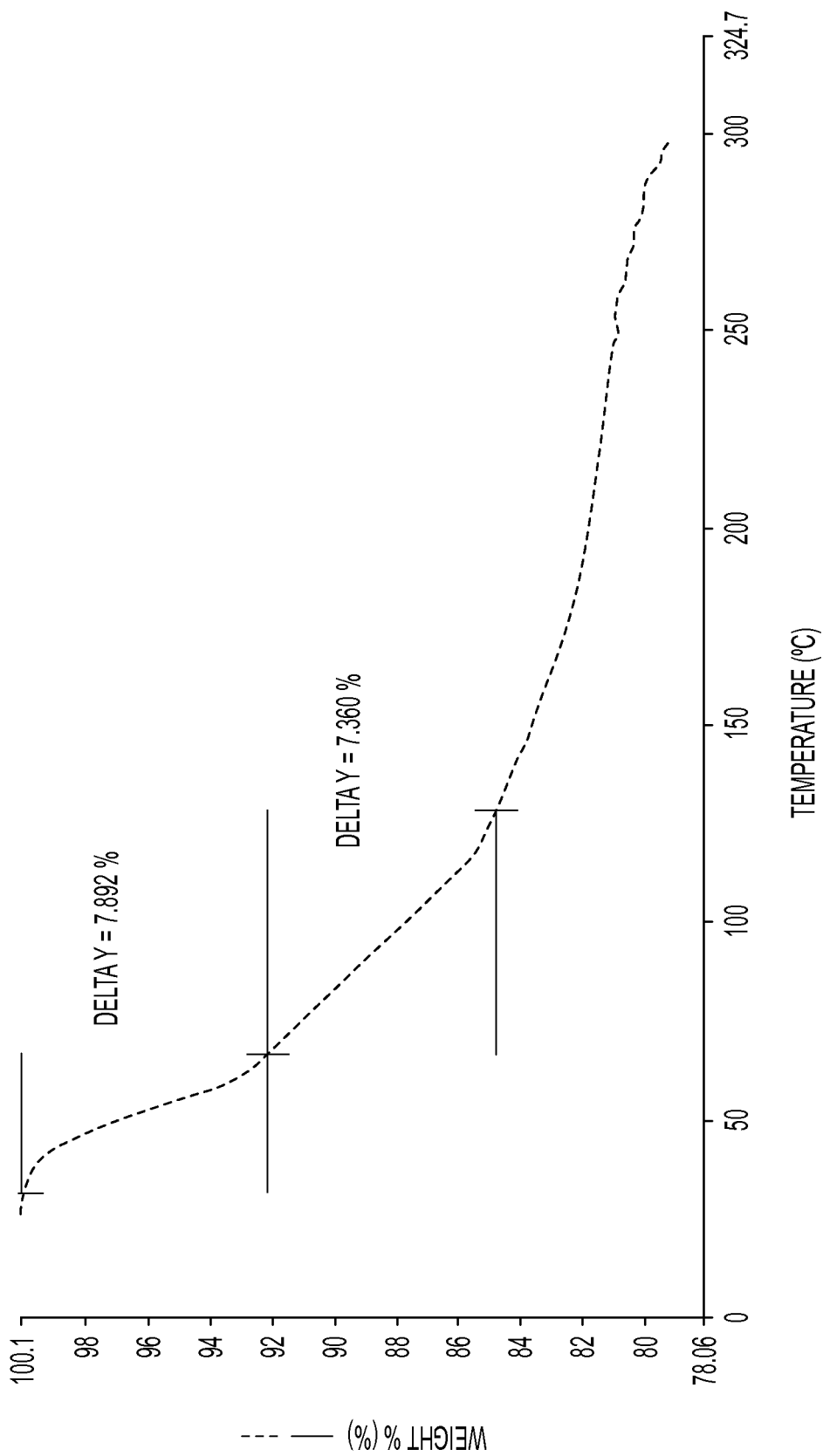
FIG. 24 depicts the TGA trace for crystalline genistein calcium salt.

FIG. 23 shows the XRPD pattern of the crystalline genistein calcium salt. The peaks in the XRPD pattern at an experimental °2θ±0.2°2θ are listed in Table 18. The entire list of peaks, or a subset thereof, may be sufficient to characterize crystalline genistein calcium salt. One subset of peaks that, individually or in combination, may be used to characterize crystalline genistein calcium salt from FIG. 23 includes 8.0, 15.3, 25.1, and 25.6°2θ±0.2°2θ. The TGA of crystalline genistein calcium salt is shown in FIG. 24. The PIM image of the crystalline genistein calcium salt showed needle-shaped crystals.

TABLE 18

| Pos. [°2θ ± 0.2 °2θ] | d-spacing [Å] | Rel. Int. [%] |
| --- | --- | --- |
| 5.4 | 16.2 | 21.82 |
| 8.0 | 11.0 | 98.01 |
| 9.3 | 9.5 | 17.32 |
| 15.3 | 5.8 | 100.00 |
| 15.5 | 5.7 | 17.27 |
| 16.0 | 5.6 | 31.04 |
| 16.3 | 5.5 | 24.40 |
| 16.8 | 5.3 | 6.33 |
| 18.5 | 4.8 | 17.43 |
| 19.0 | 4.7 | 6.23 |
| 20.3 | 4.4 | 16.69 |
| 21.5 | 4.1 | 5.44 |
| 22.5 | 3.9 | 7.30 |
| 22.7 | 3.9 | 14.06 |
| 23.0 | 3.9 | 7.86 |
| 24.1 | 3.7 | 6.61 |
| 25.1 | 3.5 | 37.75 |
| 25.6 | 3.5 | 72.44 |
| 26.1 | 3.4 | 15.90 |
| 27.8 | 3.2 | 20.14 |
| 29.2 | 3.1 | 23.14 |
| 29.5 | 3.0 | 34.31 |
| 30.0 | 3.0 | 15.01 |
| 33.5 | 2.7 | 19.69 |

Example 4

Crystalline Genistein Magnesium Salt, 1 Equivalent Preparation 4.1 Preparation of Crystalline Genistein Magnesium Salt, 1 Equivalent Approximately 25 mg of genistein was placed in the same vessel as ca. 5.5 mg of solid magnesium hydroxide. To the solid mixture, 500 µL of IPA/Water (50:50) was added and the mixture shaken at ambient temperature for ca. 24 hours. Subsequent to stirring, the slurry was then temperature cycled (40° C. to ambient temperature, in 4 hour periods) with shaking for ca. 72 hours. The solid was then isolated by filtration and allowed to dry at ambient temperature for ca. 24 hours.

4.2 Characterization of Crystalline Genistein Magnesium Salt, 1 Equivalent

Figure 25:
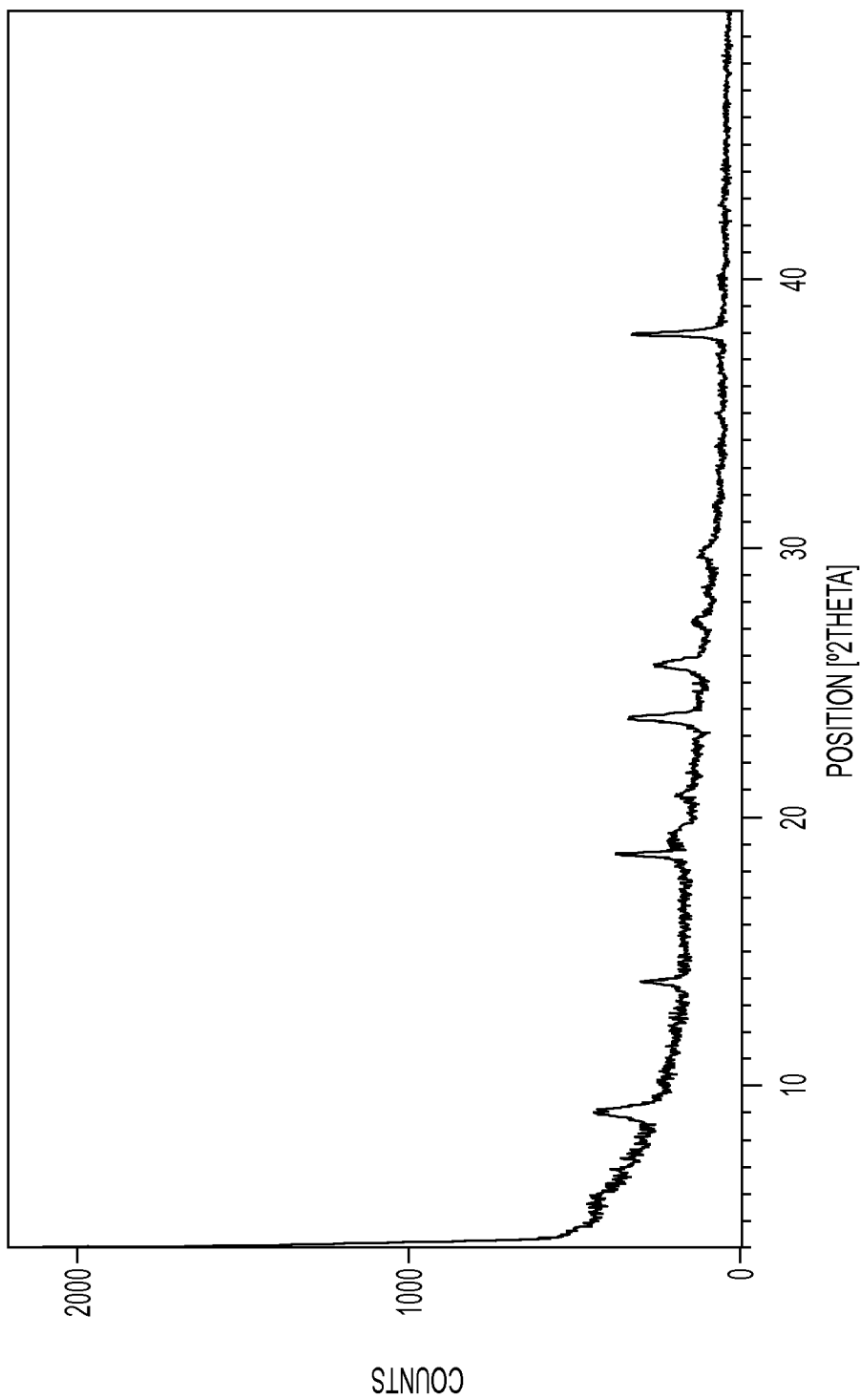
FIG. 25 depicts an XRPD pattern for crystalline genistein magnesium salt, 1 equivalent.
Figure 26:
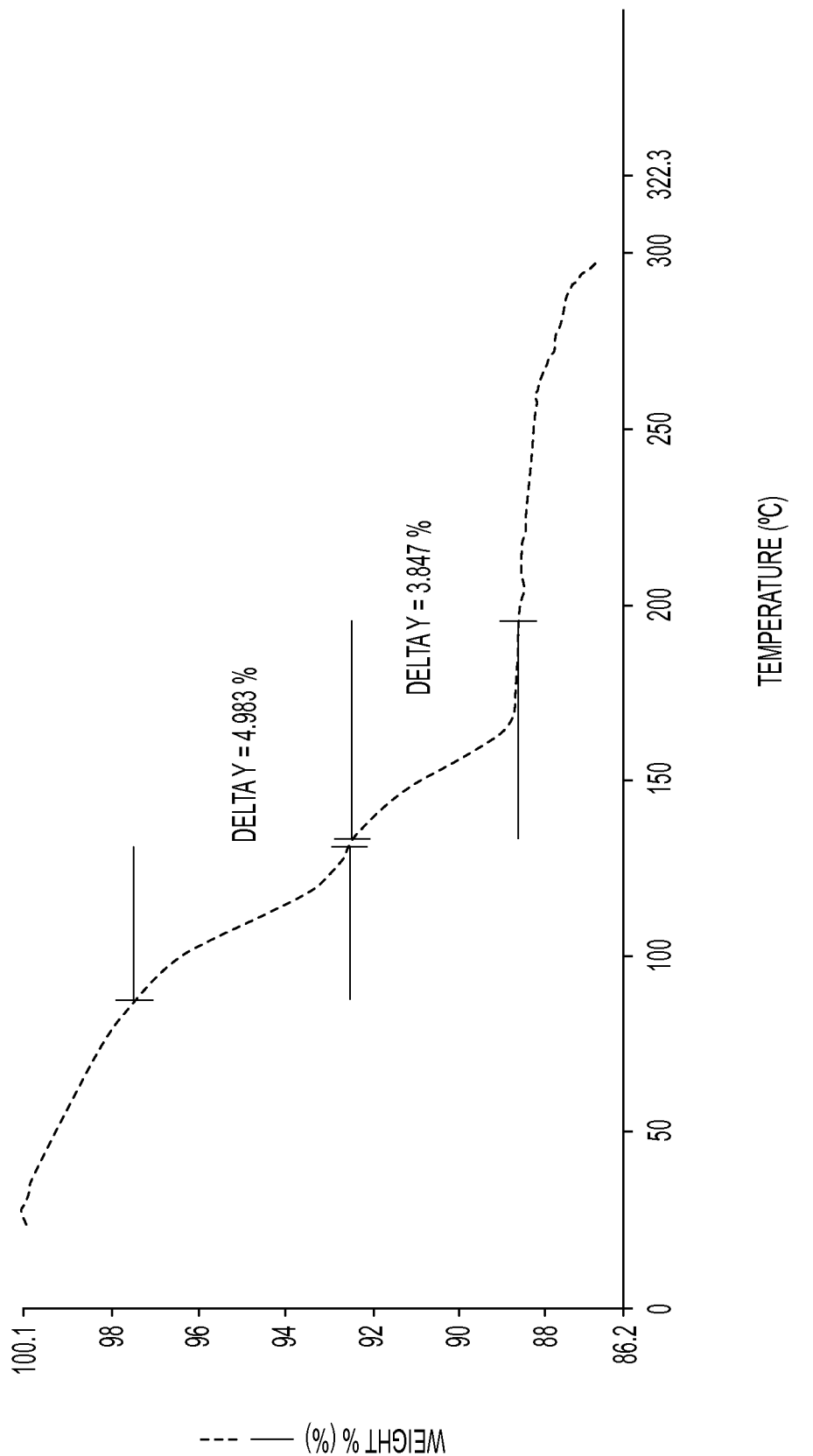
FIG. 26 depicts the TGA trace for crystalline genistein magnesium salt, 1 equivalent.

FIG. 25 shows the XRPD pattern of the crystalline genistein magnesium salt from the 1 equivalent preparation. The peaks in the XRPD pattern at an experimental °2θ±0.2°2θ are listed in Table 19. The entire list of peaks, or a subset thereof, may be sufficient to characterize crystalline genistein magnesium salt. One subset of peaks that, individually or in combination, may be used to characterize crystalline genistein magnesium salt from FIG. 25 includes 9.0, 18.6, 23.7, 25.7, and 38.0°2θ±0.2°2θ. The TGA of crystalline genistein magnesium salt, 1 equivalent preparation, is shown in FIG. 26. The PLM image of crystalline genistein magnesium salt, 1 equivalent preparation, showed the genistein magnesium salt to be crystalline.

TABLE 19

| Pos. [°2θ ± 0.2 °2θ] | d-spacing [Å] | Rel. Int. [%] |
| --- | --- | --- |
| 5.8 | 15.2 | 10.51 |
| 9.0 | 9.8 | 65.09 |
| 13.9 | 6.4 | 49.78 |
| 18.6 | 4.8 | 84.23 |
| 20.8 | 4.3 | 17.43 |
| 23.7 | 3.8 | 81.78 |
| 25.7 | 3.5 | 57.42 |
| 27.3 | 3.3 | 15.2 |
| 29.8 | 3.0 | 15.46 |
| 34.9 | 2.6 | 4.44 |
| 38.0 | 2.4 | 100 |

Example 5

Crystalline Genistein Magnesium Salt, 2 Equivalent Preparation 5.1 Preparation of Crystalline Genistein Magnesium Salt, 2 Equivalents Approximately 25 mg of genistein was placed in the same vessel as ca. 11 mg of solid magnesium hydroxide. To the solid mixture, 500 μL of IPA/Water (50:50) was added and the mixture shaken at ambient temperature for ca. 24 hours, Subsequent to stirring, the slurry was then temperature cycled (40° C. to ambient temperature, in 4 hour periods) with shaking for ca. 72 hours. The solid was then isolated by filtration and allowed to dry at ambient temperature for ca. 24 hours.

Figure 27:
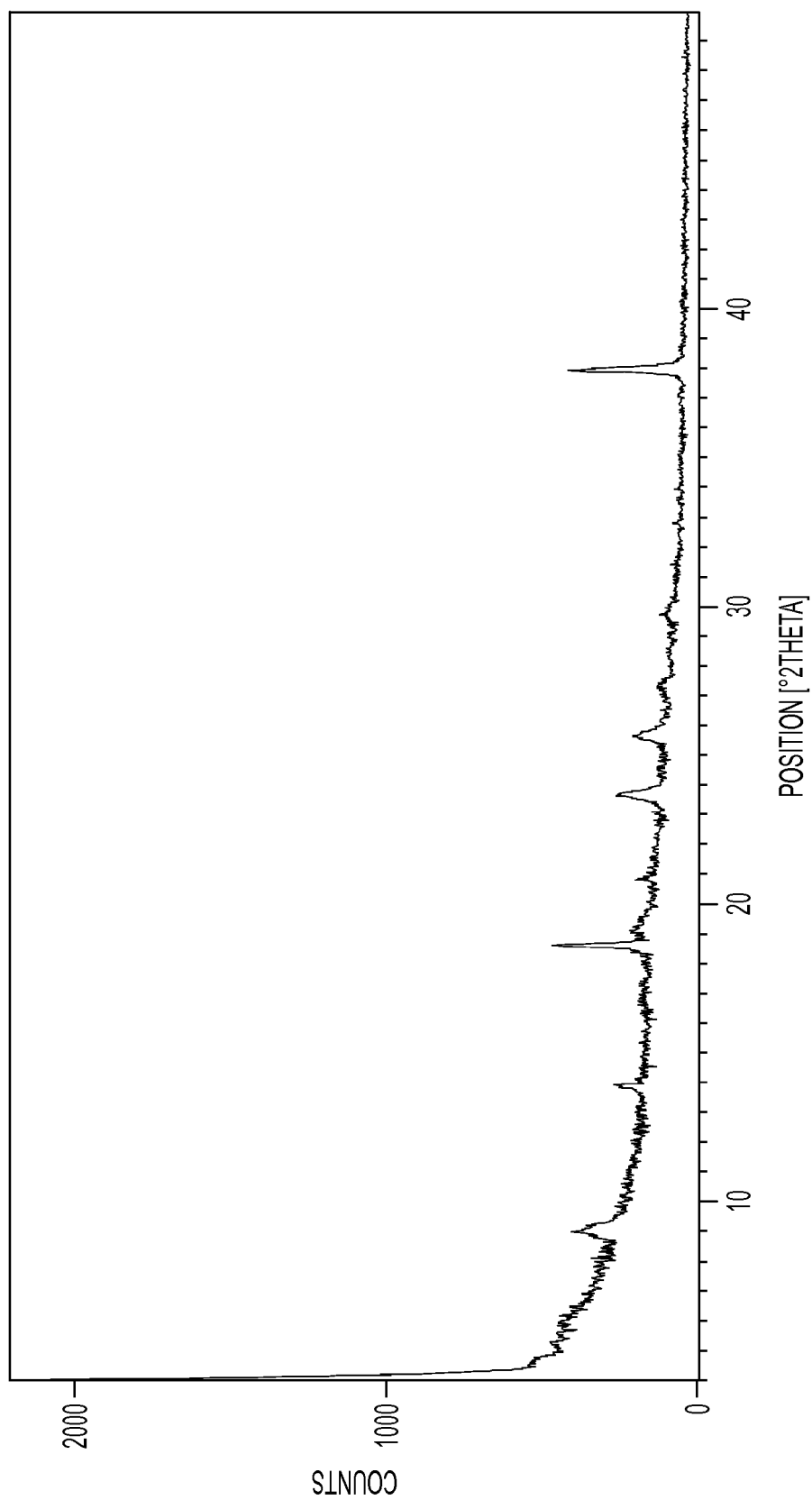
FIG. 27 depicts an XRPD pattern for crystalline genistein magnesium salt, 2 equivalents.
Figure 28:
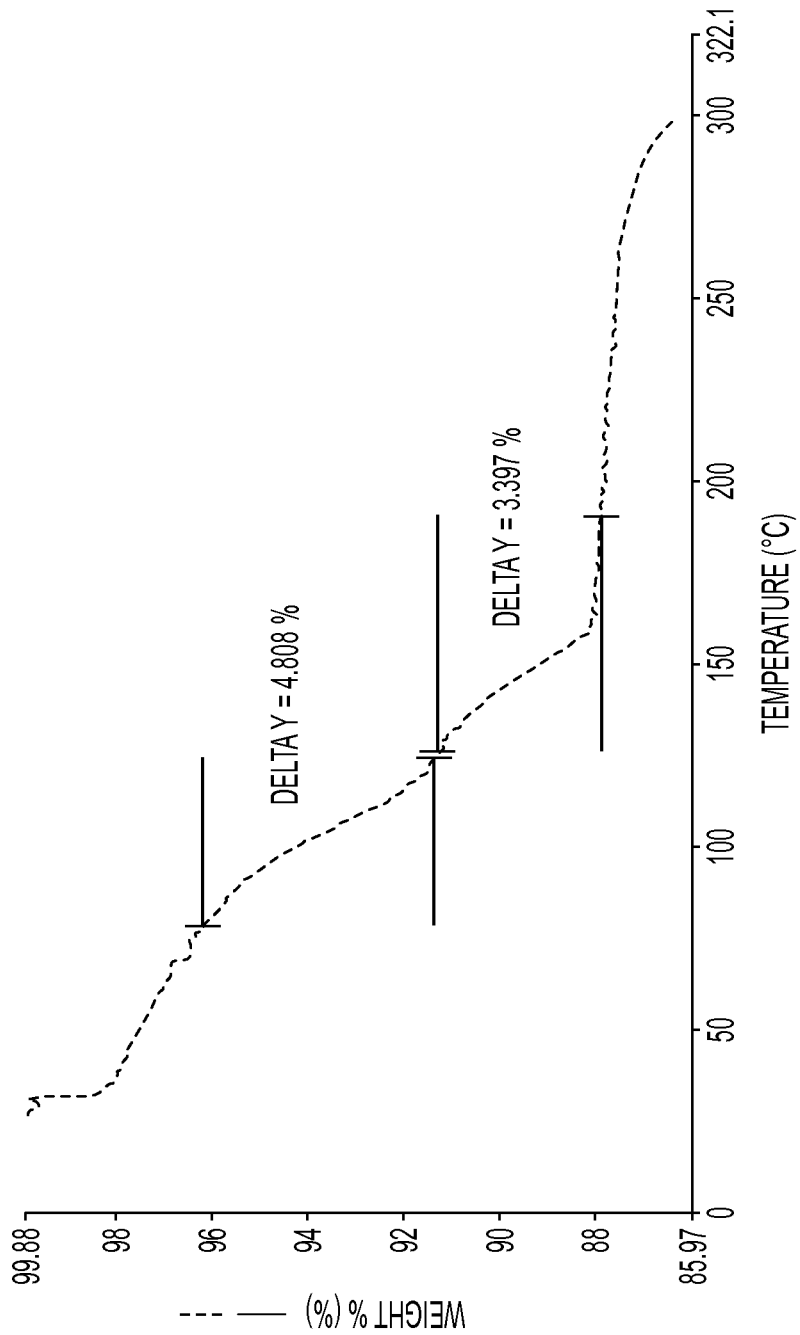
FIG. 28 depicts the TGA trace for crystalline genistein magnesium salt, 2 equivalents.

5.2 Characterization of Crystalline Genistein Magnesium Salt, 2 Equivalent Preparation FIG. 27 shows the XRPD pattern of the crystalline genistein magnesium salt, 2 equivalent preparation. The peaks in the XRPD pattern at an experimental °2θ±0.2°2θ are listed in Table 20. The entire list of peaks, or a subset thereof, may be sufficient to characterize crystalline genistein magnesium salt. The TGA trace of crystalline genistein magnesium salt, 2 equivalents, is shown in FIG. 28.

TABLE 20

| Pos. [°2θ ± 0.2 °2θ] | d-spacing [Å] | Rel. Int. [%] |
| --- | --- | --- |
| 9.0 | 9.8 | 30.28 |
| 13.9 | 6.4 | 20.73 |
| 18.6 | 4.8 | 81.86 |
| 20.8 | 4.3 | 12.63 |
| 23.7 | 3.8 | 38.11 |
| 25.7 | 3.5 | 28.52 |
| 27.3 | 3.3 | 8.99 |
| 29.7 | 3.0 | 9.05 |
| 38.0 | 2.4 | 100 |

The similar XRPD patterns and TGA traces for the crystalline genistein magnesium salt from both the 1 equivalent preparation and the 2 equivalent preparation suggests that the same crystalline genistein magnesium salt is obtained from both preparations. One subset of XRPD peaks that, individually or in combination, may be used to characterize crystalline genistein magnesium salt includes 9.0, 18.6, 23.7, 25.7, and 38.0°2θ±0.2°2 θ.

Example 6

Crystalline Genistein L-Lysine Salt 6.1 Preparation of Crystalline Genistein L-Lysine Salt Approximately 25 mg of genistein was placed in the same vessel as cu. 15 mg of solid L-lysine monohydrate, To the solid mixture, 500 μL of either IPA or of toluene was added and the mixture shaken at ambient temperature for ca. 24 hours. Subsequent to stirring, the slurry was then temperature cycled (40° C. to ambient temperature, in 4 hour periods) with shaking for ca. 72 hours. The solid was then isolated by filtration and allowed to dry at ambient temperature for ca. 24 hours.

6.2 Characterization of Crystalline Genistein L-Lysine Salt/Genistein Mixtures

Figure 29:
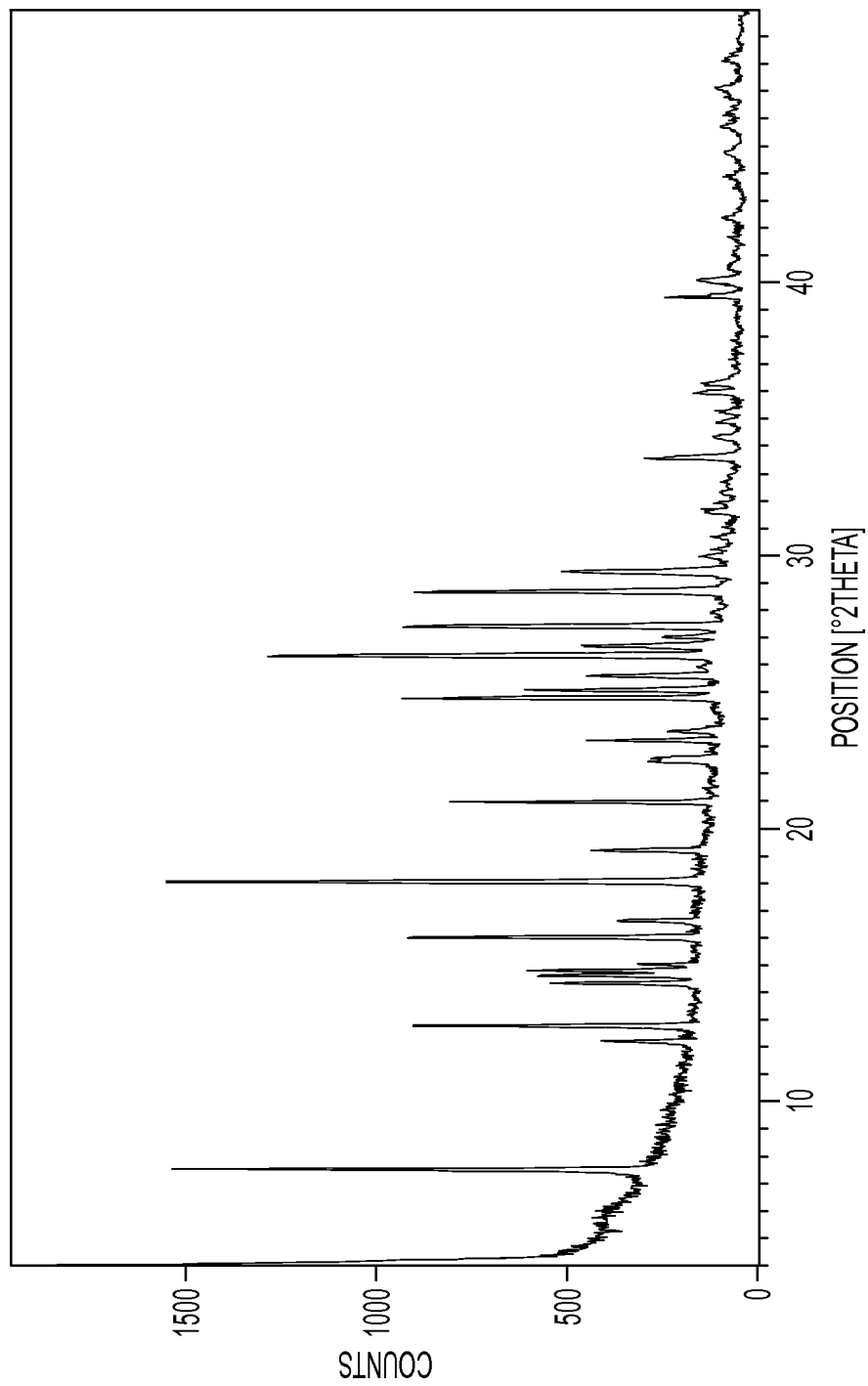
FIG. 29 depicts an XRPD pattern for crystalline genistein.
Figure 30:
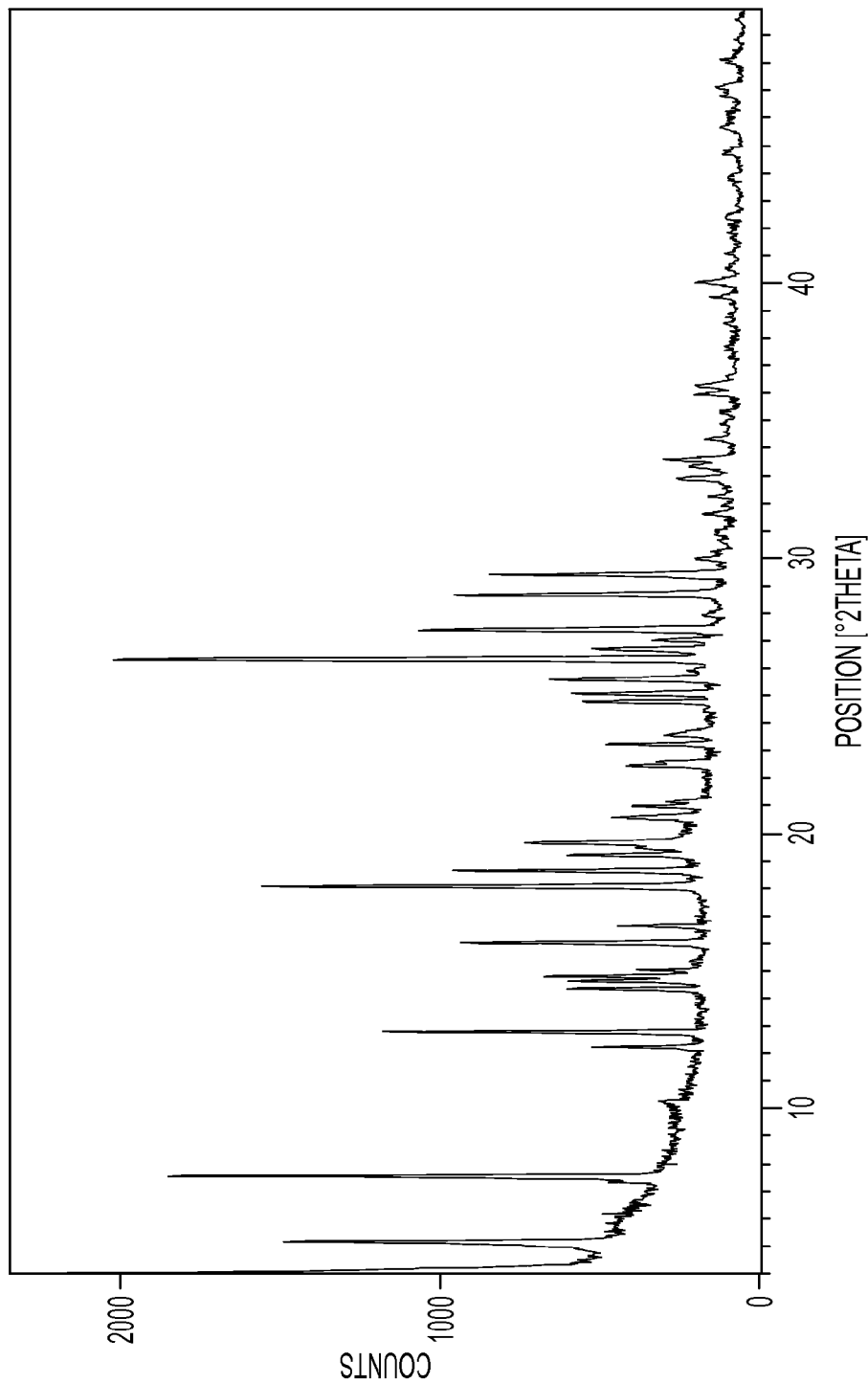
FIG. 30 depicts an XRPD pattern for crystalline genistein L-Lysine salt from toluene.
Figure 31:
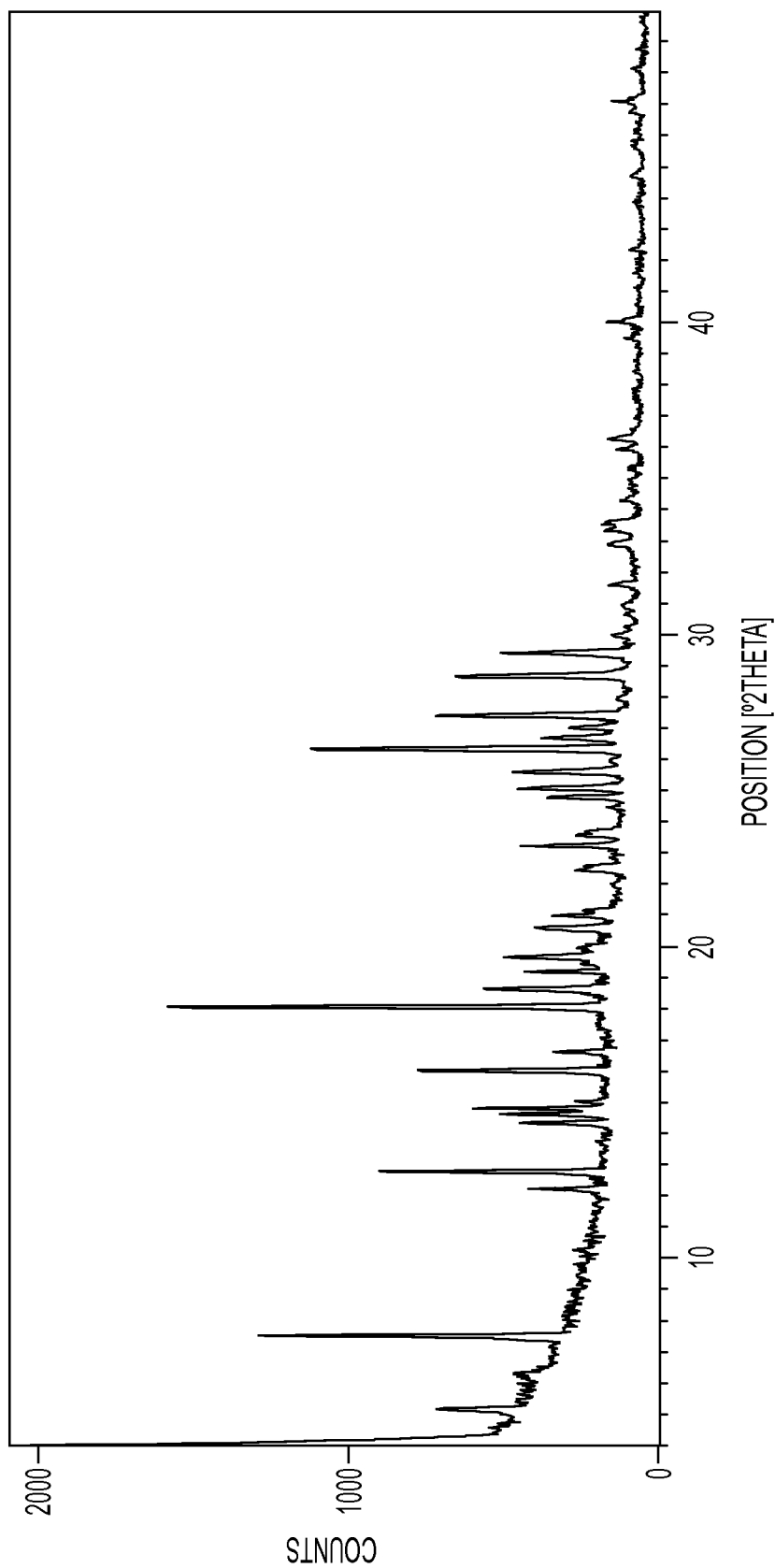
FIG. 31 depicts an XRPD pattern for crystalline genistein L-Lysine salt from isopropanol.

Samples of crystalline genistein L-lysine salt from toluene and IPA were analyzed by XRPD and the XRPD patterns shown in FIGS. 30 and 31 were generated. The XRPD pattern for crystalline genistein is also shown below. As indicated by the XRPD, both methods produced mixtures of genistein and genistein L-lysine salt. FIG. 29 shows the XRPD pattern of the crystalline genistein. The peaks in the XRPD pattern of FIG. 29 at an experimental °2θ±0.2°2θ are listed in Table 21.

TABLE 21

| Pos. [°2θ ± 0.2 °2θ] | d-spacing [Å] | Rel. Int. [%] |
| --- | --- | --- |
| 7.5 | 11.7 | 81.81 |
| 12.2 | 7.3 | 15.94 |
| 12.8 | 6.9 | 52.19 |
| 14.3 | 6.2 | 27.23 |
| 14.6 | 6.1 | 28.38 |
| 14.8 | 6.0 | 30.72 |
| 15.0 | 5.9 | 11.15 |
| 16.0 | 5.5 | 52.69 |
| 16.6 | 5.3 | 15.61 |
| 18.1 | 4.9 | 100 |
| 19.2 | 4.6 | 21.11 |
| 21.0 | 4.2 | 47.41 |
| 22.4 | 4.0 | 12.28 |
| 22.6 | 3.9 | 10.2 |
| 23.2 | 3.8 | 23.76 |
| 23.6 | 3.8 | 9.17 |
| 24.8 | 3.6 | 51.75 |
| 25.1 | 3.6 | 33.66 |
| 25.6 | 3.5 | 24.89 |
| 26.3 | 3.4 | 81.12 |
| 26.7 | 3.3 | 23.35 |
| 27.0 | 3.3 | 10.41 |
| 27.4 | 3.3 | 56.24 |
| 28.7 | 3.1 | 56.15 |
| 29.4 | 3.0 | 30.44 |
| 33.6 | 2.7 | 14.28 |
| 35.9 | 2.5 | 7.63 |
| 39.5 | 2.3 | 13.43 |
| 40.1 | 2.3 | 7.68 |

6.3 Characterization of Crystalline Genistein L-Lysine Salt from Toluene

FIG. 30 shows the XRPD pattern of the crystalline genistein L-lysine salt from toluene. The peaks in the XRPD pattern at an experimental °2θ±0.2°2θ are listed in Table 22.

TABLE 22

| Pos. [°2θ ± 0.2 °2θ] | d-spacing [Å] | Rel. Int. [%] |
| --- | --- | --- |
| 5.2 | 17.1 | 73.48 |
| 7.5 | 11.7 | 94.46 |

TABLE 22-continued

| Pos. [°2θ ± 0.2 °2θ] | d-spacing [Å] | Rel. Int. [%] |
|---|---|---|
| 10.2 | 8.7 | 12.47 |
| 12.2 | 7.2 | 23.99 |
| 12.8 | 6.9 | 57.82 |
| 14.3 | 6.2 | 28.25 |
| 14.6 | 6.1 | 27.59 |
| 14.8 | 6.0 | 32.21 |
| 15.0 | 5.9 | 17.49 |
| 16.0 | 5.5 | 45.2 |
| 16.6 | 5.3 | 19.53 |
| 18.1 | 4.9 | 77.67 |
| 18.6 | 4.8 | 46.56 |
| 19.2 | 4.6 | 28.29 |
| 19.7 | 4.5 | 34.98 |
| 20.6 | 4.3 | 20.97 |
| 21.0 | 4.2 | 17.82 |
| 21.2 | 4.2 | 11.09 |
| 22.4 | 4.0 | 17.25 |
| 22.6 | 3.9 | 12.61 |
| 23.2 | 3.8 | 21.8 |
| 23.6 | 3.8 | 12.36 |
| 24.8 | 3.6 | 25.82 |
| 25.1 | 3.6 | 27.26 |
| 25.6 | 3.5 | 30.47 |
| 26.3 | 3.4 | 100 |
| 26.7 | 3.3 | 23.56 |
| 27.0 | 3.3 | 14.34 |
| 27.4 | 3.3 | 50.01 |
| 27.9 | 3.2 | 6.19 |
| 28.7 | 3.1 | 46.23 |
| 29.4 | 3.0 | 40.47 |
| 32.9 | 2.7 | 9.67 |
| 33.6 | 2.7 | 12.33 |
| 36.0 | 2.5 | 7.24 |
| 36.3 | 2.5 | 7.15 |
| 39.5 | 2.3 | 5.12 |
| 40.0 | 2.3 | 6.87 |

6.4 Characterization of Crystalline Genistein L-Lysine Salt from IPA

Figure 32:
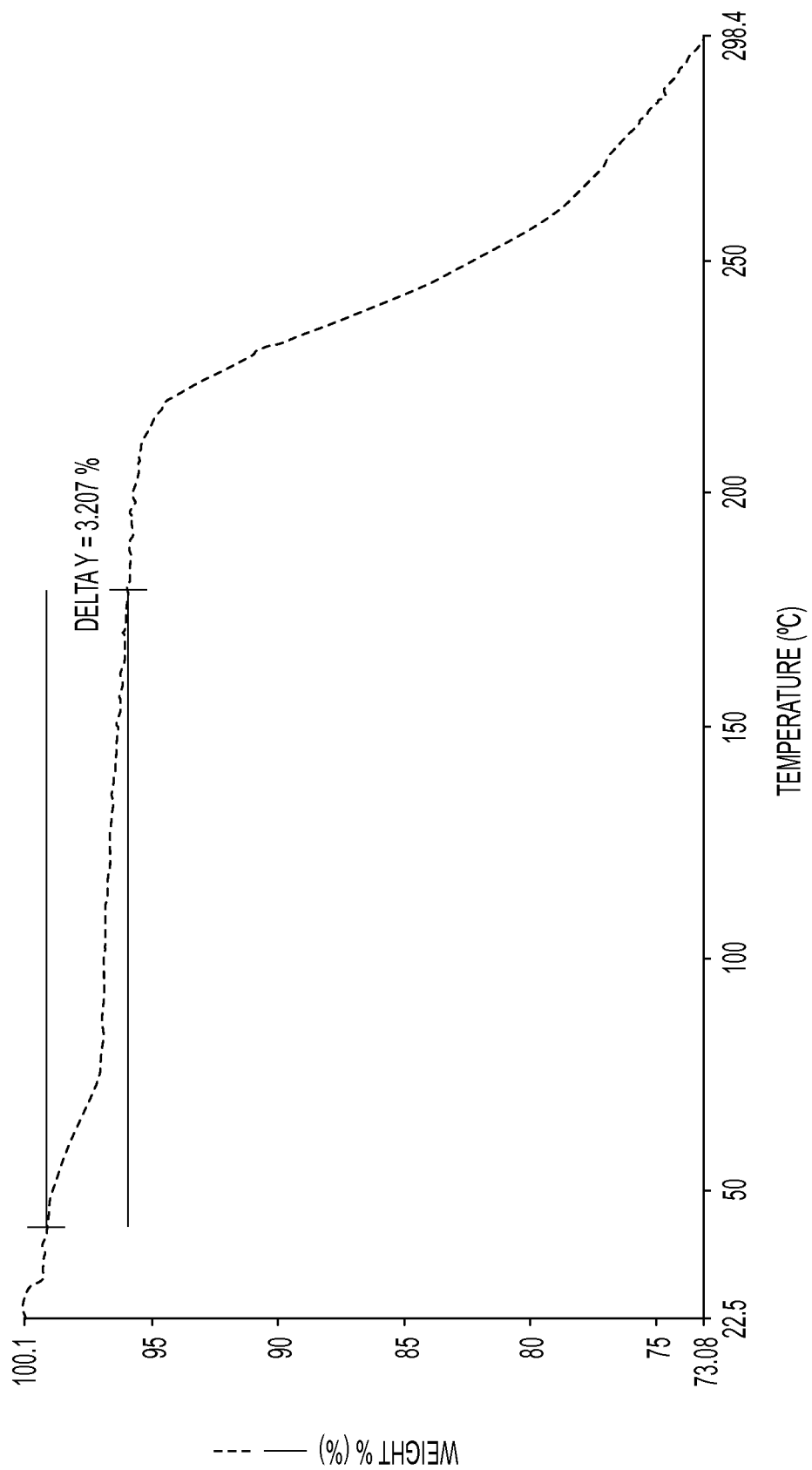
FIG. 32 depicts the TGA trace for a crystalline genistein/genistein mixture from isopropanol.

FIG. 31 shows the XRPD pattern of the crystalline genistein L-lysine salt from IPA. The peaks in the XRPD pattern at an experimental °2θ±0.2°2θ are listed in Table 23. The TGA of the crystalline genistein L-lysine/genistein mixture is shown in FIG. 32. The PLM image of the genistein L-lysine/genistein mixture from IPA snowed crystalline material as did the PLM image of the crystalline mixture from toluene.

TABLE 23

| Pos. [°2θ ± 0.2 °2θ] | d-spacing [Å] | Rel. Int. [%] |
|---|---|---|
| 5.2 | 17.1 | 31.93 |
| 7.5 | 11.7 | 73.22 |
| 12.2 | 7.2 | 16.11 |
| 12.8 | 6.9 | 50.35 |
| 14.3 | 6.2 | 19.6 |
| 14.6 | 6.1 | 24.47 |
| 14.8 | 6.0 | 30.13 |
| 16.0 | 5.5 | 43.55 |
| 16.6 | 5.3 | 12.52 |
| 18.1 | 4.9 | 100 |
| 18.6 | 4.8 | 28.99 |
| 19.2 | 4.6 | 20.18 |
| 19.7 | 4.5 | 24.98 |
| 20.6 | 4.3 | 18.1 |
| 21.0 | 4.2 | 14.36 |
| 22.4 | 4.0 | 9.6 |
| 23.2 | 3.8 | 22.54 |
| 23.6 | 3.8 | 9.93 |
| 24.8 | 3.6 | 16.59 |
| 25.1 | 3.6 | 22.5 |

TABLE 23-continued

| Pos. [°2θ ± 0.2 °2θ] | d-spacing [Å] | Rel. Int. [%] |
|---|---|---|
| 25.6 | 3.5 | 25.73 |
| 26.3 | 3.4 | 70.86 |
| 26.7 | 3.3 | 17.84 |
| 27.0 | 3.3 | 12.67 |
| 27.4 | 3.3 | 43.34 |
| 28.7 | 3.1 | 38.7 |
| 29.4 | 3.0 | 28.79 |
| 32.9 | 2.7 | 6.17 |
| 33.4 | 2.7 | 6.94 |
| 36.3 | 2.5 | 7 |
| 40.0 | 2.3 | 7.5 |

The similar XRPD patterns for the crystalline genistein L-lysine salt from both isopropanol and toluene suggests that the same crystalline genistein L-lysine salt is obtained from both preparations. The entire list of peaks from Table 21 or 22, or a subset thereof, may be sufficient to characterize crystalline genistein L-lysine salt. By comparing the crystalline genistein L-lysine salt XRPD patterns in FIGS. 30 and 31 with that of crystalline genistein in FIG. 29, one subset of peaks that, individually or in combination, may be used to characterize the crystalline genistein L-lysine salt includes 5.2, 18.6, 19.7, 20.6 and 21.0°2θ±0.2°2θ.

Example 7

Crystalline Genistein N-methylglucamine (Meglumine) Salt 7.1 Preparation of Crystalline Genistein N-methylglocamine Salt Approximately 25 mg of genistein was placed in the same vessel as ca. 20 mg of solid N-methylglucamine. To the solid mixture, 500 μL of acetone was added and the mixture shaken at ambient temperature for ca. 24 hours. Subsequent to stirring, the slurry was then temperature cycled (40° C. to ambient temperature, in 4 hour periods) with shaking for ca. 72 hours. The solid was then isolated by filtration and allowed to dry at ambient temperature for ca. 24 hours.

7.2 Characterization of Crystalline Genistein N-methylglucamine Salt

Figure 33:
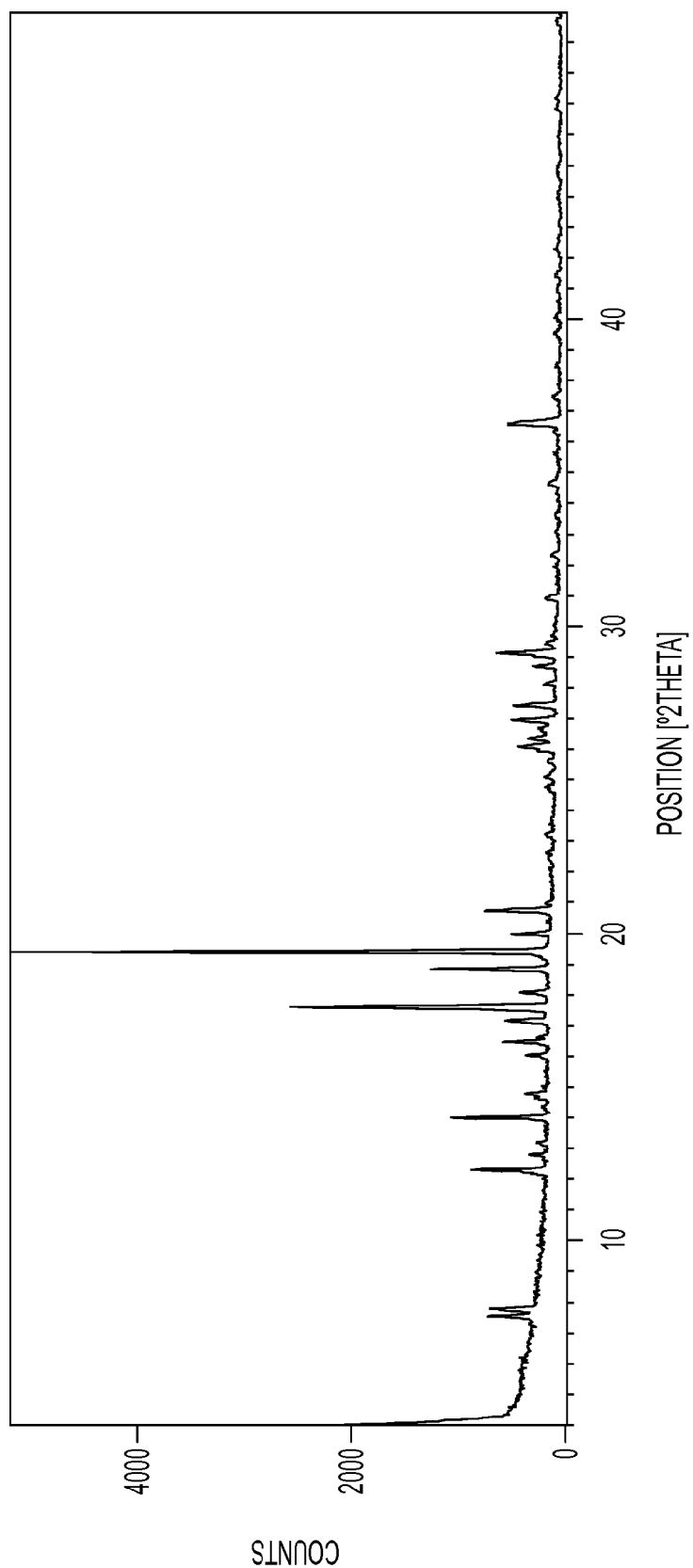
FIG. 33 depicts an XRPD pattern for crystalline genistein N-methylglucamine (meglumine) salt.

FIG. 33 shows the XRPD pattern of the crystalline genistein N-methylglucamine salt. The peaks in the XRPD pattern at an experimental °2θ±0.2°2θ are listed in Table 24. The entire list of peaks, or a subset thereof, may be sufficient to characterize crystalline genistein N-methylglucamine salt. One subset of peaks that, individually or in combination, may be used to characterize crystalline genistein N-methylgiucamine salt from FIG. 33 includes 7.5, 7.8, 12.3, 14.8, 16.5, 17.1, 17.6, 18.8, 19.4, 20.0, 20.8, and 29.1°2θ±0.2°2θ. A preferred subset includes peaks at 12.3, 14.8, 17.6, and 19.4°2θ±0.2°2θ.

TABLE 24

| Pos. [°2θ ± 0.2 °2θ] | d-spacing [Å] | Rel. Int. [%] |
|---|---|---|
| 7.5 | 11.7 | 8.64 |
| 7.8 | 11.4 | 8.13 |
| 12.3 | 7.2 | 13.7 |
| 12.8 | 6.9 | 3.35 |
| 14.0 | 6.3 | 17.93 |
| 14.8 | 6.0 | 4.11 |
| 16.0 | 5.5 | 4.38 |
| 16.5 | 5.4 | 8.33 |

TABLE 24-continued

| Pos. [°2θ ± 0.2 °2θ] | d-spacing [Å] | Rel. Int. [%] |
|---|---|---|
| 17.1 | 5.2 | 7.93 |
| 17.6 | 5.0 | 47.95 |
| 18.1 | 4.9 | 5.5 |
| 18.8 | 4.7 | 21.35 |
| 19.4 | 4.6 | 100 |
| 20.0 | 4.4 | 7.27 |
| 20.8 | 4.3 | 12.4 |
| 26.1 | 3.4 | 6.87 |
| 26.9 | 3.3 | 8.11 |
| 27.4 | 3.3 | 7.6 |
| 29.1 | 3.1 | 11.01 |
| 36.6 | 2.5 | 9.51 |

Example 8

Crystalline Genistein N-ethylglucamine (eglumine) Salt 8.1 Preparation of Crystalline Genistein N-ethylglucamine (eglumine) Salt Approximately 25 mg of genistein was placed in the same vessel as ca. 19 mg of solid N-ethylgiucamine. To the solid mixture, 500 µL of acetone or of IPA was added and the mixture shaken at ambient temperature for ca. 24 hours. Subsequent to stirring, the slurry was then temperature cycled (40'C to ambient temperature, in 4 hour periods) with shaking for ca. 72 hours. The solid was then isolated by filtration and allowed to dry at ambient temperature for ca. 24 hours.

8.2 Characterization of Crystalline Genistein N-ethylglucamine (Eglumine) Salt

Figure 34:
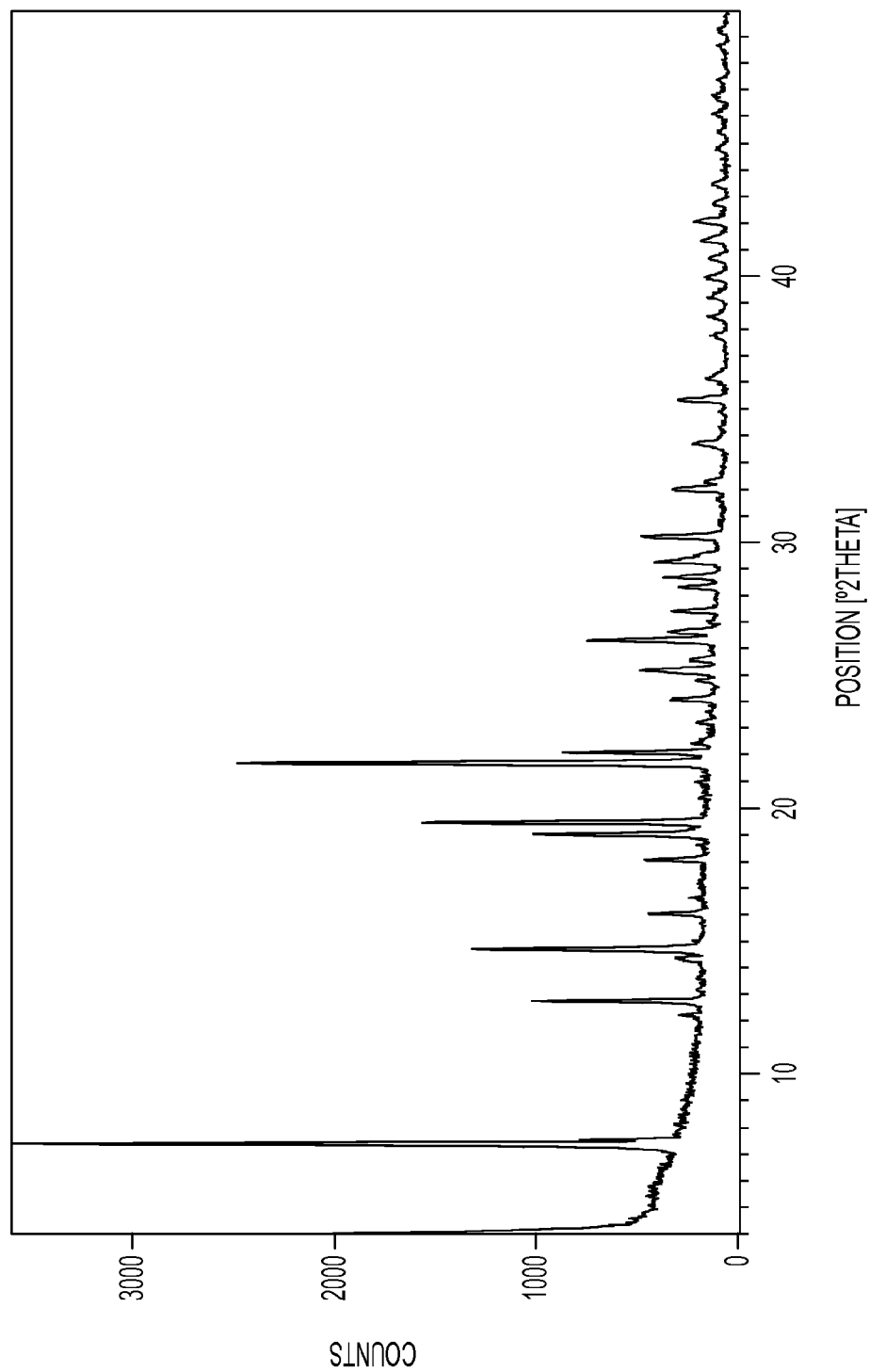
FIG. 34 depicts an XRPD pattern for crystalline genistein N-ethylglucamine (eglumine) salt, prepared from acetone.
Figure 35:
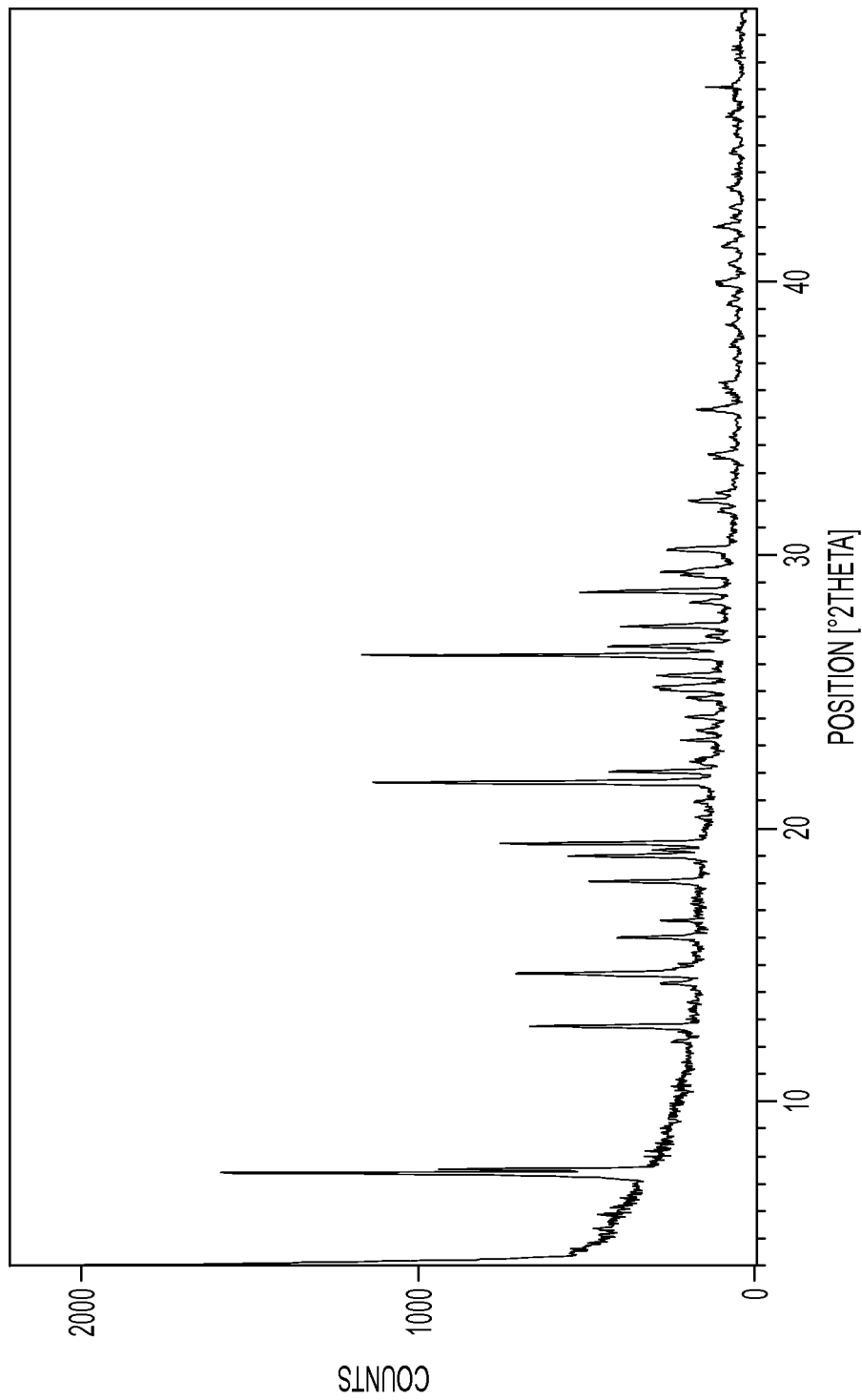
FIG. 35 depicts an XRPD pattern for crystalline genistein N-ethylgiucamine (eglumine) salt, prepared from isopropanol.
Figure 36:
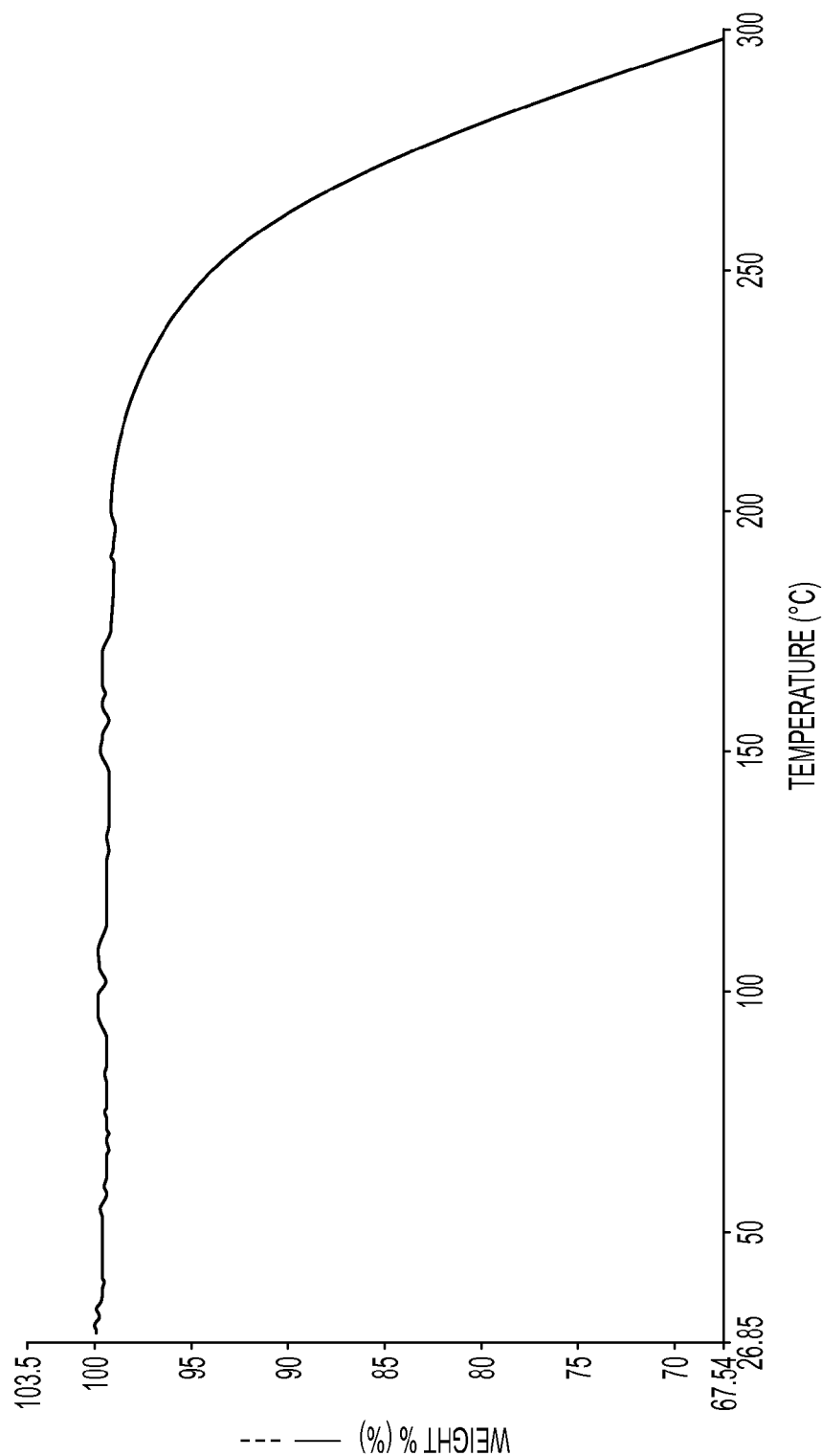
FIG. 36 depicts a TGA trace of crystalline genistein N-ethylglucamine salt from acetone.

The sample of crystalline genistein n-ethylglucamine (eglumine) salt, prepared above, was analyzed by XRPD and the patterns shown in FIGS. 34 and 35 generated. An unstable crystalline salt was identified both from acetone and IPA. FIG. 34 shows the XRPD pattern of the crystalline genistein N-ethylglucamine (eglumine) salt from acetone. The peaks in the XRPD pattern at an experimental °2θ±0.2°2θ are listed in Table 25. FIG. 35 shows the XRPD pattern of the crystalline genistein N-ethylglucamine (eglumine) salt from IPA. The peaks in the XRPD pattern at an experimental °2θ±0.2°2θ are listed in Table 26 The entire list of peaks in either Table, or a subset thereof, may be sufficient to characterize crystalline genistein N-ethylglucamine (eglumine) salt. One subset of peaks that, individually or in combination, may be used to characterize crystalline genistein N-ethylglucamine (eglumine) salt based on FIGS. 34 and 35 includes 7.4, 12.7, 14.7, 16.0, 18.1, 19.0, 19.2, 21.7, 22.1, and 26.3°2θ±0.2°2θ. A preferred subset of peaks includes 7.4, 12.7, 14.7, 16.0, 18.1, and 26.3°2θ±0.2°2θ. The TGA trace of crystalline genistein n-ethylglucamine salt from acetone is shown in FIG. 36. The PLM image of genistein n-ethylglucamine salt from acetone showed the material to be crystalline.

TABLE 25

| Pos. [°2 θ ± 0.2 °2θ] | d-spacing [Å] | Rel. Int. [%] |
|---|---|---|
| 7.4 | 12.0 | 100 |
| 7.5 | 11.7 | 14.48 |
| 12.7 | 6.9 | 25.42 |
| 14.7 | 6.0 | 34.98 |
| 16.0 | 5.5 | 8.49 |
| 18.1 | 4.9 | 9.32 |
| 19.0 | 4.7 | 26.42 |

TABLE 25-continued

| Pos. [°2 θ ± 0.2 °2θ] | d-spacing [Å] | Rel. Int. [%] |
|---|---|---|
| 19.5 | 4.6 | 43.35 |
| 21.7 | 4.1 | 72.24 |
| 22.1 | 4.1 | 22.61 |
| 24.1 | 3.7 | 6.38 |
| 25.2 | 3.5 | 10.46 |
| 26.3 | 3.4 | 19.16 |
| 26.6 | 3.3 | 7.45 |
| 27.4 | 3.3 | 7.06 |
| 28.3 | 3.2 | 6.07 |
| 28.7 | 3.1 | 8.56 |
| 29.3 | 3.1 | 9.52 |
| 30.2 | 3.0 | 11.72 |
| 32.0 | 2.8 | 7.13 |
| 32.1 | 2.8 | 6.66 |
| 33.7 | 2.7 | 4.59 |
| 35.3 | 2.5 | 7 |
| 42.0 | 2.1 | 4.96 |

TABLE 26

| Pos. [°2θ ± 0.2 °2θ] | d-spacing [Å] | Rel. Int. [%] |
|---|---|---|
| 7.4 | 12.0 | 100 |
| 7.5 | 11.7 | 49.75 |
| 12.8 | 6.9 | 37.57 |
| 14.7 | 6.0 | 42.98 |
| 16.0 | 5.5 | 19.76 |
| 16.6 | 5.3 | 8.05 |
| 18.1 | 4.9 | 27.66 |
| 19.0 | 4.7 | 32.79 |
| 19.2 | 4.6 | 12.86 |
| 19.4 | 4.6 | 48.27 |
| 21.7 | 4.1 | 80.33 |
| 22.1 | 4.0 | 24.33 |
| 23.2 | 3.8 | 8.12 |
| 24.8 | 3.6 | 7.52 |
| 25.0 | 3.6 | 14.01 |
| 25.2 | 3.5 | 15.58 |
| 25.6 | 3.5 | 14.97 |
| 26.3 | 3.4 | 84.13 |
| 26.7 | 3.3 | 27.05 |
| 27.4 | 3.3 | 24.39 |
| 28.6 | 3.1 | 33.81 |
| 29.3 | 3.0 | 11.44 |
| 29.4 | 3.0 | 16.47 |
| 30.2 | 3.0 | 14.82 |
| 32.0 | 2.8 | 10.04 |
| 33.7 | 2.7 | 6.79 |
| 35.3 | 2.5 | 8.64 |
| 47.1 | 1.9 | 7.99 |

Example 9

Crystalline Genistein Diethylamine Salt 9.1 Preparation of Crystalline Genistein Diethylamine Salt A stock solution of genistein in THF (520.2 mg in 19.25 of THF) and diethylamine in THF:ETOH (1:1) was prepared. The stock solutions of genistein and diethylamine were added together in stoichiometric amounts and the solution was filtered through 0.2 µm nylon filters into clean vials and allowed to evaporate under ambient conditions.

9.2 Characterization of Crystalline Genistein Diethylamine Salt

Figure 37:
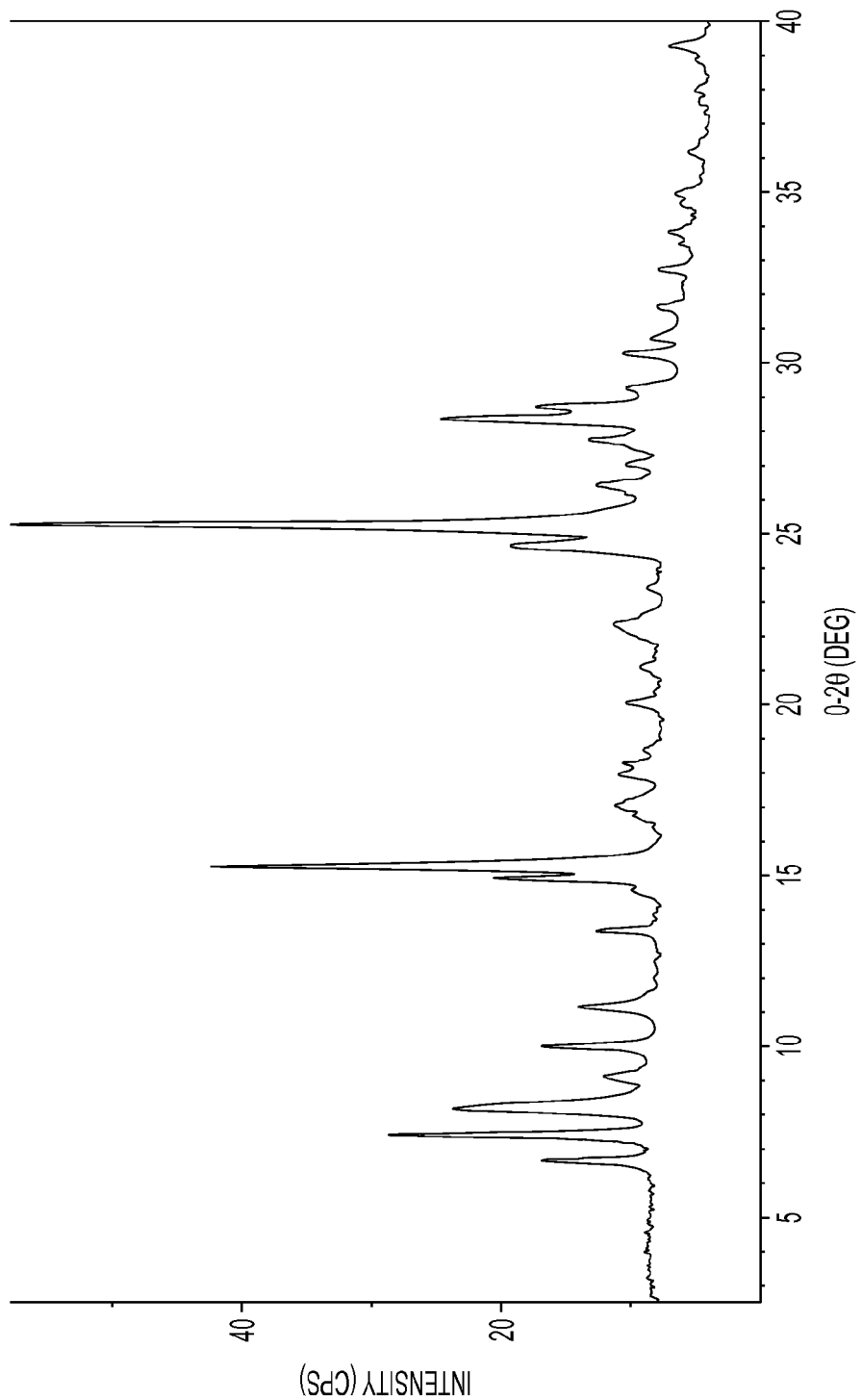
FIG. 37 depicts an XRPD pattern for crystalline genistein diethylamine salt.

The solid material isolated above was subjected to XRPD analysis using an Inel XRG-3000 diffractometer equipped with a CPS (Curved Position Sensitive) detector with a 2θ range of 120°; a Shimadzu XRD-6000 X-ray powder diffractometer using Cu Kα radiation and a Bruker D-8 Discover diffractometer equipped with Bruker's General Area Diffraction Detection System (GADDS, v. 4.1.19). The specific acquisition parameters are listed on the pattern of each sample in the data section. FIG. 37 shows the XRPD pattern of the crystalline genistein diethylamine salt. The peaks in the XRPD pattern at an experimental °2θ±0.2°2θ are listed in Table 27. The entire list of peaks, or a subset thereof, may be sufficient to characterize crystalline genistein diethylamine salt. One subset of peaks that, individually or in combination, may be used to characterize crystalline genistein diethylamine salt from FIG. 37 includes 7.4, 8.2, 15.3, 25.3, and 28.4°2θ±0.1°2θ.

TABLE 27

| °2θ | d space (Å) | Intensity (%) |
|---|---|---|
| 6.7 ± 0.1 | 13.215 ± 0.200 | 30 |
| 7.4 ± 0.1 | 11.922 ± 0.163 | 50 |
| 8.2 ± 0.1 | 10.768 ± 0.133 | 41 |
| 9.1 ± 0.1 | 9.671 ± 0.107 | 21 |
| 10.0 ± 0.1 | 8.837 ± 0.089 | 29 |
| 11.2 ± 0.1 | 7.910 ± 0.071 | 25 |
| 13.4 ± 0.1 | 6.608 ± 0.049 | 22 |
| 14.9 ± 0.1 | 5.937 ± 0.040 | 36 |
| 15.3 ± 0.1 | 5.803 ± 0.038 | 73 |
| 17.1 ± 0.1 | 5.185 ± 0.030 | 20 |
| 18.0 ± 0.1 | 4.937 ± 0.027 | 19 |
| 18.3 ± 0.1 | 4.844 ± 0.026 | 18 |
| 20.1 ± 0.1 | 4.430 ± 0.022 | 18 |
| 21.1 ± 0.1 | 4.207 ± 0.020 | 16 |
| 22.4 ± 0.1 | 3.969 ± 0.018 | 20 |
| 23.4 ± 0.1 | 3.796 ± 0.016 | 15 |
| 24.7 ± 0.1 | 3.607 ± 0.014 | 33 |
| 25.3 ± 0.1 | 3.524 ± 0.014 | 100 |
| 26.5 ± 0.1 | 3.370 ± 0.013 | 22 |
| 27.0 ± 0.1 | 3.297 ± 0.012 | 18 |
| 27.8 ± 0.1 | 3.213 ± 0.011 | 23 |
| 28.4 ± 0.1 | 3.143 ± 0.011 | 43 |
| 28.7 ± 0.1 | 3.110 ± 0.011 | 30 |
| 29.3 ± 0.1 | 3.049 ± 0.010 | 18 |

Example 10

Crystalline Genistein Monohydrate 10.1 Preparation of Crystalline Genistein Monohydrate A stock solution of genistein was prepared in THF (472 mg in 17.47 mL of THF). Genistein stock solution (1 mL) was added to a glass vial, followed by 1 mL of D-glucuronic acid solution (84.1 mg in 4.33 of water). The solution was allowed to evaporate under ambient conditions. Solids were isolated after 1 day by decanting the remaining solution and were then blotted dry with filter paper.

10.2 Characterization of Crystalline Genistein Monohydrate

Figure 38:
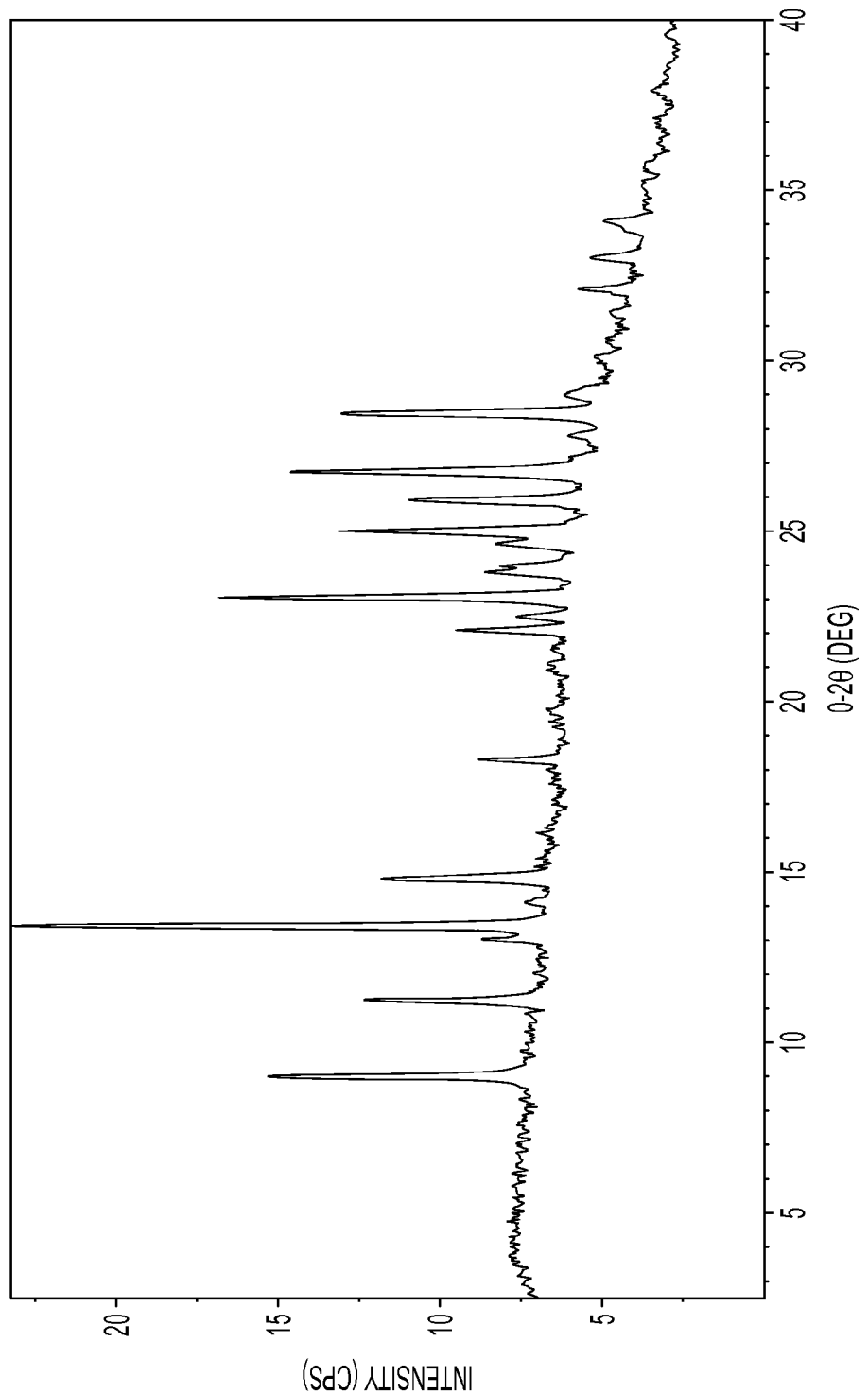
FIG. 38 depicts an XRPD pattern for crystalline genistein monohydrate.

XRPD analysis of the crystalline genistein monohydrate sample was performed using an Inel XRG-3000 diffractometer equipped with a CPS (Curved Position Sensitive) detector with a 2θ range of 120°; a Shimadzu XRD-6000 X-ray powder diffractometer using Cu Kα radiation; and a Bruker D-8 Discover diffractometer equipped with Bruker's General Area Diffraction Detection System (GADDS, v. 4.1.19). FIG. 38 shows the XRPD pattern of the crystalline genistein monohydrate. The peaks in the XRPD pattern at an experimental °2θ±0.2°2θ are listed in Table 28. The entire list of peaks, or a subset thereof, may be sufficient to characterize crystalline genistein monohydrate. One subset of peaks that, individually or in combination, may be used to characterize crystalline genistein monohydrate from FIG. 38 includes 9.0, 11.3, 13.4, 14.8, 23.1, 25.0, 26.8, and 28.5 2θ±0.1°2θ.

TABLE 28

| °2θ | d space (Å) | Intensity (%) |
|---|---|---|
| 9.0 ± 0.1 | 9.819 ± 0.110 | 65 |
| 11.3 ± 0.1 | 7.862 ± 0.070 | 52 |
| 13.0 ± 0.1 | 6.800 ± 0.052 | 36 |
| 13.4 ± 0.1 | 6.591 ± 0.049 | 100 |
| 14.1 ± 0.1 | 6.269 ± 0.044 | 31 |
| 14.8 ± 0.1 | 5.992 ± 0.041 | 50 |
| 18.3 ± 0.1 | 4.844 ± 0.026 | 36 |
| 22.1 ± 0.1 | 4.024 ± 0.018 | 40 |
| 22.5 ± 0.1 | 3.951 ± 0.017 | 32 |
| 23.1 ± 0.1 | 3.857 ± 0.017 | 70 |
| 23.8 ± 0.1 | 3.741 ± 0.016 | 36 |
| 24.0 ± 0.1 | 3.709 ± 0.015 | 34 |
| 24.7 ± 0.1 | 3.612 ± 0.014 | 34 |
| 25.0 ± 0.1 | 3.562 ± 0.014 | 55 |
| 25.9 ± 0.1 | 3.436 ± 0.013 | 45 |
| 26.8 ± 0.1 | 3.331 ± 0.012 | 61 |
| 27.8 ± 0.1 | 3.209 ± 0.011 | 25 |
| 28.5 ± 0.1 | 3.136 ± 0.011 | 54 |
| 29.0 ± 0.1 | 3.081 ± 0.010 | 26 |

Figure 39:
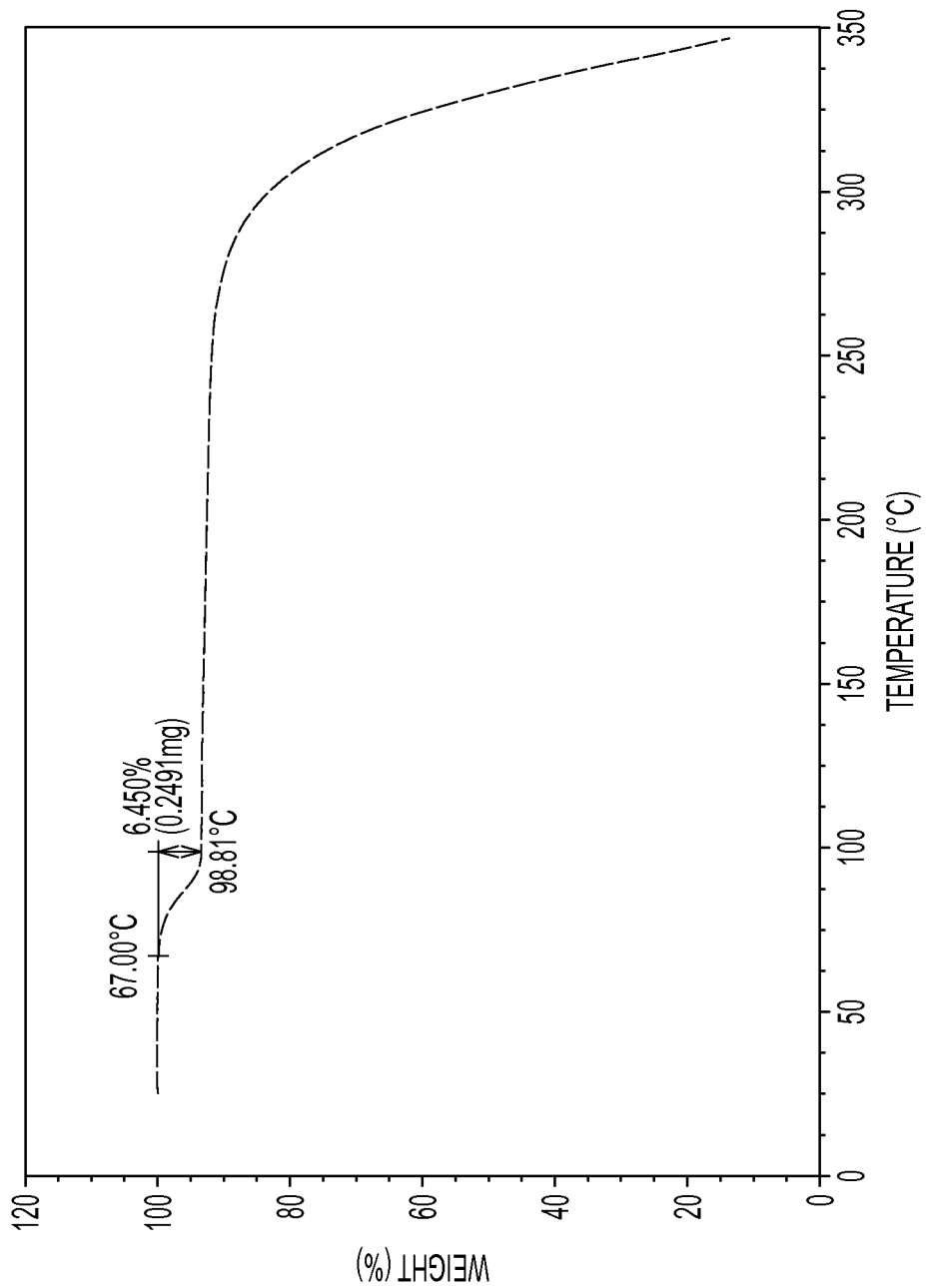
FIG. 39 depicts a TGA trace of crystalline genistein monohydrate.

The thermogravimetric analysis (TGA) of crystalline genistein monohydrate was performed using a TA Instruments 2950 thermogravimetric analyzer. FIG. 39 shows the TGA trace of the crystalline genistein monohydrate sample. Thermogravimetric analysis indicated that the sample contained 6% by weight of volatile component, which is equivalent to a monohydrate.

The invention claimed is:

1. A genistein composition selected from:
   genistein potassium dihydrate,
   a genistein calcium salt,
   a genistein magnesium salt,
   a genistein L-lysine salt,
   a genistein N-methylglucamine salt,
   a genistein N-ethylglucamine salt,
   a genistein diethylamine salt, and
   crystalline genistein monohydrate.

2. The genistein composition of claim 1, wherein the composition is genistein potassium dihydrate of claim 19 in the form of crystalline genistein potassium salt dihydrate characterized by an XRPD pattern having peaks at 11.6, 14.5, 24.5, 25.2 and at least two of the three peaks 27.6, 28.0, and 28.4 ° 2θ±0.2° 2θ.

3. The genistein composition of claim 1 wherein the composition is a crystalline genistein calcium salt, a crystalline genistein magnesium salt, a crystalline genistein L-lysine salt, a crystalline genistein N-methylglucamine salt, a crystalline genistein N-ethylglucamine salt, or a crystalline genistein diethylamine salt.

4. The genistein composition of claim 1, wherein the composition is crystalline genistein monohydrate.

5. A therapeutic composition comprising a therapeutically effective amount of the genistein composition of claim 1 and at least one pharmaceutically acceptable carrier.

6. A method of treating chronic inflammation or inflammatory diseases comprising the step of administering to a patient in need thereof a therapeutically effective amount of the therapeutic composition of claim 5.

7. A method for treating chronic inflammation or inflammatory diseases comprising the step of administering to a patient in need thereof a therapeutically effective amount of the genistein composition of claim 1.

8. A method for treating transthyretin amyloidosis comprising the step of administering to a patient in need thereof a therapeutically effective amount of the therapeutic composition of claim 5.

9. A method for treating transthyretin amyloidosis comprising the step of administering to a patient in need thereof a therapeutically effective amount of the genistein composition of claim 1.

10. A method for treating cystic fibrosis comprising the step of administering to a patient in need thereof a therapeutically effective amount of the therapeutic composition according to claim 5.

11. A method for treating cystic fibroses comprising the step of administering to a patient in need thereof a therapeutically effective amount of the genistein composition of claim 1.

12. A method for treating infection comprising the step of administering to a patient in need thereof a therapeutically effective amount of the therapeutic composition according to claim 5.

13. A method for treating infection comprising the step of administering to a patient in need thereof a therapeutically effective amount of the genistein composition of claim 1.

14. The genistein composition of claim 3, wherein the crystalline genistein diethylamine salt is characterized by an XRPD pattern of FIG. 37.

15. The genistein composition of claim 3, wherein the crystalline genistein diethylamine salt is characterized by an XRPD pattern having peaks at 7.4, 8.2, 15.3, 25.3, and 28.4 ° 2θ±0.1° 2θ.

16. A method of arresting or suppressing the development of clinical symptoms related to cancer comprising the step of administering to a patient in need thereof a therapeutically effective amount of the therapeutic composition of claim 5.

17. A method of arresting or suppressing the development of clinical symptoms related to cancer comprising the step of administering to a patient in need thereof a therapeutically effective amount of the genistein composition of claim 1.

18. The method of claim 16, wherein said cancer is selected from the group consisting of colorectal cancer, gastric cancer, esophageal cancer, breast cancer, lung cancer, prostate cancer, bladder cancer, brain cancer, renal cancer, ovarian cancer, liver cancer, skin cancer, thyroid cancer, pancreatic cancer, leukemia, and lymphoma.

19. The method of claim 17, wherein said cancer is selected from the group consisting of colorectal cancer, gastric cancer, esophageal cancer, breast cancer, lung cancer, prostate cancer, bladder cancer, brain cancer, renal cancer, ovarian cancer, liver cancer, skin cancer, thyroid cancer, pancreatic cancer, leukemia, and lymphoma.

* * * * *